United States Patent
Bremel

(10) Patent No.: US 11,069,427 B2
(45) Date of Patent: Jul. 20, 2021

(54) MATHEMATICAL PROCESSES FOR DETERMINATION OF PEPTIDASE CLEAVAGE

(71) Applicant: IOGENETICS, LLC, Madison, WI (US)

(72) Inventor: Robert D. Bremel, Hillpoint, WI (US)

(73) Assignee: IOGENETICS, LLC, Madison, WI (US)

( * ) Notice: Subject to any disclaimer, the term of this patent is extended or adjusted under 35 U.S.C. 154(b) by 949 days.

(21) Appl. No.: 14/895,748

(22) PCT Filed: Jun. 9, 2014

(86) PCT No.: PCT/US2014/041525
§ 371 (c)(1),
(2) Date: Dec. 3, 2015

(87) PCT Pub. No.: WO2014/200912
PCT Pub. Date: Dec. 18, 2014

(65) Prior Publication Data
US 2016/0117441 A1 Apr. 28, 2016

Related U.S. Application Data

(60) Provisional application No. 61/833,256, filed on Jun. 10, 2013.

(51) Int. Cl.
| | |
|---|---|
| *G16B 20/00* | (2019.01) |
| *G16B 5/00* | (2019.01) |
| *G16B 40/00* | (2019.01) |
| *G06N 3/04* | (2006.01) |
| *G06N 3/08* | (2006.01) |

(52) U.S. Cl.
CPC .......... *G16B 20/00* (2019.02); *G06N 3/0472* (2013.01); *G06N 3/08* (2013.01); *G16B 5/00* (2019.02); *G16B 40/00* (2019.02)

(58) Field of Classification Search
None
See application file for complete search history.

(56) References Cited

U.S. PATENT DOCUMENTS 8,455,203 B2   6/2013   Wang et al.

FOREIGN PATENT DOCUMENTS

| WO | 2011/119484 | 9/2011 |
|---|---|---|
| WO | 2013/040142 | 3/2013 |

OTHER PUBLICATIONS

Ning et al. Drug Development Research 72, p. 138-146, 2011.*
Murphy et al. Nature Chemical Biology, 7, 327-330, 2011.*
Hecht et al. Drug Development Research 72, p. 53-65, 2011.*
Artigas, G. et al. Purification Process to Obtain Cahthepsin D, B and L Suitable to Be Used in Food Industry. Food Biotechnology, 1996, vol. 10, No. 1; pp. 41-45; Abstract only.
Blom, N. et al "Cleavage site analysis in picornaviral polyproteins: Discovering cellular targets by neural networks" Protein Science, vol. 5, No. 11, Nov. 1, 1996, pp. 2203-2216.
Bremel, R. et al. An Integrated Approach to Epitope Analysis I: Dimensional reduction, visualization and prediction of MHC binding using amino acid principal components and regression approaches Immunome Res. Nov. 2, 2010, vol. 6, No. 1, p. 7.
Bremel, R. et al. An Integrated Approach to Epitope Analysis II: A System for Proteomic-Scale Prediction of Immunological Characteristics. Immunome Res. Nov. 2, 2010, vol. 6, No. 8, pp. 1-21.
European Search Report, EP Application No. 14810932.5, dated Dec. 7, 2016.
Guha, S. et al. Cathepsins: Fundatmental Effectors of Endolysosomal Proteolysis. Indian J. Biochem Biophys. Apr. 2008, vol. 45, No. 2; pp. 75-90.
International Search Report, Int'l Patent Application No. PCT/US2014/041525, dated Dec. 23, 2014.
Reiser, J. et al. Specialized Roles for Cysteine Cathepsins in Health and Diseas. J Clin Invest. Oct. 2010, vol. 120, No. 10; pp. 3421-3431; p. 3427, first column, first paragraph.
Shi, G. et al. Molecular Cloning and Expression of Human Alveolar Macrophage Cathepsin S, An Alastinolytic Cysteine Protease. J Biol Chem. Apr. 15, 1992, vol. 267, No. 11, pp. 7258-7562.
Song, J. et al. PROSPER: An Integrated Feature-Based Tool for Predicting Protease Substrate Cleavage Sites. PLoS ONE. Nov. 29, 2012, vol. 7, No. 11.
Tedelind, et al. Nuclear Cysteine Cathepsin Variants in Thyroid Carcinoma Cells. Biol. Chem. Aug. 2010, vol. 391; pp. 923-935, p. 924, first column, second paragraph.

* cited by examiner

*Primary Examiner* — Michael L Borin
(74) *Attorney, Agent, or Firm* — Casimir Jones S.C.; J. Mitchell Jones

(57) ABSTRACT

This invention relates to the identification of peptidase cleavage sites in proteins and in particular to identification protease cleavage by the endopeptidases. The present invention utilizes a bioinformatic methodology for prediction of peptidase cleavage sites based on principal component analysis and based on training sets obtained by experimental protein cleavage. This invention is not limited to training sets derived from CSL approaches, nor to any other experimental determination of cleavage site.

Figure 1:
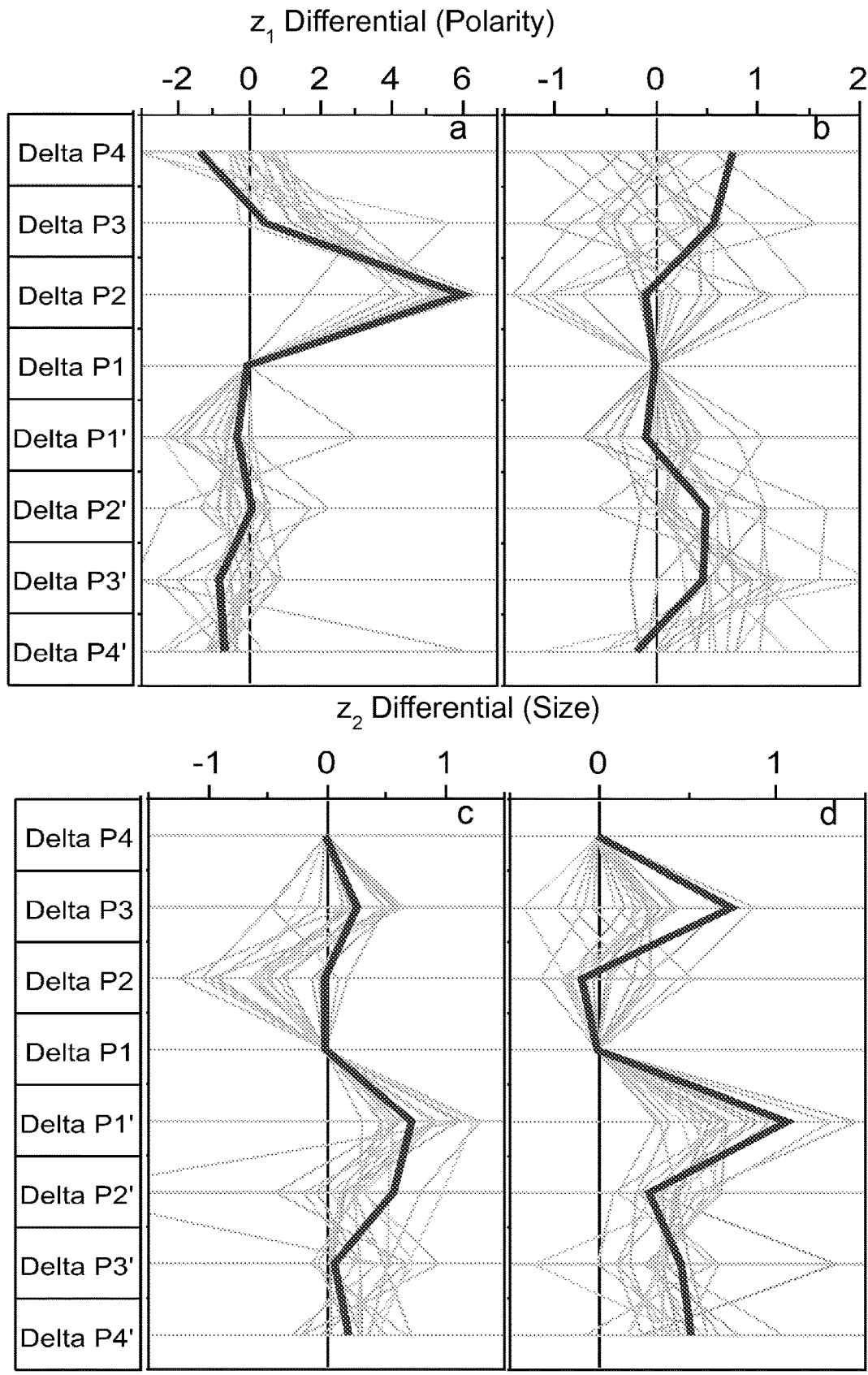

15 Claims, 26 Drawing Sheets
Specification includes a Sequence Listing.

Weighting Matrix

[ 0.1250  0.1250  0.1250  0.1250  0.1250  0.1250  0.1250  0.1250, 0.0333  0.0667  0.1333  0.2667  0.2667  0.1333  0.0667  0.0333, 0.0615  0.0923  0.1385  0.2077  0.2077  0.1385  0.0923  0.0615, 0.0867  0.1084  0.1355  0.1694  0.1694  0.1355  0.1084  0.0867 ]

(Weight Matrix Pattern

[1, 1, 1, 1, 1, 1, 1, 1, Σ = 8] )

( [1, 2, 4, 8, 8, 4, 2, 1, Σ = 30] )

( [1, 1.5, 2.25, 3.375, 3.375, 2.25, 1.5, 1, Σ = 16.25] )

( [1, 1.25, 1.5625, 1.953125, 1.953125, 1.5625, 1.25, 1, Σ = 11.53125] )

Human Cathepsin L a) Murine Cathepsin D 340 uncleaved
b) Murine Cathepsin D 34 cleaved
c) Murine Cathepsin E 660 uncleaved
d) Murine Cathepsin E 66 cleaved Human Cathepsin B Human Cathepsin S@ pH7.5

Figure 12A

| Percent Misclassification Using Validation Data | | | | | | | | | | | | | |
|---|---|---|---|---|---|---|---|---|---|---|---|---|---|
| Benchmark | Single tree | TreeBoost | Tree forest | SVM | ANN | PNN | GMDH | CCNN | RBF | LDA | K-Means | Linear Reg. | Logistic reg. |
| Abalone | 46 | 45 | 45 | 45 | 43 | 44 | 45 | 44 | 44 | 45 | 52 | 45 | |
| Ad | 3 | 3 | 3 | 3 | 16 | 2 | | 3 | 9 | 3 | 20 | 45 | |
| AdultCensus | 20 | 14 | 15 | 20 | 15 | 13 | 16 | 15 | 14 | 16 | 44 | 19 | |
| Anneal steel | 11 | 5 | 23 | 11 | | 6 | 14 | 9 | 24 | 18 | 11 | 17 | |
| Argentina currency | 27 | 14 | 24 | 32 | 40 | 16 | 29 | 20 | 22 | 24 | 41 | 23 | 28 |
| Astroparticle | 4 | 2 | 3 | 3 | 4 | 3 | 4 | 3 | 3 | 10 | 6 | 11 | 5 |
| Audiology | 61 | 19 | 36 | 15 | | 9 | 24 | 20 | 19 | 25 | 49 | 20 | |
| AustralianCrabSex | 14 | 8 | 7 | 3 | 3 | 4 | 5 | 2 | 5 | 4 | 13 | 4 | 4 |
| AustralianCredit | 15 | 13 | 13 | 24 | 14 | 12 | 14 | 14 | 15 | 15 | 38 | 15 | 15 |
| Balance | 22 | 15 | 18 | 0 | 3 | 10 | 9 | 4 | 9 | 14 | 30 | 14 | |
| Banana shape | 10 | 10 | 11 | 10 | 10 | 10 | 32 | 45 | 11 | 44 | 11 | 44 | 44 |
| Bands | 29 | 19 | 20 | 25 | 36 | 7 | 33 | 24 | 24 | 26 | 34 | 25 | |
| Bioinformatics | 38 | 18 | 21 | 18 | 14 | 16 | 20 | 18 | 26 | 17 | 27 | 17 | 21 |
| Bisbey | 19 | 10 | 12 | 18 | 22 | 14 | 19 | 16 | 25 | 18 | 29 | 1 | |
| Bridges | 30 | 24 | 36 | 57 | 81 | 25 | 35 | 24 | 31 | 33 | 61 | 27 | |
| Car | 4 | 1 | 4 | 0 | 1 | 13 | 13 | 2 | 6 | 10 | 26 | 16 | |
| ChurchParticipation | 63 | 56 | 58 | 55 | 54 | 47 | 55 | 49 | 54 | 49 | 56 | 51 | |
| ClevelandHeart14 | 58 | 46 | 44 | 48 | 46 | 39 | 42 | 41 | 43 | 40 | 71 | 58 | |
| ColonTumor | 19 | 8 | 16 | 20 | 19 | 10 | 19 | 24 | 35 | 23 | 14 | | |
| Contraception | 44 | 44 | 44 | 46 | 44 | 45 | 46 | 45 | 46 | 49 | 54 | 49 | |
| CreditApplication | 14 | 9 | 13 | 14 | 45 | 12 | 15 | 14 | 14 | 14 | 41 | 15 | |

Figure 12B

| | | | | | | | | | | | | |
|---|---|---|---|---|---|---|---|---|---|---|---|---|
| Cushing's Syndrome | 30 | 33 | 16 | 41 | 26 | 7 | 37 | 52 | 30 | 41 | 26 | 44 | |
| DeathPenalty | 31 | 25 | 26 | 31 | 26 | 7 | 25 | 24 | 24 | 25 | 36 | 24 | 26 |
| Dermatology | 4 | 3 | 3 | 0 | 65 | 0 | 3 | 4 | 3 | 3 | 9 | 2 | |
| DNA | 7 | 4 | 30 | 4 | 6 | 4 | 7 | 5 | 5 | 6 | 10 | 5 | |
| Ecoli | 22 | 14 | 14 | 16 | 15 | 12 | 12 | 13 | 14 | 13 | 18 | 15 | |
| ElectroCardiogram | 26 | 23 | 24 | 25 | 29 | 22 | 27 | 23 | 32 | 26 | 49 | 24 | 27 |
| EvansCounty | 12 | 11 | 11 | 25 | 11 | 10 | 11 | 10 | 12 | 10 | 30 | 10 | 10 |
| Federalist | 5 | 5 | 5 | 4 | 5 | 0 | 7 | 6 | 11 | 15 | 10 | 15 | 12 |
| Flags | 45 | 32 | 46 | 36 | 31 | 25 | 46 | 44 | 37 | 36 | 62 | 34 | |
| Fraud | 26 | 29 | 31 | 45 | 31 | 14 | 29 | 33 | 36 | 29 | 31 | 31 | 29 |
| GermanCredit | 33 | 24 | 25 | 23 | 25 | 20 | 26 | 24 | 26 | 24 | 45 | 24 | 24 |
| GfaNormaux | 6 | 5 | 6 | 4 | 3 | 2 | 8 | 6 | 5 | 5 | 12 | 7 | 8 |
| Glass | 30 | 24 | 22 | 34 | 35 | 12 | 36 | 34 | 28 | 36 | 28 | 40 | |
| GymTutor | 7 | 4 | 10 | 4 | 4 | 2 | 7 | 4 | 4 | 11 | 25 | 11 | |
| Haberman | 30 | 33 | 39 | 33 | 27 | 24 | 27 | 25 | 26 | 25 | 49 | 26 | 25 |
| Hayes-Roth | 15 | 29 | 33 | 23 | 30 | 18 | 22 | 26 | 21 | 33 | 29 | 37 | |
| Heart13 | 46 | 21 | 16 | 18 | 31 | 14 | 21 | 13 | 17 | 21 | 56 | 15 | 25 |
| Hepatitis | 21 | 15 | 21 | 21 | 16 | 6 | 21 | 15 | 16 | 15 | 28 | 14 | 20 |
| HorseColic | 20 | 17 | 18 | 16 | 17 | 7 | 21 | 21 | 21 | 18 | 42 | 49 | |
| HOSLEM | 50 | 33 | 33 | 34 | 34 | 25 | 33 | 31 | 34 | 31 | 42 | 33 | 33 |
| HouseVotes | 5 | 4 | 3 | 3 | 3 | 2 | 5 | 3 | 4 | 4 | 8 | 4 | 3 |
| InsuranceFraud | 27 | 18 | 31 | 29 | 27 | 5 | 17 | 19 | 24 | 28 | 32 | 24 | |
| Ionosphere | 9 | 7 | 6 | 5 | 10 | 8 | 10 | 10 | 9 | 14 | 20 | 14 | 13 |
| Iris | 5 | 3 | 3 | 3 | 3 | 3 | 4 | 4 | 2 | 2 | 4 | 15 | |
| Labor-neg | 12 | 10 | 5 | 7 | | 0 | 22 | 12 | 7 | 10 | 15 | 10 | 10 |
| Lenses | 25 | 17 | 42 | 12 | 37 | 4 | 33 | 21 | 17 | 12 | 21 | 21 | |
| Letter-recognition | 14 | 4 | 0 | 2 | 95 | 2 | 31 | 20 | 14 | 30 | 5 | 44 | |
| LibSvmVehicle | 25 | 16 | 16 | 20 | 17 | 17 | 17 | 17 | 20 | 18 | 21 | 19 | |
| LiverDisorder | 32 | 29 | 26 | 29 | 30 | 30 | 28 | 29 | 30 | 30 | 41 | 30 | 34 |
| LowBwt | 36 | 34 | 34 | 35 | 30 | 30 | 29 | 29 | 31 | 31 | 37 | 30 | 36 |
| LungCancer | 50 | 50 | 57 | 47 | 44 | 6 | 61 | 56 | 62 | 50 | 53 | | |
| Lymphography | 22 | 14 | 22 | 17 | 15 | 5 | 19 | 16 | 16 | 21 | 22 | 13 | |
| Marketing | 53 | 48 | 51 | 50 | 93 | 45 | 45 | 44 | 43 | 47 | 60 | 48 | |
| Microchip | 33 | 35 | 36 | 38 | 34 | 34 | 34 | 34 | 37 | 34 | 49 | 34 | 34 |
| Mushrooms | 0 | 0 | 0 | 0 | 0 | 0 | 0 | 0 | 0 | 0 | 0 | 0 | |
| Musk | 24 | 10 | 10 | 6 | 9 | 4 | 27 | 13 | 43 | 19 | 13 | 18 | 18 |
| NLS | 42 | 33 | 31 | 31 | 29 | 29 | 30 | 29 | 36 | 30 | 41 | 32 | |
| Nursery | 2 | 0 | 45 | 0 | 0 | 2 | 13 | 0 | 4 | 47 | 19 | 9 | |
| NursingHome | 20 | 7 | 6 | 16 | 7 | 4 | 5 | 5 | 5 | 6 | 25 | 6 | 16 |
| OilSpill | 12 | 7 | 18 | 10 | 3 | 3 | 4 | 3 | 4 | 3 | 16 | 3 | |
| Optdigits | 10 | 2 | 2 | 1 | 4 | 1 | 8 | 3 | 5 | 4 | 2 | 7 | |
| Pageblocks | 8 | 5 | 2 | 8 | 4 | 3 | 5 | 3 | 10 | 5 | 80 | 8 | |
| PenDigits | 4 | 2 | 1 | 0 | 3 | 1 | 6 | 2 | 2 | 11 | 1 | 12 | |
| P.I.-Diabetes | 25 | 24 | 26 | 24 | 23 | 16 | 23 | 22 | 24 | 23 | 29 | 23 | 26 |
| PostOperative | 55 | 42 | 43 | 51 | 34 | 29 | 39 | 37 | 38 | 38 | 41 | 33 | |
| PrimaryTumor | 74 | 59 | 68 | 60 | 79 | 55 | 55 | 52 | 53 | 55 | 70 | 52 | |
| Reuters | 11 | 5 | 4 | 3 | 3 | 11 | | 7 | 13 | 23 | 12 | | |
| RingNorm | 13 | 2 | 4 | 1 | 3 | 49 | 7 | 7 | 2 | 23 | 18 | 23 | 24 |
| SalesPlan | 65 | 59 | 61 | 56 | 63 | 63 | 63 | 59 | 64 | 61 | 66 | 60 | |
| Satellite | 15 | 8 | 8 | 8 | 11 | 8 | 14 | 12 | 10 | 16 | 10 | 24 | |

Figure 12C

| | | | | | | | | | | | | | |
|---|---|---|---|---|---|---|---|---|---|---|---|---|---|
| Segment | 5 | 2 | 2 | 0 | 3 | 3 | 7 | 5 | 17 | 8 | 4 | 15 | |
| Shuttle | 1 | 1 | 1 | 0 | 0 | 0 | 5 | 0 | 21 | 6 | 21 | 13 | |
| Smoking | 65 | 49 | 41 | 66 | 31 | 31 | 32 | 32 | 32 | 32 | 55 | 31 | |
| Sonar | 24 | 13 | 13 | 13 | 21 | 1 | 28 | 26 | 26 | 24 | 16 | 24 | 26 |
| SpamBase | 7 | 6 | 5 | 6 | 7 | 9 | 11 | 7 | 39 | 10 | 34 | 9 | 7 |
| Specif | 27 | 17 | 20 | 21 | 24 | 6 | 25 | 22 | 27 | 41 | 26 | 41 | 39 |
| Splice DNA | 5 | 4 | 35 | 3 | 5 | 3 | 7 | 5 | 4 | 5 | 10 | 5 | |
| Spiral | 47 | 42 | 47 | 8 | 60 | 24 | 52 | 57 | 24 | 51 | 23 | 51 | 51 |
| SvmTumor | 46 | 25 | 24 | 24 | 30 | 60 | 36 | 33 | 83 | 33 | 27 | 30 | |
| Tae | 51 | 47 | 61 | 51 | 60 | 48 | 56 | 54 | 53 | 50 | 44 | 52 | |
| Thyroid (ANN) | 2 | 2 | 3 | 3 | 5 | 2 | | 1 | 1 | 6 | 56 | 7 | |
| Tic-tac-toe | 6 | 1 | 1 | 0 | 2 | 2 | 26 | 2 | 2 | 2 | 14 | 2 | 2 |
| Tin | 49 | 29 | 28 | 34 | 26 | 24 | 27 | 26 | 24 | 26 | 50 | 26 | 26 |
| Titanic | 21 | 24 | 22 | 21 | 21 | 21 | 22 | 21 | 21 | 22 | 30 | 22 | 22 |
| TorchClassif | 16 | 9 | 7 | 9 | 12 | 3 | 28 | 13 | 12 | 27 | 8 | 27 | 27 |
| Twonorm | 15 | 2 | 3 | 2 | 2 | 2 | 11 | 2 | 3 | 2 | 3 | 2 | 2 |
| UTI | 69 | 78 | 85 | 71 | 58 | 64 | 74 | 64 | 54 | 62 | 80 | 54 | |
| Vehicle | 28 | 24 | 24 | 14 | 19 | 25 | 27 | 22 | 15 | 22 | 35 | 24 | |
| Vibration | 60 | 60 | 60 | 61 | 50 | 48 | 50 | 49 | 48 | 51 | 68 | 51 | |
| Vowel | 17 | 7 | 3 | 2 | 5 | 0 | 20 | 11 | 7 | 28 | 1 | 37 | |
| Waveform | 22 | 15 | 15 | 13 | 13 | 15 | 16 | 13 | 14 | 14 | 15 | 14 | |
| WBDC | 7 | 5 | 6 | 4 | 36 | 6 | 7 | 7 | 6 | 7 | 14 | 7 | 7 |
| Wine | 8 | 3 | 2 | 1 | 2 | 0 | 3 | 2 | 1 | 2 | 24 | 2 | |
| Zoo | 12 | 7 | 7 | 4 | 5 | 1 | 5 | 4 | 6 | 9 | 4 | 4 | |
| Average error | 24.82 | 18.78 | 22.18 | 20.04 | 23.86 | 15.29 | 23.33 | 19.95 | 21.63 | 22.71 | 29.87 | 23.28 | 21.05 |
| Median error | 21.00 | 14.00 | 18.00 | 16.00 | 19.00 | 10.00 | 21.50 | 16.00 | 19.00 | 22.00 | 27.00 | 21.50 | 24.00 |
| Num. times best | 5 | 13 | 6 | 24 | 13 | 53 | 2 | 14 | 7 | 4 | 1 | 7 | 2 |
| Num. times worst | 14 | 0 | 8 | 2 | 9 | 1 | 4 | 2 | 7 | 4 | 37 | 11 | 0 |
| Benchmark | Single tree | TreeBoost | Tree forest | SVM | ANN | PNN | GMDH | CCNN | RBF | LDA | K-Means | Linear Reg. | Logistic reg. |

| Principal Components: on Correlations | | | | |
|---|---|---|---|---|
| Number | Eigenvalue | Percent | 20 40 60 80 | Cum Percent |
| 1 | 22.4846 | 72.531 | | 72.531 |
| 2 | 3.2640 | 10.529 | | 83.060 |
| 3 | 1.9099 | 6.161 | | 89.221 |
| 4 | 0.8802 | 2.840 | | 92.061 |
| 5 | 0.5709 | 1.842 | | 93.902 |
| 6 | 0.5406 | 1.744 | | 95.646 |
| 7 | 0.3022 | 0.975 | | 96.621 |
| 8 | 0.2900 | 0.935 | | 97.556 |
| 9 | 0.2025 | 0.653 | | 98.209 |
| 10 | 0.1594 | 0.514 | | 98.724 |
| 11 | 0.1202 | 0.388 | | 99.111 |
| 12 | 0.0910 | 0.294 | | 99.405 |
| 13 | 0.0754 | 0.243 | | 99.648 |
| 14 | 0.0416 | 0.134 | | 99.782 |
| 15 | 0.0256 | 0.083 | | 99.865 |
| 16 | 0.0199 | 0.064 | | 99.929 |
| 17 | 0.0107 | 0.035 | | 99.964 |
| 18 | 0.0063 | 0.020 | | 99.984 |
| 19 | 0.0049 | 0.016 | | 100.000 |

27  LQGD^RRCQSQLERAN

Figure 2:
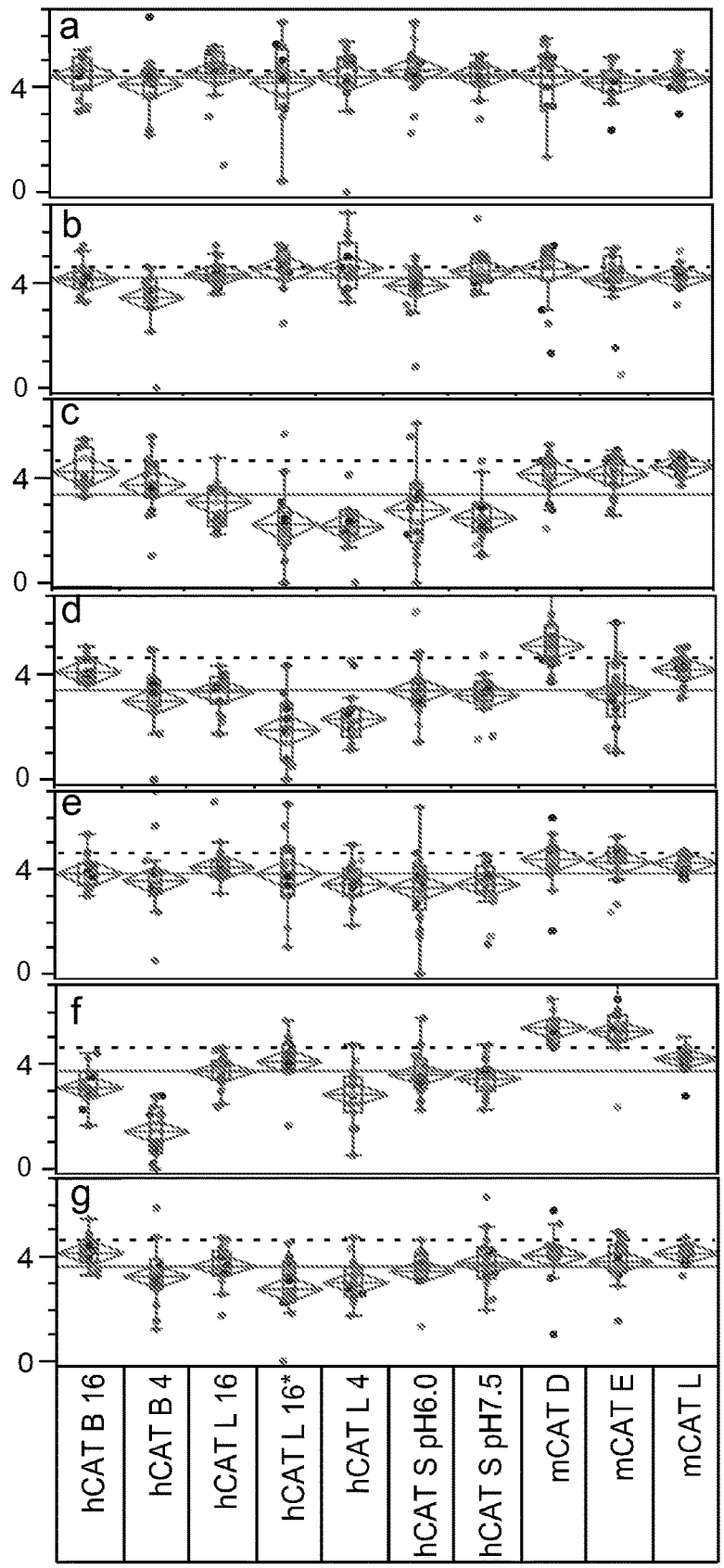

Fig2 A Prickett et al 2010 Peptide

127  QQFK^RELRNLPQQCG

Fig2 C Prickett et al 2010 Peptide

90  RCCN^ELNEFENNQRC

Fig2 B Prickett et al 2010 Peptide

Binding affinity

Standardized Binding Affinity

Figure 24

TTCCCCGACGGGCCCTCCTCGTCCGACCGGCAAAAGATACTGCATCAACTCAGCATCCTTGTCCTTCACTCCTGCAGACCGGCATGGAGGCCGAG (SEQ ID NO: 3)

F P D G P P R P T G K R Y C I N S A S L S F T P A D R M E A E (SEQ ID NO: 4)

BK-RL / 5' murine flank – cath cleavage / RL9 peptide / 3' murine flank – cath cleavage / BK-RL

MATHEMATICAL PROCESSES FOR DETERMINATION OF PEPTIDASE CLEAVAGE

FIELD OF THE INVENTION

This invention relates to the identification of peptidase cleavage sites in proteins and in particular to identification protease cleavage by the endopeptidases.

BACKGROUND OF THE INVENTION

Peptidases perform a wide variety of key functions in biology, ranging from digestion of dietary protein to control of physiologic processes and function of the immune response. Peptidases are present in all life forms including animals and plants, eukaryotes, prokaryotes and viruses. Two broad categories are the exopeptidases and the endopeptidases. Exopeptidases cleave amino acids from the N terminal or C terminal ends of a protein or amino acid sequence. Endopeptidases cleave amino acid sequences internally.

Peptidases are also widely used in manufacturing, including but not limited to wood and leather processing, paper manufacturing, in the detergent industry, textile manufacturing and in the food industry. Proteolytic enzymes account for nearly 60% of the industrial enzyme market in the world. Industrial peptidases may be derived from natural sources or may be synthetic.

Peptidases play a key role in processing and presentation of peptides which stimulate each arm of the immune response. B cell epitopes are released by a peptidase. Proteins are cleaved by peptidase within the endosome to allow short peptides to be released which are then transported to the surface bound by MHC molecules and presented to T cell receptors to stimulate a T cell response. This can result in up-regulation of cytotoxic T cells or T helper cells needed to aid the antibody response, and stimulation of regulatory T cell responses which result in down regulation of the cellular immune response. The position of the cleavage site is critical to determine which peptides are released and hence whether the peptides released have a high binding affinity to a MHC molecules facilitating their traffic and presentation.

While MHC molecules differ between individuals of differing genetics causing a wide variety of immune responses, the peptidase function appears to be relatively constant at least within a particular isotype of a peptidase. Antigen presenting cells such as dendritic cells have a variety of peptidases which contribute to cleavage of proteins and lead to T cell epitope presentation. These enzymes include but are not limited to the cathepsins, including cathepsin L, cathepsin B, cathepsin S. There are species differences between the proteolytic enzymes in dendritic cells and although similar names have been affixed to apparently comparable enzymes based on historical studies, study of their sequences indicates that proteins of similar name designation are not necessarily orthologous.

Protease inhibitors are an important class of medicinal products. Peptidase inhibitors are used to intervene in viral replication in a number of diseases such as HIV AIDs, HCV and others. Protease inhibitors have also been developed to function as metabolic inhibitors in diabetes 2 and other diseases.

It has been a long sought-after goal to be able to predict endopeptidase cleavage. A few endopeptidases have more easily characterizable cleavage sites, such as trypsin which cleaves the bond at the C terminal side of a lysine or an arginine amino acid.

Determinations of cleavage sites have been catalogued, for instance in databases such as Merops. See, e.g., Rawlings, N. D., Barrett, A. J. & Bateman, A. (2012) MEROPS: the database of proteolytic enzymes, their substrates and inhibitors. Nucleic Acids Res 40, D343-D350). The effort to classify endopeptidase cleavage sites has often been based on limited experimental data. Peptidases which provide very specific cleavage of proteins, for instance cathepsins that are active in antigen presentation, have more complex cleavage sites that have challenged researchers.

A recent addition to techniques available for identifying peptidase cleavage sites includes cleavage site labeling (CSL) techniques. See, e.g., Impens F, Colaert N, Helsens K, Ghesquiere B, Timmerman E, et al. (2010) A quantitative proteomics design for systematic identification of protease cleavage events. Mol Cell Proteomics 9: 2327-2333; Tholen S, Biniossek M L, Gessler A L, Muller S, Weisser J, et al. (2011) Contribution of cathepsin L to secretome composition and cleavage pattern of mouse embryonic fibroblasts. Biol Chem 392: 961-971; Biniossek M L, Nagler D K, Becker-Pauly C, Schilling O (2011) Proteomic identification of protease cleavage sites characterizes prime and non-prime specificity of cysteine cathepsins B, L, and S. J Proteome Res 10: 5363-5373. CSL is an accurate but expensive and time consuming process requiring a complex experimental set up with expensive equipment. Each protein must be examined individually for each enzyme.

It would be of great utility to be able to predict from the experimental results obtained with one protein how a given enzyme may cleave other proteins, so that a one or a few experiments using CSL or another experimental approach can provide the basis of a generalizable predictions for a given peptidase which can be applied to any protein of interest whether natural or synthetic to predict the cleavage.

SUMMARY OF THE INVENTION

The present invention provides a mathematical methodology for prediction of peptidase cleavage sites based on principal component analysis and based on training sets obtained by experimental protein cleavage. This invention is not limited to training sets derived from CSL approaches, nor to any other experimental determination of cleavage site. It is also anticipated that there will be new approaches developed for experimental measurement of cleavage sites and these too may be the source of training sets for the present invention.

Accordingly, the present invention is directed to a method for identification in silico of prediction of peptide dimers, cleavage site dimers, which are located centrally within a longer peptide, most commonly but not limited to an octomer, in which the dimer spans a scissile bond and which has a high probability of cleavage by specific peptidases. In some embodiments the peptides that are cleaved may be exogenous to the host (i.e., pathogens. allergens, or synthetic protein biopharmaceuticals); in other embodiments they are endogenous (as in autoimmunity or tumor associated antigens).

In some embodiments the present invention provides processes, preferably computer implemented, for the derivation of ensembles of equations for the prediction of peptidase cleavage. In some embodiments the process comprises generating mathematical expressions based on multiple uncorrelated physical parameters of amino acids, wherein said mathematical expressions serve as descriptors of a peptide. The peptide descriptor is then applied to a set of peptides for which the cleavage site and probability has been experimentally determined. The mathematical descriptors and the experimental data are then compared and a prediction equation derived for cleavage of the scissile bond between each possible pair of amino acids located in the cleavage site dimer positions. In some embodiments the process is then repeated to derive an equation for each possible pair of amino acids in a cleavage site dimer. The assemblage of equations for every possible cleavage site dimer then constitutes an ensemble of predictive equations.

In some embodiments the mathematical expression which is a peptide descriptor is derived by analyzing more than one uncorrelated physical parameters of an amino acid via a computer processor, and constructing a correlation matrix of said physical parameters. In some embodiments this permits the derivation of multiple mutually orthogonal or uncorrelated proxies, wherein said proxies are weighted and ranked to provide descriptors of the amino acids. In further embodiments a number of the proxies which contribute most to the description of the amino acid variability are then selected to serve as descriptors. In some embodiments this number of proxies may be three or more. In some embodiments the proxies are principal components. In further embodiments, by combining the mathematical expression comprising several proxies describing each amino acid in a peptide, a mathematical descriptor for the peptide is derived.

In some embodiments the computer assisted process of assembling an ensemble of equations to predict peptide cleavage requires first deriving a predictive equation for each cleavage site dimer pair of amino acids. By examining a set of peptides for which the cleavage is known, cleavage site dimers are identified which are comprised of identical amino acids but which are located in peptides that are either cleaved or that are uncleaved. A sub set of peptides with these properties is randomly selected. By comparison of the cleaved and uncleaved peptides with the aforesaid peptide descriptors, a first equation is derived to predict cleavage for that cleavage site dimer. This process is repeated on a second random sub set of the peptides and then repeated multiple times, each time expanding the ensemble of equations which can be polled and thus enhancing the precision of the prediction for the particular cleavage site dimer. In some embodiments the derivation of an ensemble of predictive equations is then conducted for other cleavage site dimer amino acid pairs until the maximum of 400 possible pairs has been examined and the corresponding ensembles of predictive equations derived form an ensemble of predictive equations applicable to all potential cleavage site dimers.

In some embodiments the predictive equations are then applied to a protein of interest, wherein the invention provides for inputting the protein of interest into a computer and applying amino acid descriptors based on multiple uncorrelated physical parameters to provide a peptide descriptor for each peptide comprised of a subset of amino acids from within the protein of interest. In some embodiments the process then further comprises applying the peptidase prediction equation ensemble to predict the cleavage site dimers in the peptides from the protein of interest and the probability of cleavage of each cleavage site dimer. In some particular embodiments the probability of cleavage may be 60% or 70% or 80% or 90% or higher.

In some embodiments the peptidase is an endopeptidase. In some embodiments the peptidase is a serine peptidase, in other embodiments the peptidases is a serine peptidase, a cysteine peptidase, an aspartic peptidase, a glutamic peptidase, an asparagine peptidase, a threonine peptidase, or a metallopeptidase.

In some embodiments the peptidase is located within the endosome of a cell. In some instances said cell is an antigen presenting cell. In some embodiments the cell is a dendritic cell, in other embodiments it is a B cell, and in yet further embodiments it is a macrophage.

The present invention provides for methods to predict cleavage by peptidases, including mammalian peptides such as human and mouse peptidases. These examples are not limiting and the invention described is equally applicable to analysis of cleavages by peptidases of other eukaryotic or prokaryotic species or to synthetically engineered peptidases upon provision of relevant training sets for that enzyme. The training sets may be derived from many experimental techniques known to those skilled in the art, including but not limited to cleavage site labeling.

In some instances, the peptide which defines the context of the cleavage site is an octomer, designated the cleavage site octomer (CSO). In other instances the peptide which defines the context of a cleavage site may comprise fewer or greater numbers of amino acids. Based on the work of Schechter & Berger to describe the specificity of papain and crystallographic structures of peptidases the active site of a peptidase enzyme is commonly located in a groove on the surface of the molecule between adjacent structural domains, and the peptide substrate specificity is dictated by the properties of binding sites arranged along the groove on one or both sides of the catalytic site that is responsible for hydrolysis of the scissile bond. See, e.g., Schechter, I. & Berger, A. On the size of the active site in proteases. I. Papain. Biochem. Biophys. Res. Commun. 27, 157-162 (1967). Accordingly, the specificity of a peptidase is described by use of a conceptual model in which each specificity subsite is able to accommodate the sidechain of a single amino acid residue. The sites are numbered from the catalytic site, S1, S2 . . . Sn towards the N-terminus of the substrate, and S1', S2' . . . Sn' towards the C-terminus. The residues they accommodate are numbered P1, P2 . . . Pn, and P1', P2' . . . Pn', respectively, as follows:

Substrate: -P4 P3-P2-P1~P1'-P2'-P3' P4'-
Enzyme: S4-S3-S2-S1*S1'-S2'-S3' S4'

In some embodiments the scissile bond is located between two amino acids P1 and P1' designated as the cleavage site dimer.

In some embodiments, the analyzing physical parameters of subsets of amino acids comprises replacing alphabetical coding of individual amino acids in the subset with mathematical expressions. In some embodiments, the physical properties or physical parameters are represented by one or more principal components. In some embodiments, the physical parameters are represented by at least three principal components or 3, 4, 5, or 6 principal components. In some embodiments, the letter code for each amino acid in the subset is transformed to at least one mathematical expression. In some embodiments, the mathematical expression is derived from principal component analysis of amino acid physical properties. In some embodiments, the letter code for each amino acid in the subset is transformed to a three number representation. In some embodiments said principal components are mutually uncorrelated, or orthogonal. In some embodiments, the principal components are weighted and ranked proxies for the physical properties of the amino acids in the subset. In some embodiments, the physical properties are selected from the group consisting of polarity, optimized matching hydrophobicity, hydropathicity, hydropathcity expressed as free energy of transfer to surface in kcal/mole, hydrophobicity scale based on free energy of transfer in kcal/mole, hydrophobicity expressed as $\Delta G \frac{1}{2}$ cal, hydrophobicity scale derived from 3D data, hydrophobicity scale represented as $\pi-r$, molar fraction of buried residues, proportion of residues 95% buried, free energy of transfer from inside to outside of a globular protein, hydration potential in kcal/mol, membrane buried helix parameter, mean fractional area loss, average area buried on transfer from standard state to folded protein, molar fraction of accessible residues, hydrophilicity, normalized consensus hydrophobicity scale, average surrounding hydrophobicity, hydrophobicity of physiological L-amino acids, hydrophobicity scale represented as $(\pi-r)^2$, retention coefficient in HFBA, retention coefficient in HPLC pH 2.1, hydrophobicity scale derived from HPLC peptide retention times, hydrophobicity indices at pH 7.5 determined by HPLC, retention coefficient in TFA, retention coefficient in HPLC pH 7.4, hydrophobicity indices at pH 3.4 determined by HPLC, mobilities of amino acids on chromatography paper, hydrophobic constants derived from HPLC peptide retention times, and combinations thereof. In some embodiments, the physical properties are predictive of the property of the peptides which comprise the cleavage site of a peptidase.

In some embodiments the process comprises application of a classifier. Examples of classifiers include but are not limited to neural nets and support vector machines. In preferred embodiments the classifier is a probabilistic classifier. In some embodiments, the processes comprises applying a classifier via the computer, wherein the classifier is used to predict the peptide which spans the scissile bond of a peptidase and the location of said cleavage site. In some embodiments, the classifier provides a quantitative structure activity relationship. In some embodiments, the first three principal components represent more than 80% of physical properties of an amino acid.

In some embodiments, the classifier is a neural network and the processes further comprise constructing a multi-layer perceptron neural network regression process wherein the output is the probability of cleavage at a given bond within a particular peptide or amino acid subset, surrounding a peptidase cleavage site. In preferred embodiments said amino acid subset is an octomer. In some embodiments, the regression process produces a series of equations that allow prediction of the cleavage site using the physical properties of the subsets of amino acids. In some embodiments, the processes further comprise utilizing a number of hidden nodes in the multi-layer perceptron that correlates to the eight amino acids in the cleavage site octomer. In other embodiments a neural net of more or less hidden nodes may be used. In some embodiments, the neural network is validated with a training set of cleavage sites within peptides of known amino acid sequence. In some embodiments such training sets are derived from the experimental results of output from CSL procedures. See, e.g., Impens et al., Tholen et al., and Biniossek et al., referenced above. Other sources of training sets which provide experimental data on the site of peptidase cleavage may be applied and so the source of training set is not limiting. In yet other embodiments the classifier comprises application of a support vector machine. See, e.g., Cortes C, Vapnik V (1995) Support-vector network. Mach Learn 20: 1-25; Scholkopf B, Smola A J, Williamson R C, Bartlett P L (2000) New support vector algorithms. Neural Comput 12: 1207-1245; Bennett K P, Campbell C (2000) Support vector machines: Hype or Hallelujah? SIGKDD Explorations 2. Other types of classifiers may be applied.

In some embodiments, the amino acid sequence comprises the amino acid sequences of a class of proteins selected from the group derived from the proteome of pathogenic microorganisms. In other embodiments the amino acid sequences derive from a class of proteins selected from the group comprising allergens (including but not limited to plant allergen proteins and food allergens). In other embodiments the amino acid sequences derive from a class of proteins selected from the group comprising mammalian proteins including but not limited to tumor associated antigen proteins, proteins reactive in autoimmunity, immunoglobulins, enzymes and structural mammalian proteins. In other embodiments the amino acid sequences derive from a class of proteins selected from the group comprising synthetic and recombinantly manufactured proteins, including but not limited to biopharmaceuticals (e.g., replacement enzymes, clotting factors, monoclonal antibodies and antibody fusions) and industrial proteins (for example in food additives, textiles, wood). These examples however should not be considered limiting as the analytical approach can be applied to any peptidase of any species or source provided training sets can be developed experimentally by any means for that enzyme. Furthermore the predictions of cleavage by any selected peptidase may then be applied to proteins of any source.

In some embodiments, at least 80% of possible amino acid subsets within a protein are analyzed for predicted cleavage sites. In further embodiments all the proteins within an organism may be analyzed, with at least 80% of possible amino acid subsets in each protein being analyzed. In other embodiments all the proteins within a natural tissue (e.g., muscle) or within a composite industrial product (e.g., paper) may be analyzed to determine predicted cleavage sites.

In some embodiments determination of the cleavage site is used in selecting a peptide for inclusion in an immunogen or vaccine, such that the immunogen will be cleaved predictably for binding by an MHC molecule and presentation at the cell surface to a T cell receptor and hence stimulate immunity, or such that a B cell epitope is bound to a B cell receptor and internalized by the B cell. In some embodiments said immunogenic peptide is selected to provide a cleavage site 4, or 5 or 6 or up to 20 amino acids from the N terminal or the C terminal of the selected peptide. In some embodiments the peptide is selected such that the predicted cleavage site is separated from the immunogenic peptide by flanking regions of 1, or 2 or 3 or up to 20 amino acids.

In some embodiments an amino acid sequence is analyzed to determine the cleavage sites for one specific peptidase. In other embodiments the amino acid sequence is analyzed to predict the cleavage sites of 2 or 3 or 4 or more peptidase enzymes acting in sequence. In further embodiments the sequence of action of the peptidases may be varied.

In some embodiments, the present invention provides a computer system or computer readable medium comprising a neural network that determines peptidase cleavage sites within an amino acid sequence.

In some embodiments, the present invention provides a computer system configured to provide an output comprising a graphical representation of the location of the cleavage sites within an amino acid sequence, wherein the amino acid sequence forms one axis and the cleavage sites of one or more peptidases are charted against the amino acid sequence axis.

In some embodiments, the present invention provides a synthetic polypeptide wherein amino acids flanking a high affinity MHC binding peptide have been substituted to change (e.g., increase or reduce) the probability of cathepsin cleavage. In some embodiments, the change is an increase in the probability of cleavage. In some embodiments, the change is a decrease in the probability of cleavage. In some embodiments, 2, 3, or 4 amino acids have been substituted to change the probability of cathepsin cleavage. In some embodiments, the amino acids which are substituted are located at the C terminal of a high affinity MHC binding peptide. In some embodiments, the amino acids which are substituted are located at the N terminal of a high affinity MHC binding peptide. In some embodiments, the probability of cathepsin cleavage is changed by at least 2 fold (e.g., increased or decreased by 100%). In some embodiments, the probability of cathepsin L cleavage is changed. In some embodiments, the probability of cathepsin S cleavage is changed. In some embodiments, the probability of cathepsin B cleavage is changed. In some embodiments, the peptide comprises one or more MHC binding peptides and a B cell binding peptide. In some embodiments, the peptide is an immunogen. In some embodiments the amino acids which are substituted lie within 1-10 amino acid positions of the N terminal of a MHC binding peptide, in yet other embodiments said amino acids which are substituted lie within 1-10 amino acids of the C terminal of an MHC binding peptide.

DESCRIPTION OF THE FIGURES

FIG. 1. Differences between the mean z-scale vector of cleaved and uncleaved peptides that are P1-anchored. Data is from a series of training set cohorts each consisting of N cleaved peptides and 4N random, uncleaved peptides with matching amino acids at the P1 position. The differential in the first principal component $z_1$ (polarity/hydrophobicity related) and the second principal component $z_2$ (size related) is defined as (Mean $PC_{(cleaved\ set)}$—Mean $PC_{(random\ set)}$). An individual colored line is plotted for each amino acid that is found in the P1 position in the active cleavage site octomer. Panel a) Human cathepsin L $z_1$—alanine anchor highlighted; b) Murine cathepsin L—alanine anchor highlighted; c) Human cathepsin L $z_2$—alanine anchor highlighted; d) Murine cathepsin L—alanine anchor highlighted. Alanine is selected to be highlighted only because it is the first in the alphabetic list.

FIG. 2. Variation in the dispersion of the underlying principal components of the amino acids (z-scale vectors) is shown at each position in the cleavage site octomer (CSO) for different cathepsins under several experimental conditions. As in FIG. 1, each peptide set is anchored by matched amino acids at the P1 position in the CSO. The green diamond symbols plot the mean and the confidence limits of the standard deviations of the cleaved sets of peptides for each position in the CSO. The extremes of the boxes are the $25^{th}$ and $75^{th}$quantile and the extremes of the red lines are the $10^{th}$ and $90^{th}$ percentile. The dashed line is plotted at the −2 sigma line (i.e. $95^{th}$ percentile confidence) of the random, uncleaved cohort set and is constant at all positions for all proteases. a) P4; b) P3; c) P2; d) P1'; e) P2'; f) P3'; g) P4'. The solid line is the overall mean. Datasets used were from references indicated in the text. hCAT B=Human cathepsin B digested for 4 or 16 hrs; hCAT L=Human cathepsin L digested for 4 or 16 hrs; hCAT L16* Human cathepsin L digested for 16 hrs using a different peptide library as substrate. mCAT D, E, L=murine cathepsins results obtained as described in source references.

FIG. 3. Shape of the unit-integral weighting function used for regression fitting is shown for several different weighting factors. [1] (blue)=uniform {pattern=1, 1, 1, 1, 1, 1, 1, 1, Σ=} principal component values used; [2] (red)={pattern=1, 2, 4, 8, 8, 4, 2, 1, Σ=3} multiplier applied; [3] (green)={pattern=1, 1.5, 2.25, 3.375, 3.375, 2.25, 1.5, 1, Σ=16.25} multiplier applied; [4] (purple)={pattern=1, 1.25, 1.5625, 1.953125, 1.953125, 1.5625, 1.25, 1, Σ=11.53125} multiplier applied to all three principal components used as predictors. All multipliers were normalized to the Σ to prevent scaling effects in the predictions.

FIG. 4. Sensitivity and specificity patterns for cleavage predictions for human cathepsin L (16 hr time point) is shown in a layout of a standard contingency table or confusion matrix format. a) TN=true negative; b) FP=false positive; c) FN=false negative; d) TP=true positive cleavage predictions. The inset 'shadowgrams' are a histogram-like graphic where a large number (all training and validation cohorts with all weighting factors) of partially transparent distribution kernels are overlayed and thereby simultaneously build up a pattern and density. The vertical axis is probability of that particular classification and the inset is the standard mean, median and quantiles of the underlying distributions. For the 'heat diagrams' the predictions are segregated by the P1 anchor residue and are centered (gray) on the overall mean of the four data columns. The 'thermometers' are scales of the associated probabilities. Each column represents the results obtained using a different weighting factor. Two-way clusters are formed by the method of Ward. Ward, J. H. Hierarchical Grouping to Optimize an Objective Function. J. Am. Stat. Assoc. 48, 236-244 (1963).

FIG. 5. Impact of using a dual amino acid anchor (P1-P1') as compared to a single P1 anchor for prediction of murine cathepsin E. Description of heat diagrams as in FIG. 4. a) Sensitivity (TP/(TP+FN)) of the predictor output using a single amino acid anchor at P1. b) and d) Sensitivity using P1-P1' pair anchors indicated. The numbers in parenthesis are the number of cleavage events with the particular P1-P1' pair. c) and e) FN/(TP+FN) as in b) and d).

FIG. 6. Predicted endosomal protease cleavage of myelin basic protein compared with experimental determinations. a) murine cathepsin L; b) murine cathepsin E, c) murine cathepsin D, d) human cathepsin B; e) human cathepsin S; f) human cathepsin L. Beck, H. et al. Cathepsin S and an asparagine-specific endoprotease dominate the proteolytic processing of human myelin basic protein in vitro. Eur. J. Immunol. 31, 3726-3736 (2001). The amino acid index in the full sequence of (GI 17378805; P02686) is used. The predicted cleavages are consolidated for all predictors anchored at both P1 and P1' amino acids as described in the text. The peptide sequence insets are at critical degradative cleavage positions (number) described by Beck et al and are centered at the P1-P1' cleavage point (~) in the panel of the protease of relevance indicated in the reference.

FIG. 7. Artificial neural network perceptron topology. The perceptron used for prediction of cleavage has 3 layers: an input layer consisting of the vectors of the first three principal components of the amino acids in the octomer binding site; a hidden layer consisting of 8 nodes with symmetry to the octomer binding site; and a single output layer which is the cleavage prediction. An hyperbolic tangent activation function was used for all interconnections within the perceptron structure.

FIG. 8. Data flow.

FIG. 9. Frequency pattern logos (produced by weblogo.berkeley.edu) of peptides with matching P1-P1' in the CSO for two prevalent cleavage patterns in murine Cathepsins D and E. a) Murine Cathepsin D, 340 random uncleaved; b) Murine Cathepsin D, 34 cleaved peptides; c) Murine Cathepsin E, 660 random uncleaved; and d) Murine Cathepsin E, 66 cleaved; Indices at the bottom are the standard amino acid positions in the CSO.

Figure 10:
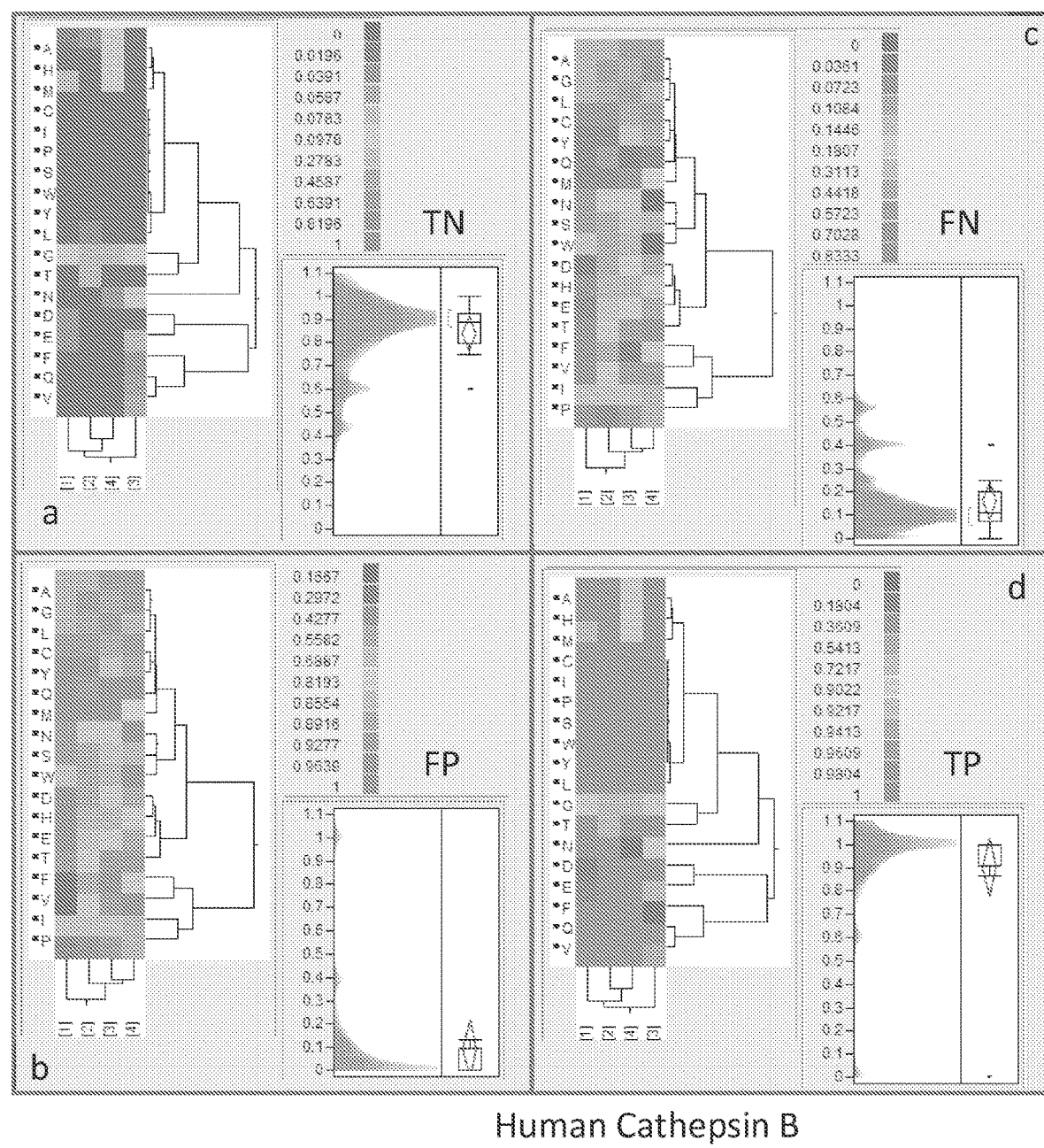

FIG. 10. Sensitivity and specificity patterns for human cathepsin B cleavage predictions is shown in a layout of a standard contingency table or confusion matrix format. a) TN=true negative; b) FP=false positive; c) FN=false negative; d) TP=true positive cleavage predictions. The inset 'shadowgrams' are a histogram-like graphic where a large number (all training and validation cohorts with all weighting factors) of partially transparent distribution kernels are overlayed and thereby simultaneously build up a pattern and density. The vertical axis is probability of that particular classification and the inset is the standard mean, median and quantiles of the underlying distributions. For the 'heat diagrams' the predictions are segregated by the P1 anchor residue and are centered (gray) on the overall mean of the four data columns. The associated 'thermometers' are the associated probabilities. Each column represents the results obtained using a different weighting factor. Two-way clusters are formed by the method of Ward.

Figure 11:
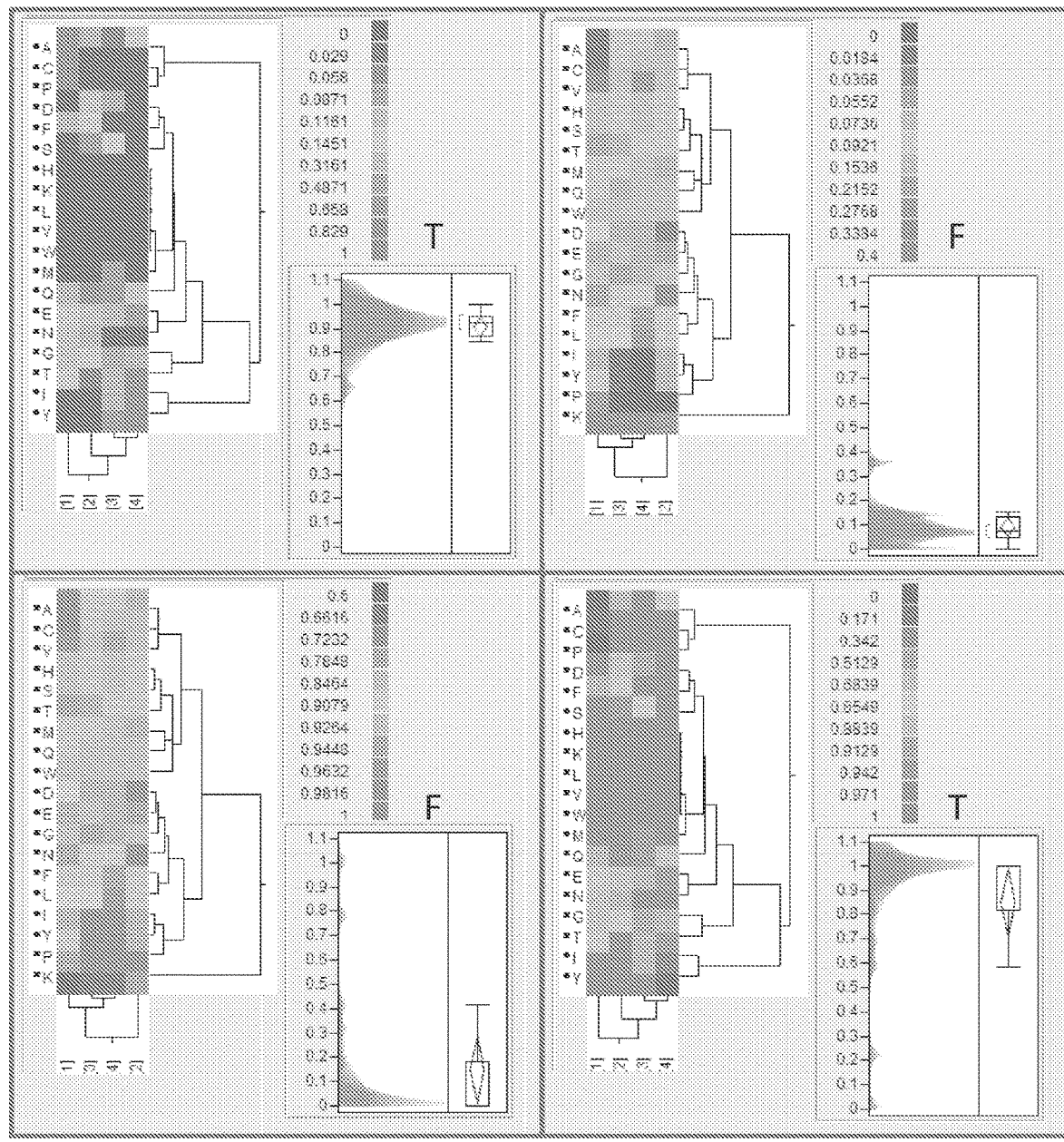

FIG. 11. Sensitivity and specificity patterns for human cathepsin S at pH 7.5 cleavage predictions is shown in a layout of a standard contingency table or confusion matrix format. a) TN=true negative; b) F=false positive; c) FN=false negative; d) TP=true positive cleavage predictions. The inset 'shadowgrams' are a histogram-like graphic where a large number (all training and validation cohorts with all weighting factors) of partially transparent distribution kernels are overlayed and thereby simultaneously build up a pattern and density. The vertical axis is probability of that particular classification and the inset is the standard mean, median and quantiles of the underlying distributions. For the 'heat diagrams' the predictions are segregated by the P1 anchor residue and are centered (gray) on the overall mean of the four data columns. The associated 'thermometers' are the associated probabilities. Each column represents the results obtained using a different weighting factor. Two-way clusters are formed by the method of Ward.

FIGS. 12a, b, and c. Comparison of performance of different predictors with different benchmark datasets. Downloaded from dtreg.com/benchmarks.htm.

Figure 13:
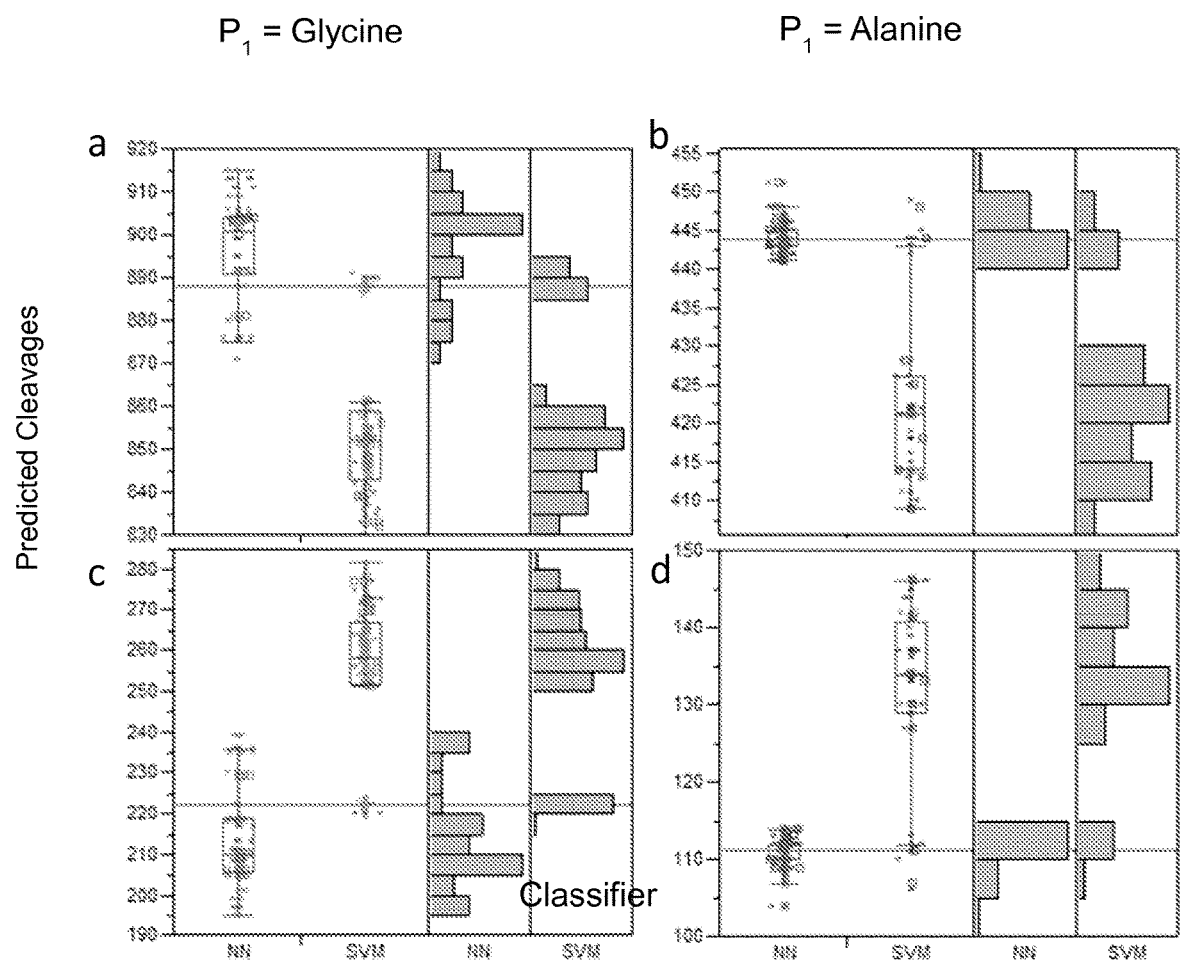

FIG. 13. Comparison of the performance of a probabilistic neural network (NN) and a support vector machine (SVM) as binary classifiers for predicting cleavage of human cathepsin L. The cleavage site octomers in the peptide training sets had either an alanine or a glycine at position $P_1$. (a) and (c) Glycine at $P_1$. Total of the cleaved trainer peptides was 222 (indicated by the blue horizontal line). Cleaved peptides were paired for training with 5 un-cleaved random cohorts with 888 peptides in each set (indicated by red horizontal line). (b) and (d) alanine at $P_1$. Total of the cleaved trainer peptides was 111 (blue horizontal line). Cleaved peptides were paired for training with 5 un-cleaved random cohorts with 444 peptides in each set (red horizontal line).

Figure 14:
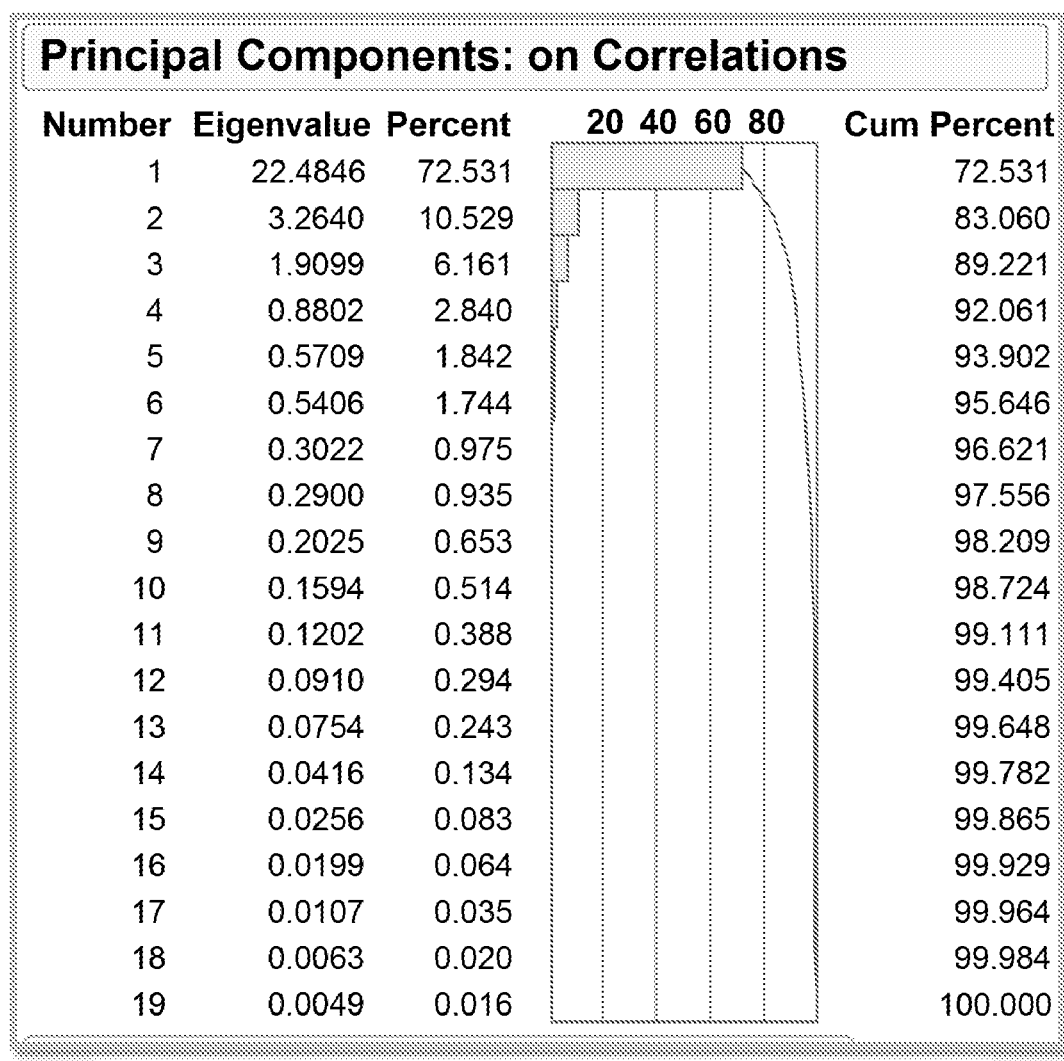

FIG. 14 provides principal components on the correlations of various physicochemical properties of amino acids from 31 different studies.

Figure 15:
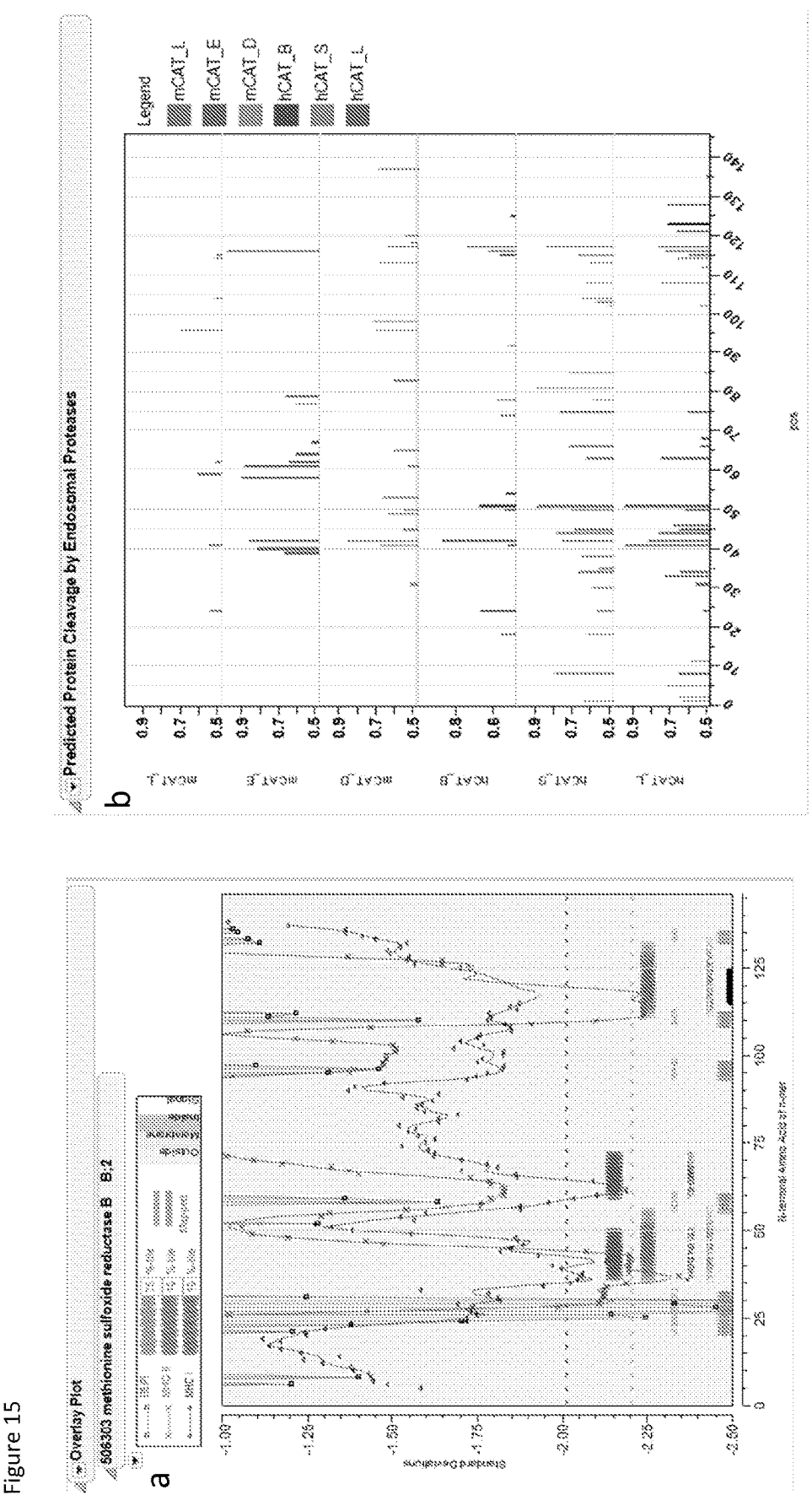
Figure 15:
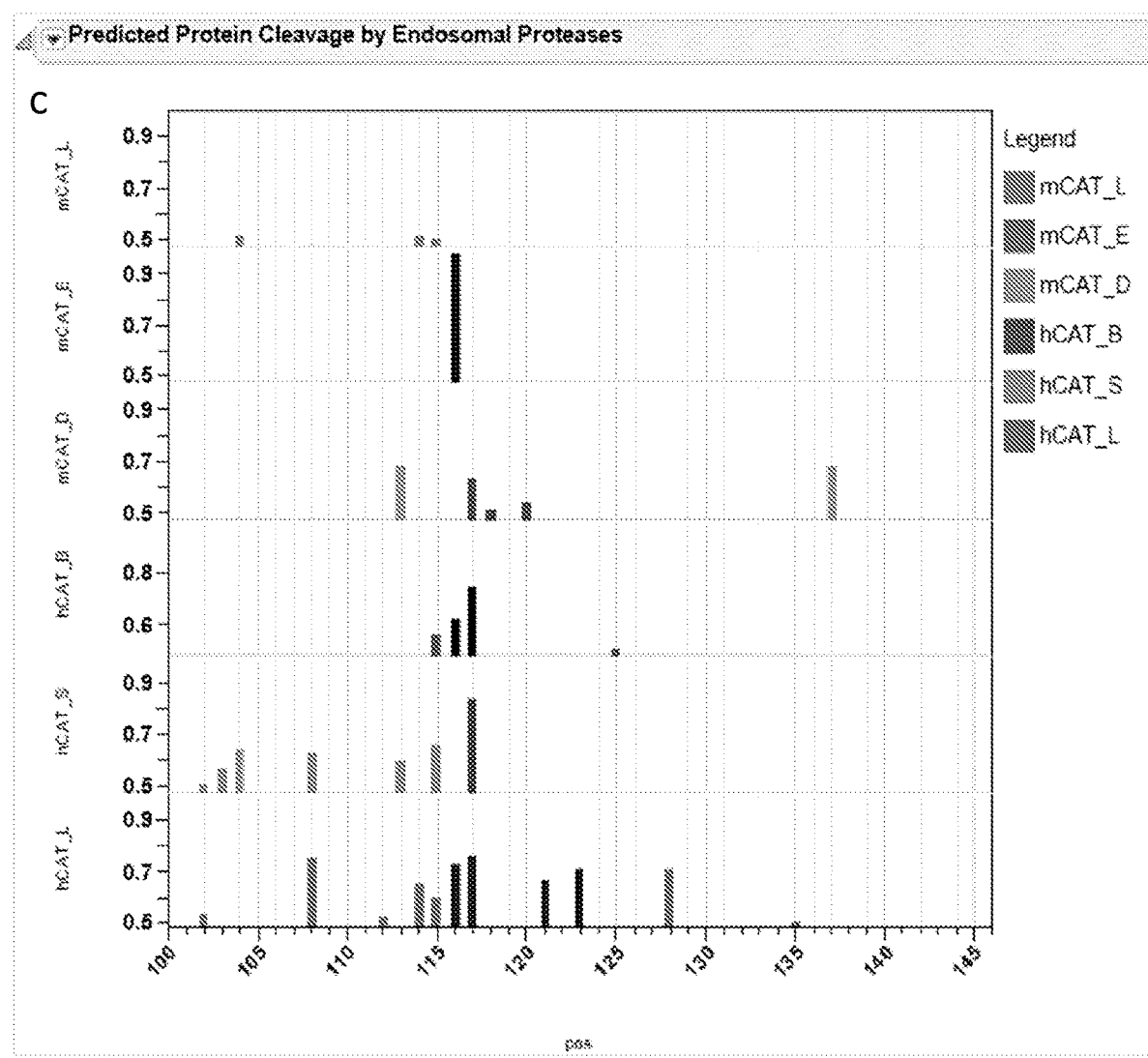

FIG. 15. Predicted peptidase cleavage sites in a *Brucella melitensis* protein. A. Shows the population permuted plot of predicted MHC binding for *Brucella melitensis* methionine sulphoxide reductase B. The peptide marked in black (RYCINSASL (SEQ ID NO: 7)) was identified by Durward et al (Durward, M. A., Harms, J., Magnani, D. M., Eskra, L., & Splitter, G. A. Discordant *Brucella melitensis* antigens yield cognate CD8+ T cells in vivo. *Infect. Immun.* 78, 168-176 (2010)) as capable of inducing a CD8+ cytoxic response in mice. B. Shows predicted probability of cleavage in this protein by human cathepsins L, S and B and murine cathepsins D, E and L. C. is an expansion of a section of the plot shown in B. Each bar is indexed at the start of a cleavage site octomer and hence indicates the probability of cleavage at the bond 4 amino acids to the right (towards C terminus). The darker colored bars show that there is a high probability of cleavage either side of the peptide of interest located at positions 116-124.

Figure 16:
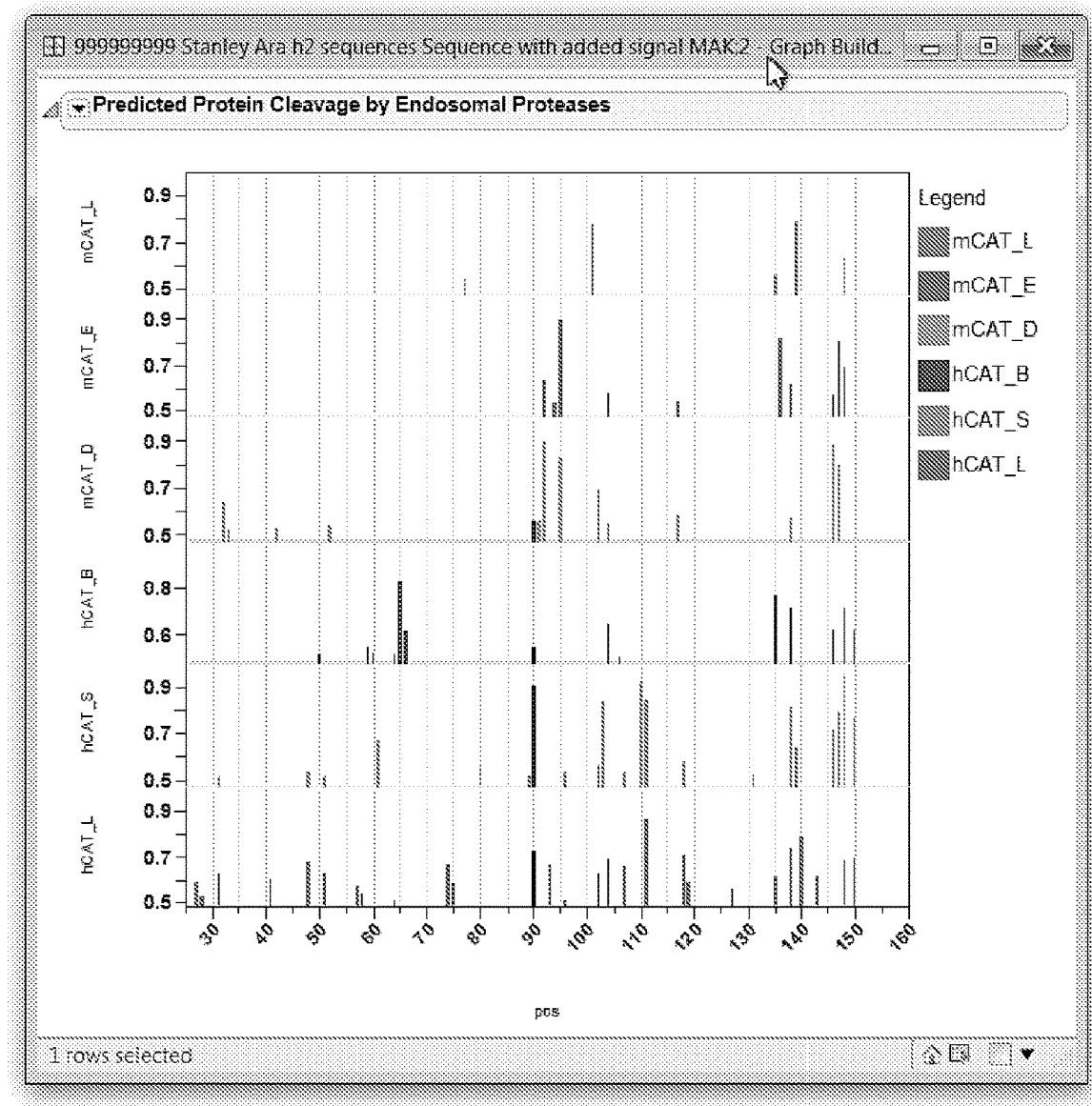

FIG. 16: Peptidase cleavage sites predicted in AraH2 isoform 1 (GI_224747150). Noted below are the locations of the cleavages relative to peptides identified experimentally by Prickett et al as dominant CD4+ eptiopes.

Figure 17:
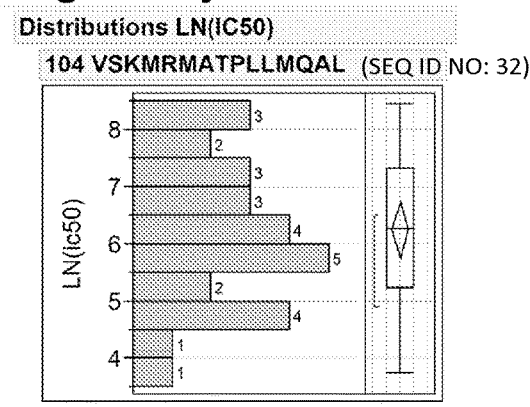
Figure 17:
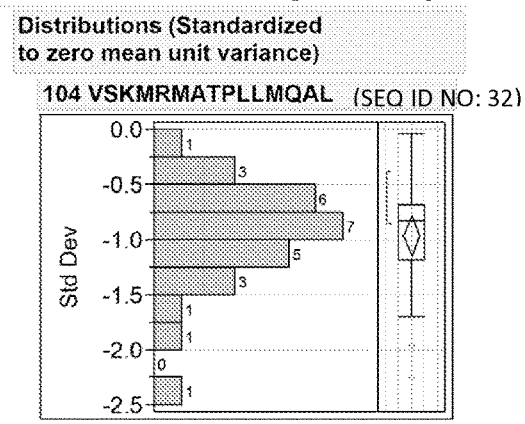

FIG. 17. Statistical characteristic of the primary CLIP peptide in the context of a canonical 15-mer for 28 human MHC II alleles. CLIP peptide binds to many different MHC II molecules with a moderate affinity of about e6.26=525 nM equivalent to about −0.96σ (approx −1σ) below the mean.

Figure 18:
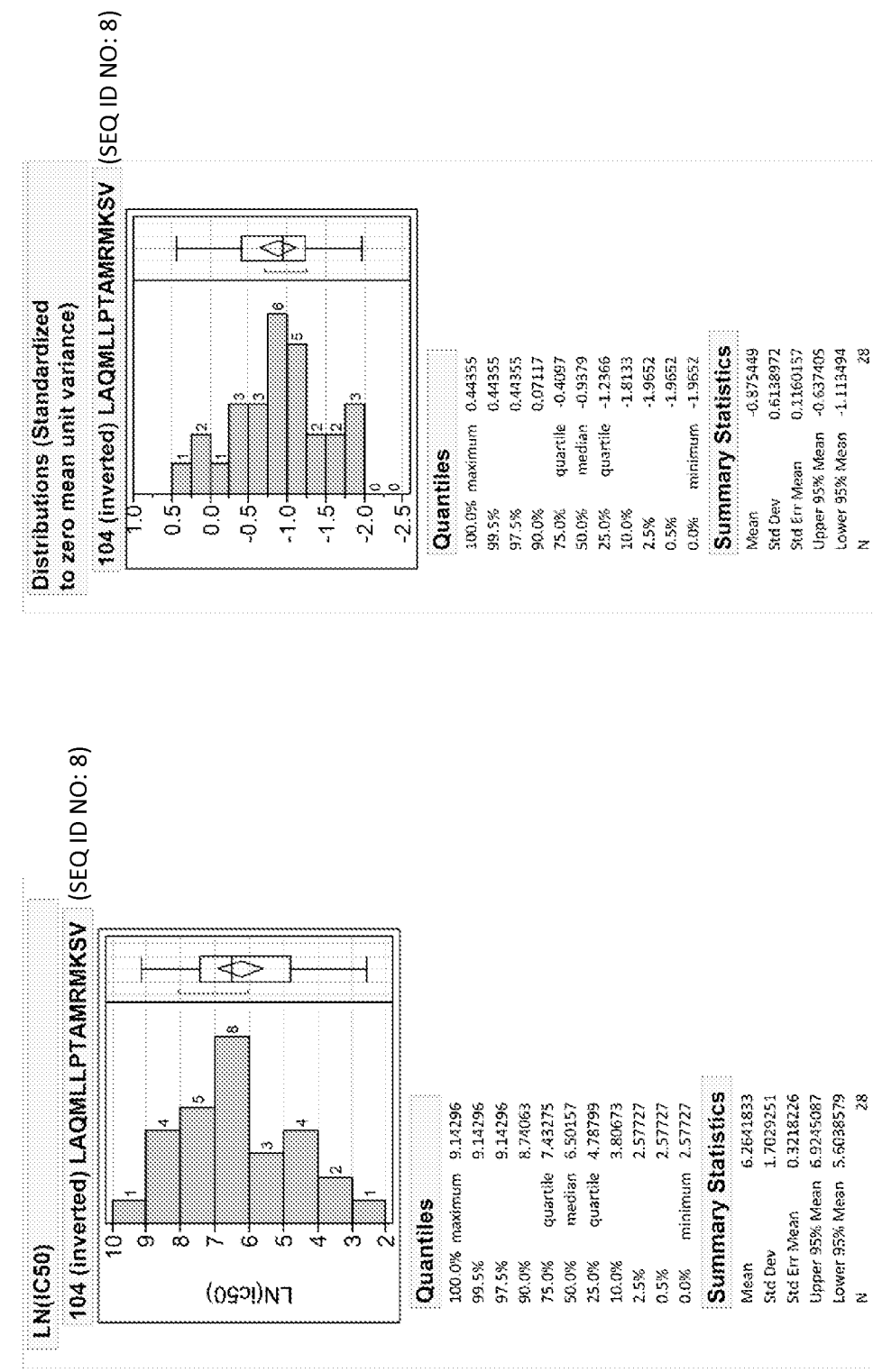

FIG. 18. Statistical characteristic of the inverted CLIP peptide in the context of an inverted (non-canonical) 15-mer for 28 human MHC II alleles.

Figure 19:
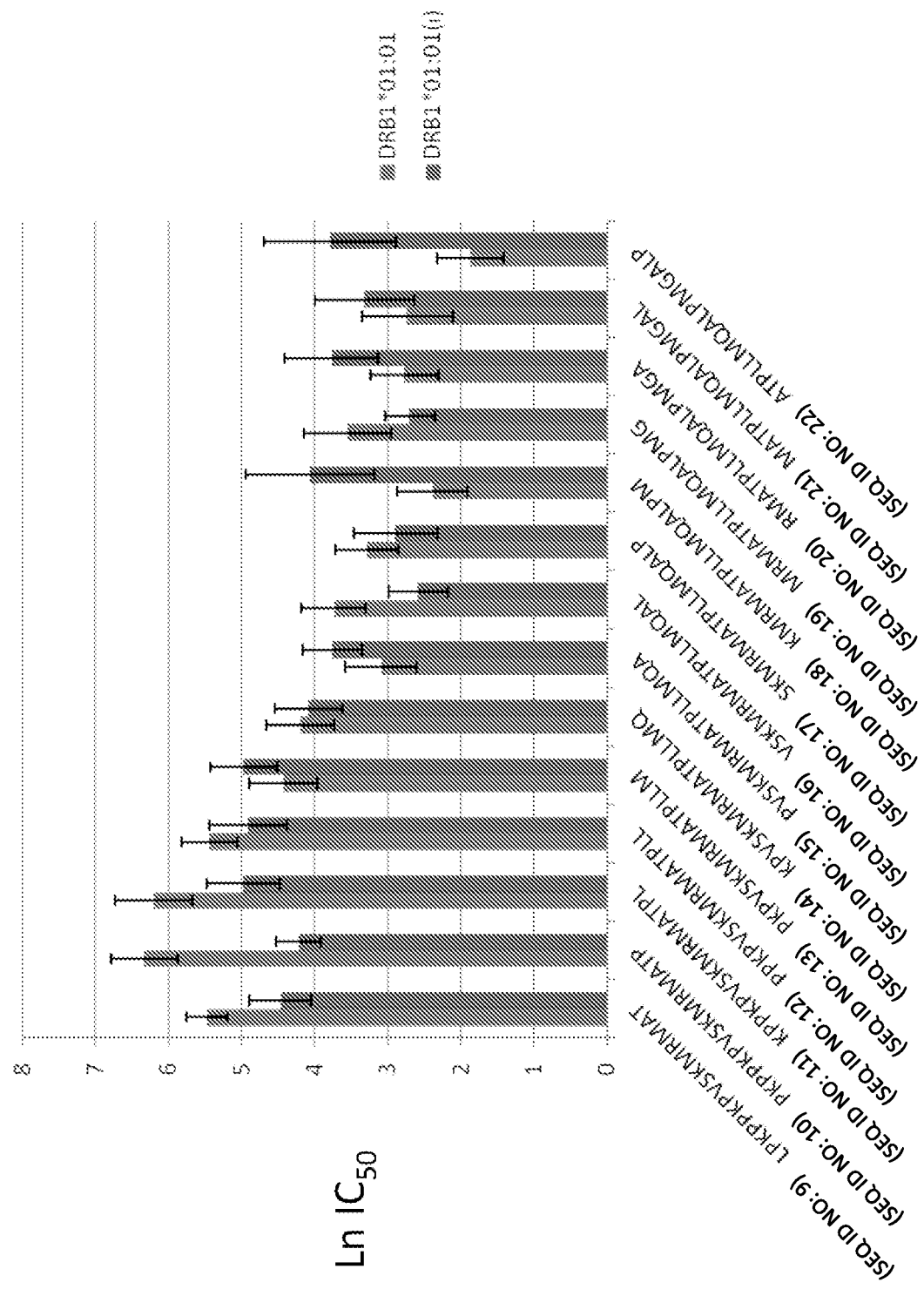

FIG. 19. Predicted MHC affinity for CLIP peptide in either the canonical orientation or the reverse orientation in binding groove DR1 (DRB1*01:01).

Figure 20:
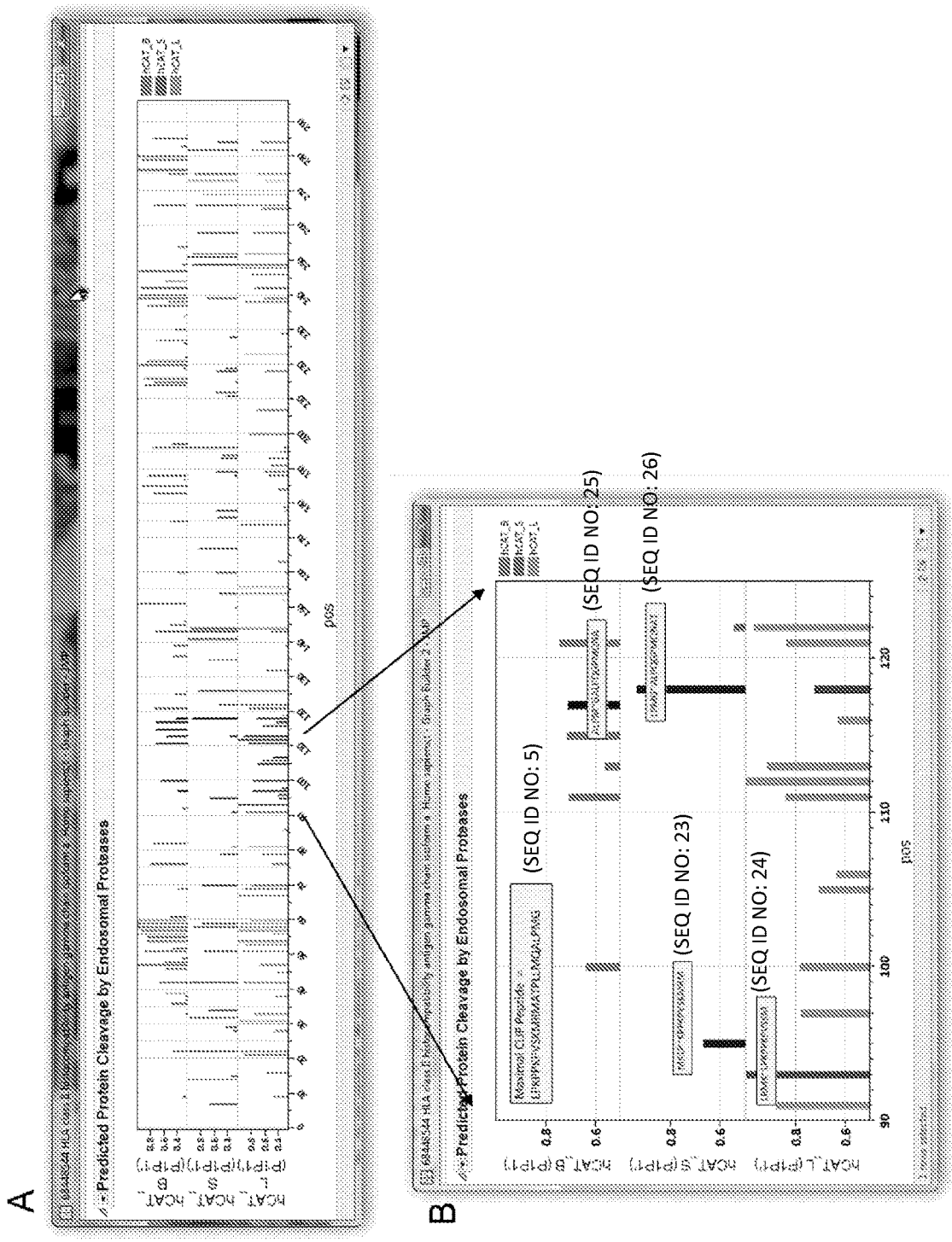

FIG. 20. Probability of cleavage by cathepsin B, S, L in HLA class II histocompatability antigen isoform A. Panel A shows the proability of cathepsin cleavage along the whole protein. Panel B expands the detail for amino acid positions 90-120. Highlighted (darker color bars) cleavage points are high yield promiscuous self peptides reported by Chicz et al 1993 (see Table 6 in reference) and shown in the inserted labels.

Figure 21:
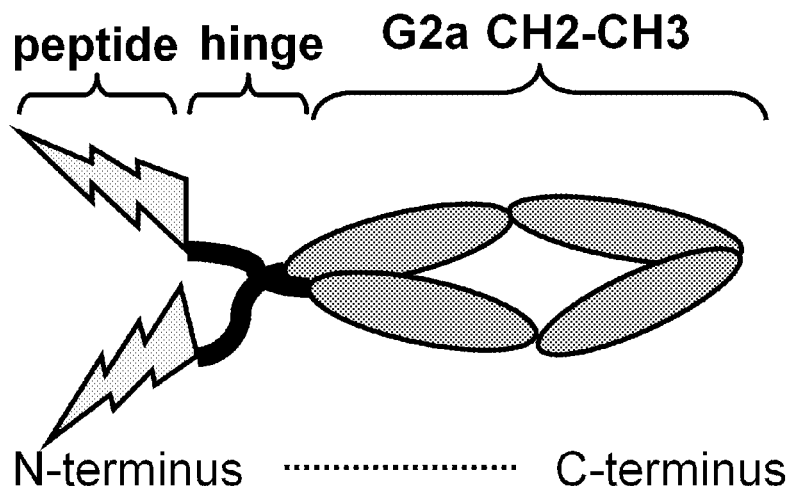

FIG. 21. Construct comprising an epitope peptide of interest at the N-terminus, the hinge region and the constant regions CH2 and CH3 from the murine IgG2a immunoglobulin. The molecule dimerizes via formation of disulphide bonds at the hinge.

Figure 22:
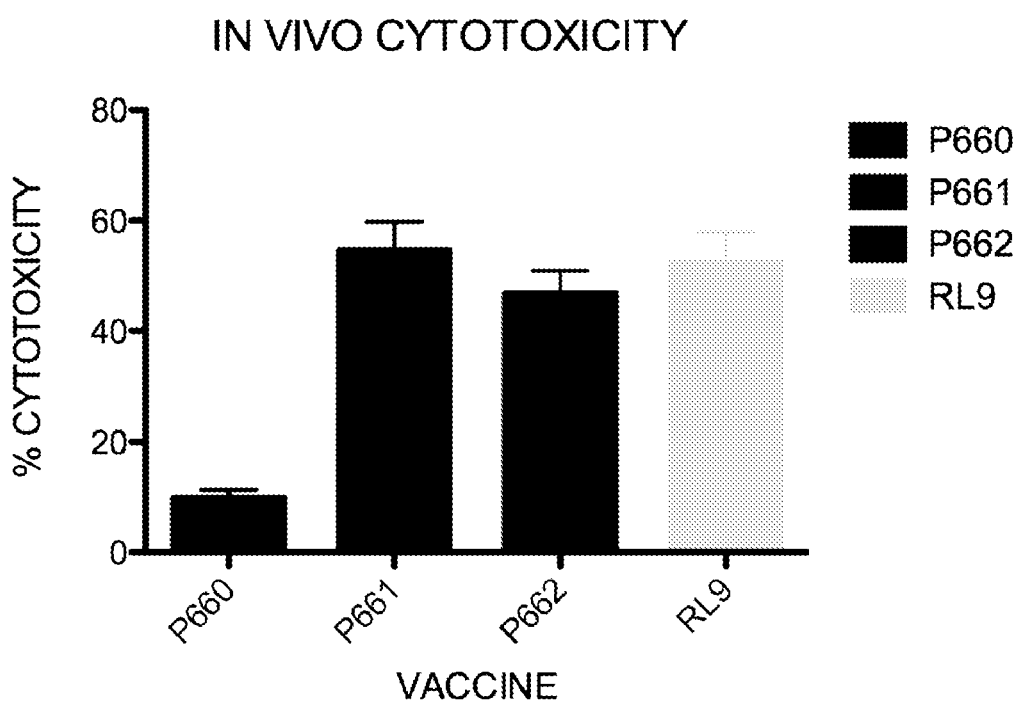

FIG. 22. In vivo clearance of RL9 pulsed splenocytes in immunized mice. Mice were immunized and boosted once with affinity-purified RL-G2a(CH2-CH3) (P661) or RL-G2a (CH2-CH3)-RL (P662) or synthetic peptide RL9. One week after the boost, RL9-pulsed (labeled CFSEhi) and unpulsed (labeled CFSElo) splenocytes from naïve mice were adoptively transferred into the immunized mice via retrobulbar injection. Six hours post transfer, spleens were removed from immunized mice and analyzed for surviving pulsed, labeled target cells using flow cytometry. % specific lysis=1−[rnaive/rvaccinated]×100; where r=% CFSELo cells÷% CFSEHi cells. P660=immunized with isotype-matching, irrelevant antibody.

Figure 23:
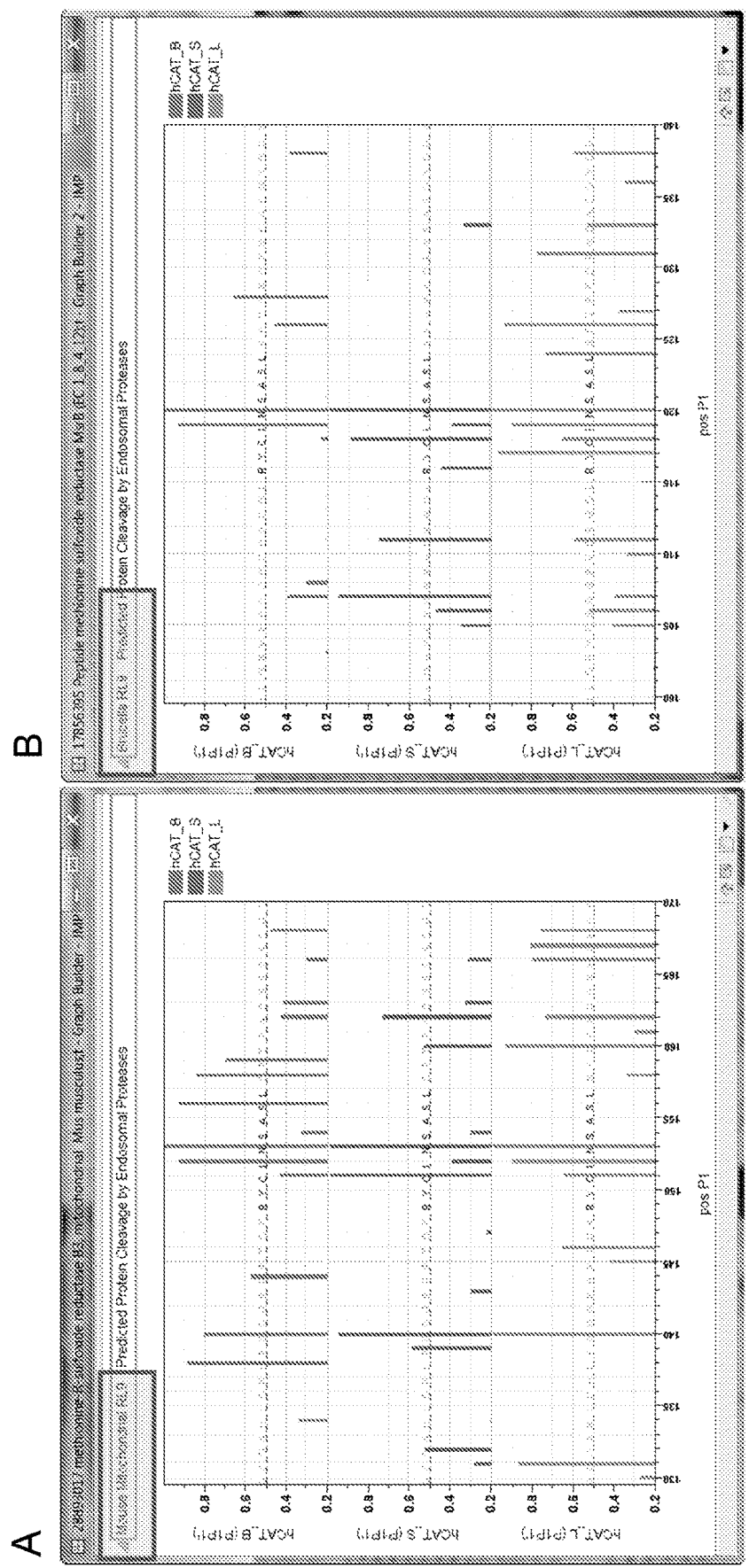

FIG. 23. Probability of cathepsin cleavage in methionine sulphoxide reductase B. Panel A shows the predicted cleavage of murine methionine sulphoxide reductase B. Panel B shows the probability of cleavage of *Brucella melitensis* methionine sulphoxide reductase B. In both panels the 9 mer peptide of interest RYCINSASL (SEQ ID NO: 7) is shown.

FIG. 24. Altered flanking regions of RL9 peptide.

DEFINITIONS

As used herein "peptidase" refers to an enzyme which cleaves a protein or peptide. The term peptidase may be used interchangeably with protease, proteinases, oligopeptidases, and proteolytic enzymes. Peptidases may be endopeptidases (endoproteases), or exopeptidases (exoproteases). Similarly the term peptidase inhibitor may be used interchangeably with protease inhibitor or inhibitor of any of the other alternate terms for peptidase.

As used herein, the term "exopeptidase" refers to a peptidase that requires a free N-terminal amino group, C-terminal carboxyl group or both, and hydrolyses a bond not more than three residues from the terminus. The exopeptidases are further divided into aminopeptidases, carboxypeptidases, dipeptidyl-peptidases, peptidyl-dipeptidases, tripeptidyl-peptidases and dipeptidases.

As used herein, the term "endopeptidase" refers to a peptidase that hydrolyses internal, alpha-peptide bonds in a polypeptide chain, tending to act away from the N-terminus or C-terminus. Examples of endopeptidases are chymotrypsin, pepsin, papain and cathepsins. A very few endopeptidases act a fixed distance from one terminus of the substrate, an example being mitochondrial intermediate peptidase. Some endopeptidases act only on substrates smaller than proteins, and these are termed oligopeptidases. An example of an oligopeptidase is thimet oligopeptidase. Endopeptidases initiate the digestion of food proteins, generating new N- and C-termini that are substrates for the exopeptidases that complete the process. Endopeptidases also process proteins by limited proteolysis. Examples are the removal of signal peptides from secreted proteins (e.g. signal peptidase I,) and the maturation of precursor proteins (e.g. enteropeptidase, furin,). In the nomenclature of the Nomenclature Committee of the International Union of Biochemistry and Molecular Biology (NC-IUBMB) endopeptidases are allocated to sub-subclasses EC 3.4.21, EC 3.4.22, EC 3.4.23, EC 3.4.24 and EC 3.4.25 for serine-, cysteine-, aspartic-, metallo- and threonine-type endopeptidases, respectively.

As used herein, a "cysteine peptidase" is a peptidase characterized by the presence of a cysteine at its active site, a serine peptidase is a peptidase characterized a serine at its active site; similarly derived terms are used for peptidases characterized by other amino acids at the active site.

As used herein a "metallopeptidase" refers to any protease enzyme whose catalytic mechanism involves a metal.

As used herein the term scissile bond refers to a peptide bond that is hydrolysed by a peptidase.

As used herein, the term "specificity subsite" refers to the specificity of a peptidase for cleavage of a peptide bond with particular amino acids in nearby positions and is described in terminology based on that originally created by Schechter & Berger to describe the specificity of papain. Schechter, I. & Berger, A. On the size of the active site in proteases. I. Papain. Biochem. Biophys. Res. Commun. 27, 157-162 (1967). Crystallographic structures of peptidases show that the active site is commonly located in a groove on the surface of the molecule between adjacent structural domains, and the substrate specificity is dictated by the properties of binding sites arranged along the groove on one or both sides of the catalytic site that is responsible for hydrolysis of the scissile bond. Accordingly, the specificity of a peptidase is described by use of a conceptual model in which each specificity subsite is able to accommodate the sidechain of a single amino acid residue. The sites are numbered from the catalytic site, S1, S2 ... Sn towards the N-terminus of the substrate, and S1', S2' ... Sn' towards the C-terminus. The residues they accommodate are numbered P1, P2 ... Pn, and P1', P2' ... Pn', respectively, as follows:
   Substrate: -P4 P3-P2-P1~P1'-P2'-P3'-P4'
   Enzyme: -S4 S3-S2-S1*S1'-S2'-S3'-S4'

In this representation the catalytic site of the enzyme is marked * and the peptide bond cleaved (the scissile bond) is indicated by the symbol ~.

As used herein short sequences of amino acids of specific length may be referred to as "dimers" comprising 2 amino acids, "trimers" comprising 3 amino acids, "tetramers" comprising 4 amino acids, and "octomers" comprising eight amino acids and so forth.

As used herein, the term "cleavage site octomer" refers to the 8 amino acids located four each side of the bond at which a peptidase cleaves an amino acid sequence. Cleavage site octomer is abbreviated as CSO.

As used herein "cleavage site dimer" refers to the amino acid pair between which cleavage may take place. Thus the cleavage site dimer refers to the P1~P1' amino acid pair, whether or not the bond between these two amino acids is actually cleaved or not. Cleavage site dimer defines a potential cleavage site. A cleavage site dimer occupies the central 2 amino acids of a cleavage site octomer.

As used herein, the term "cleavage site labeling" refers to experimental techniques in which the amino acid exposed by peptidase cleavage is labeled. Cleavage Site Labeling may be abbreviated herein as CSL. The principle is that each cleavage event by a peptidase produces a new N-terminal amino acid residue. Different chemistries can be used to label this new N-terminal residue and thus the following examples are not limiting. The process has been called "Terminal amine isotopic labeling of substrates" (TAILS). The specificity of the labeling and the addition of elements of precisely known mass enables the detection by mass spectrometry. One specific chemistry combines the use of $^{12}C$ and $^{13}C$ formaldehyde reactions. By labeling the control and the peptidase treated samples separately and then mixing them before analysis in the mass spectrometer the detection of the newly created N-terminal sites resulting from peptidase cleavage are detected by the addition of $^{13}C$ to the newly cleaved sites. A variation of the method is to metabolically label the substrate proteins to be tested in cell culture with stable isotopes of N, C or O. (called SILAC—"stable isotope labeling with amino acids in cell culture"). The difference between the labeled samples and the control can be subsequently detected with a mass spectrometer.

As used herein, the term "support vector machine" refers to a set of related supervised learning methods used for classification and regression. Given a set of training examples, each marked as belonging to one of two categories, an SVM training algorithm builds a model that predicts whether a new example falls into one category or the other.

As used herein, the term "classifier" when used in relation to statistical processes refers to processes such as neural nets and support vector machines.

As used herein "neural net", which is used interchangeably with "neural network" and sometimes abbreviated as NN, refers to various configurations of classifiers used in machine learning, including multilayered perceptrons with one or more hidden layer, support vector machines and dynamic Bayesian networks. These methods share in common the ability to be trained, the quality of their training evaluated and their ability to make either categorical classifications or of continuous numbers in a regression mode. Perceptron as used herein is a classifier which maps its input x to an output value which is a function of x, or a graphical representation thereof.

As used herein "recursive partitioning" or "recursive partitioning algorithm" refers to a statistical method for multivariable analysis. Recursive partitioning operates through a decision tree that strives to correctly classify members of the population based on several dichotomous dependent variables.

As used herein, the term "motif" refers to a characteristic sequence of amino acids forming a distinctive pattern.

As used herein, the term "genome" refers to the genetic material (e.g., chromosomes) of an organism or a host cell.

As used herein, the term "proteome" refers to the entire set of proteins expressed by a genome, cell, tissue or organism. A "partial proteome" refers to a subset the entire set of proteins expressed by a genome, cell, tissue or organism. Examples of "partial proteomes" include, but are not limited to, transmembrane proteins, secreted proteins, and proteins with a membrane motif.

As used herein, the terms "protein," "polypeptide," and "peptide" refer to a molecule comprising amino acids joined via peptide bonds. In general "peptide" is used to refer to a sequence of 20 or less amino acids and "polypeptide" is used to refer to a sequence of greater than 20 amino acids.

As used herein, the term, "synthetic polypeptide," "synthetic peptide" and "synthetic protein" refer to peptides, polypeptides, and proteins that are produced by a recombinant process (i.e., expression of exogenous nucleic acid encoding the peptide, polypeptide or protein in an organism, host cell, or cell-free system) or by chemical synthesis.

As used herein, the term "protein of interest" refers to a protein encoded by a nucleic acid of interest. It may be applied to any protein to which further analysis is applied or the properties of which are tested or examined.

As used herein, the term "native" (or wild type) when used in reference to a protein refers to proteins encoded by the genome of a cell, tissue, or organism, other than one manipulated to produce synthetic proteins.

As used herein, the term "B-cell epitope" refers to a polypeptide sequence that is recognized and bound by a B-cell receptor. A B-cell epitope may be a linear peptide or may comprise several discontinuous sequences which together are folded to form a structural epitope. Such component sequences which together make up a B-cell epitope are referred to herein as B-cell epitope sequences. Hence, a B cell epitope may comprise one or more B-cell epitope sequences. A linear B-cell epitope may comprise as few as 2-4 amino acids or more amino acids.

As used herein, the term "predicted B-cell epitope" refers to a polypeptide sequence that is predicted to bind to a B-cell receptor by a computer program, for example, in addition to methods described herein, Bepipred (Larsen, et al., Immunome Research 2:2, 2006.) and others as referenced by Larsen et al (ibid) (Hopp T et al PNAS 78:3824-3828, 1981; Parker J et al, Biochem. 25:5425-5432, 1986). A predicted B-cell epitope may refer to the identification of B-cell epitope sequences forming part of a structural B-cell epitope or to a complete B-cell epitope.

As used herein, the term "T-cell epitope" refers to a polypeptide sequence bound to a major histocompatibility protein molecule in a configuration recognized by a T-cell receptor. Typically, T-cell epitopes are presented on the surface of an antigen-presenting cell. A T-cell epitope comprises amino acids which are exposed outwardly towards the T-cell (T-cell exposed motifs or TCEMs) and amino acids which are directed inwardly towards the groove of the binding MHC molecule (Groove exposed motifs or GEMs).

As used herein, the term "predicted T-cell epitope" refers to a polypeptide sequence that is predicted to bind to a major histocompatibility protein molecule by the neural network algorithms described herein or as determined experimentally.

As used herein, the term "major histocompatibility complex (MHC)" refers to the MHC Class I and MHC Class II genes and the proteins encoded thereby. Molecules of the MHC bind small peptides and present them on the surface of cells for recognition by T-cell receptor-bearing T-cells. The MHC is both polygenic (there are several MHC class I and MHC class II genes) and polymorphic (there are multiple alleles of each gene). The terms MHC-I, MHC-II, MHC-1 and MHC-2 are variously used herein to indicate these classes of molecules. Included are both classical and non-classical MHC molecules. An MHC molecule is made up of multiple chains (alpha and beta chains) which associate to form a molecule. The MHC molecule contains a cleft which forms a binding site for peptides. Peptides bound in the cleft may then be presented to T-cell receptors. The term "MHC binding region" refers to the cleft region or groove of the MHC molecule where peptide binding occurs.

As used herein the terms "canonical" and "non-canonical" are used to refer to the orientation of an amino acid sequence. Canonical refers to an amino acid sequence presented or read in the N terminal to C terminal order; non-canonical is used to describe an amino acid sequence presented in the inverted or C terminal to N terminal order.

As used herein, the term "haplotype" refers to the HLA alleles found on one chromosome and the proteins encoded thereby. Haplotype may also refer to the allele present at any one locus within the MHC.

As used herein, the term "polypeptide sequence that binds to at least one major histocompatibility complex (MHC) binding region" refers to a polypeptide sequence that is recognized and bound by one more particular MHC binding regions as predicted by the neural network algorithms described herein or as determined experimentally.

As used herein, the term "allergen" refers to an antigenic substance capable of producing immediate hypersensitivity and includes both synthetic as well as natural immunostimulant peptides and proteins.

As used herein, the term "transmembrane protein" refers to proteins that span a biological membrane. There are two basic types of transmembrane proteins. Alpha-helical proteins are present in the inner membranes of bacterial cells or the plasma membrane of eukaryotes, and sometimes in the outer membranes. Beta-barrel proteins are found only in outer membranes of Gram-negative bacteria, cell wall of Gram-positive bacteria, and outer membranes of mitochondria and chloroplasts.

As used herein, the term "external loop portion" refers to the portion of transmembrane protein that is positioned between two membrane-spanning portions of the transmembrane protein and projects outside of the membrane of a cell.

As used herein, the term "tail portion" refers to refers to an n-terminal or c-terminal portion of a transmembrane protein that terminates in the inside ("internal tail portion") or outside ("external tail portion") of the cell membrane.

As used herein, the term "secreted protein" refers to a protein that is secreted from a cell.

As used herein, the term "membrane motif" refers to an amino acid sequence that encodes a motif not in a canonical transmembrane domain but which would be expected by its function deduced in relation to other similar proteins to be located in a cell membrane, such as those listed in the publically available psortb database.

As used herein, the term "consensus peptidase cleavage site" refers to an amino acid sequence that is recognized by a peptidase such as trypsin or pepsin.

As used herein, the term "affinity" refers to a measure of the strength of binding between two members of a binding pair, for example, an antibody and an epitope and an epitope and a MHC-I or II haplotype. $K_d$ is the dissociation constant and has units of molarity. The affinity constant is the inverse of the dissociation constant. An affinity constant is sometimes used as a generic term to describe this chemical entity. It is a direct measure of the energy of binding. The natural logarithm of K is linearly related to the Gibbs free energy of binding through the equation $\Delta G_0 = -RT\,LN(K)$ where R=gas constant and temperature is in degrees Kelvin. Affinity may be determined experimentally, for example by surface plasmon resonance (SPR) using commercially available Biacore SPR units (GE Healthcare) or in silico by methods such as those described herein in detail. Affinity may also be expressed as the ic50 or inhibitory concentration 50, that concentration at which 50% of the peptide is displaced. Likewise ln(ic50) refers to the natural log of the ic50.

As used herein, the term "immunogen" refers to a molecule which stimulates a response from the adaptive immune system, which may include responses drawn from the group comprising an antibody response, a cytotoxic T cell response, a T helper response, and a T cell memory. An immunogen may stimulate an upregulation of the immune response with a resultant inflammatory response, or may result in down regulation or immunosuppression. Thus the T-cell response may be a T regulatory response.

As used herein, the term "flanking" refers to those amino acid positions lying outside, but immediately adjacent to a peptide sequence of interest. For example amino acids flanking the MHC binding region lie within 1-4 amino acids of either terminal amino acid of the MHC binding peptide.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "principal component analysis" refers to a mathematical process which reduces the dimensionality of a set of data (Wold, S., Sjorstrom, M., and Eriksson, L., Chemometrics and Intelligent Laboratory Systems 2001. 58: 109-130; Multivariate and Megavariate Data Analysis Basic Principles and Applications (Parts I&II) by L. Eriksson, E. Johansson, N. Kettaneh-Wold, and J., 2006 $2^{nd}$ Edit. Umetrics Academy). Derivation of principal components is a linear transformation that locates directions of maximum variance in the original input data, and rotates the data along these axes. For n original variables, n principal components are formed as follows: The first principal component is the linear combination of the standardized original variables that has the greatest possible variance. Each subsequent principal component is the linear combination of the standardized original variables that has the greatest possible variance and is uncorrelated with all previously defined components. Thus a feature of principal component analysis is that it determines the weighting and ranking of each principal component and thus the relative contribution each makes to the underlying variance. Further, the principal components are scale-independent in that they can be developed from different types of measurements.

As used herein, the term "vector" when used in relation to a computer algorithm or the present invention, refers to the mathematical properties of the amino acid sequence.

As used herein, the term "vector," when used in relation to recombinant DNA technology, refers to any genetic element, such as a plasmid, phage, transposon, cosmid, chromosome, retrovirus, virion, etc., which is capable of replication when associated with the proper control elements and which can transfer gene sequences between cells. Thus, the term includes cloning and expression vehicles, as well as viral vectors.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acids are nucleic acids present in a form or setting that is different from that in which they are found in nature. In contrast, non-isolated nucleic acids are nucleic acids such as DNA and RNA that are found in the state in which they exist in nature.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

A "subject" is an animal such as vertebrate, preferably a mammal such as a human, a bird, or a fish. Mammals are understood to include, but are not limited to, murines, simians, humans, bovines, cervids, equines, porcines, canines, felines etc.).

An "effective amount" is an amount sufficient to effect beneficial or desired results. An effective amount can be administered in one or more administrations, As used herein, the term "purified" or "to purify" refers to the removal of undesired components from a sample. As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated. An "isolated polynucleotide" is therefore a substantially purified polynucleotide.

As used herein "regulatory T cells" refers to a subpopulation of T cells which are immunosuppressive and downregulate the immune system. T regulatory cells may function to maintain tolerance to self-antigens, and downregulate autoimmune disease. Regulatory T cells may be abbreviated herein as $T_{reg}$, or Treg.

As used herein "orthogonal" refers to a parameter or a mathematical expression which is statistically independent from another such parameter or mathematical expression. Hence orthogonal and uncorrelated are used interchangeably herein.

As used herein "bagging" which is an abbreviated term for "bootstrap aggregation" is used to describe a process whereby small, balanced subsets of data are selected randomly from a larger training dataset and processed, followed by processing of a further randomly selected subset of data from the same dataset. This cycle is repeated multiple times with different random subsets from the same dataset. This process is used for training and validation of the classifiers, then allowing the resulting predictors to be applied to larger datasets. For instance 5 k-fold cross validation may be performed 5 times, each time starting with a different seed for the random number generator.

As used herein "ensemble" is used to describe a collection of similar equations or computer processes each contributing to an overall analysis. In some instances an ensemble may be a series of predictive equations each focused on a prediction specific to a particular circumstance. Ensembles may be used as a form of analysis as a "committee" where a determination is based on the "vote" of each member of the ensemble. Thus if 8 of 10 equations predict outcome "A" and 2 of 10 predict outcome "not A" then a prediction of 0.8 probability of A is made As used herein "enzyme class" and the associated numbering of enzyme classes refers to the classification system developed by the Nomenclature Committee of the International Union of Biochemistry and Molecular Biology on the Nomenclature and Classification of Enzymes by the Reactions they Catalyse. This standardized nomenclature may be accessed at the website www.chem.qmul.ac.uk/iubmb/enzyme/

DETAILED DESCRIPTION OF THE INVENTION

This invention relates to the identification of predicted peptidase cleavage sites in proteins or peptides. Predictions of some peptidase cleavage sites like trypsin are quite simple. For example, trypsin cleaves the bond located on the C terminus side of a lysine or arginine. Other peptidases are much more discriminating and the context of their cleavage sites is much more complex. Hence definition of their cleavage site has been challenging, as simple observation of amino acid sequences does not provide indications of characteristic sequence motifs.

The accurate prediction of peptidase cleavage sites is of great utility as it can allow application of the output of experimental data from experiments on one or a few proteins, often the result of expensive and cumbersome procedures, to be applied to many other proteins of interest. Hence the prediction of peptidase cleavage positions within proteins and peptides is an important objective. In silico prediction schemes have been developed using several types of algorithms, and the topic has been reviewed recently. See, e.g., Shen H B, Chou K C (2009) Identification of proteases and their types. Anal Biochem 385: 153-160; Chou K C, Shen H B (2008) ProtIdent: a web server for identifying proteases and their types by fusing functional domain and sequential evolution information. Biochem Biophys Res Commun 376: 321-325; Lohmuller T, Wenzler D, Hagemann S, Kiess W, Peters C, et al. (2003) Toward computer-based cleavage site prediction of cysteine endopeptidases. Biol Chem 384: 899-909; Song J, Tan H, Boyd S E, Shen H, Mahmood K, et al. (2011) Bioinformatic approaches for predicting substrates of proteases. J Bioinform Comput Biol 9: 149-178. All of these predictors are "binary classifiers", which rely on standard alphabetic representation of amino acids, and assign a probability to whether the scissile bond between a particular amino acid pair will be cleaved or not. In use, they are "trained" with a set of known sequences and then those results are extrapolated to other situations with various scoring metrics used to assess how well the classifiers perform outside of their "training" environment. A number of classifiers have been shown to perform reasonably well for a small number of enzymes, typically those with high levels of sequence specificity within the CSO, and trained with a very limited number of cleavage targets. See, e.g., Song et al.; Yang Z R (2005) Prediction of caspase cleavage sites using Bayesian bio-basis function neural networks. Bioinformatics 21: 1831-1837. Development of rule-based predictors can be a complex task and often the rules derived are difficult to understand. See, e.g., Rognvaldsson T, Etchells T A, You L, Garwicz D, Jarman I, et al. (2009) How to find simple and accurate rules for viral protease cleavage specificities. BMC Bioinformatics 10: 149.

Several additional factors have hampered the peptidase prediction field. For any particular peptidase only relatively small data sets are available, given the laborious experimental approaches needed to define the cleavage characteristics. Hence, classifiers have used training sets only up to several hundred cleavages for any particular peptidase. See, e.g., Song et al vide supra. The ability to generalize beyond a small training set is questionable and often difficult to evaluate. There is also likely a high degree of bias in the existing datasets because the experimental approaches used to generate the data are purposefully executed with highly non-random peptide selections. Therefore the experimental techniques have the potential to bias the predictions based on them.

An additional complicating factor is the need for "true negatives" in order to develop any binary classifier. Experimentalists' understandable focus on positive experimental results exacerbates this issue whenever experimental data is used in classifier development. The mass of data produced by CSL techniques, and the randomness of the peptide sequences, should provide the basis for more reliable predictions of proteolytic cleavage than have heretofore been possible. In addition, this experimental approach provides the opportunity for the peptidases to bind to a very large number of CSOs in protein mixtures and therefore also provides a large set of true negative CSO peptides that have been exposed to the enzyme for extended periods of time without resulting in cleavage.

In some embodiments, the ability to predict peptidases also facilitates the development of drugs which are peptidase inhibitors.

Proteome information is now available for many organisms and the list of available proteomes is increasing daily. Mapping locations within proteins at which peptidases cleave has been a laborious process involving either chemical synthesis of many substrates or isolation of peptides from post-cleavage mixtures, determination of their sequences and deduction of their location within the parent protein molecule. Several new proteomic techniques have recently been developed that enable identification of newly created cleavage sites through a combination of isotopic or other labeling of the residues flanking the cleavage site and mass spectrometry. See, e.g., Kleifeld O, Doucet A, auf dem KU, Prudova A, Schilling O, et al. (2010) Isotopic labeling of terminal amines in complex samples identifies protein N-termini and protease cleavage products. Nat Biotechnol 28: 281-288; Doucet A, Butler G S, Rodriguez D, Prudova A, Overall C M (2008) Metadegradomics: toward in vivo quantitative degradomics of proteolytic post-translational modifications of the cancer proteome. Mol Cell Proteomics 7: 1925-1951; auf dem K U, Schilling O (2010) Proteomic techniques and activity-based probes for the system-wide study of proteolysis. Biochimie 92: 1705-1714; Impens F, Colaert N, Helsens K, Plasman K, Van D P, et al. (2010) MS-driven protease substrate degradomics. Proteomics 10: 1284-1296; Agard N J, Wells J A (2009) Methods for the proteomic identification of protease substrates. Curr Opin Chem Biol 13: 503-509. These techniques are capable of deducing thousands of new cleavage locations in mixtures containing hundreds of proteins in a single experiment. Thus, one experiment can characterize hundreds of times as many cleavage events as had been previously catalogued for a particular peptidase. These approaches fall into two broad categories: a peptide-centric two stage processes where a protein mixture is first fragmented with a first protease before the protease under study is deployed, and a second, more biological process where the protease under study is given access to a mixture of intact protein molecules. See, e.g., Kleifeld et al., Doucet et al., Schilling et al., and Impens et al., supra.

The cleavage site repertoire of a specific peptidase in a particular set of experimental conditions is itself useful, but given the combinatorial diversity of proteins, there is a need to be able to extrapolate beyond the experimental results obtained and to use these techniques as the basis to build a system to reliably predict cleavage in any protein.

The region around the active site of peptidases has been conceptualized as an enzyme binding pocket comprising a series of contiguous topographic subsites following on the work of Schechter and Berger with papain. On the cleaved protein the subsites are consecutively numbered outward from the cleavage site between P1 and P1' as P4-P3-P2-P1|P1'-P2'-P3'-P4' and the corresponding binding sites on the enzyme numbered S4 . . . S4'. Although recent work has indicated the importance of amino acid residues outside this region, the cleavage site octomer (CSO) is conventionally the focus of research efforts on the cleavage event. See, e.g., Ng N M, Quinsey N S, Matthews A Y, Kaiserman D, Wijeyewickrema L C, et al. (2009) The effects of exosite occupancy on the substrate specificity of thrombin. Arch Biochem Biophys 489: 48-54. Several online databases (cutdb.burnham.org/; merops.sanger.ac.uk/; clipserve.clip.ubc.ca/pics/) contain extensive catalogs of cleavage events and online prediction tools are also available. Perhaps the most comprehensive is the POPS web-based prediction system (pops.csse.monash.edu.au/pops-cgi/). Boyd S E, Pike R N, Rudy G B, Whisstock J C, Garcia dlB (2005) PoPS: a computational tool for modeling and predicting protease specificity. J Bioinform Comput Biol 3: 551-585.

The field of bioinformatics has provided powerful tools to analyze large datasets arising from sequenced genomes, proteomes and transcriptomes. But often analysis of the proteomic information has been based on individual amino acids, using sequences, not segments, and without translation to structure, biological function and location of the proteins in the whole organism.

For the reasons stated above there is a need for a method to identify peptidase cleavage sites. Accordingly, in some embodiments, the present invention provides computer implemented processes of identifying peptidase cleavage sites within polypeptides and proteins and the predicted peptide and polypeptide fragments that are generated by peptidase activity.

Principal component analysis is a very powerful statistical tool that is being used increasingly to reduce the dimensionality of large data sets in data mining applications and in systems biology analytics. The inventors recently showed that the principal components of amino acid (PCAA) physical properties could be used in combination with large training sets in public databases to predict the binding affinity of peptides to major histocompatability complex I (MHC I) and MHC II molecules. Bremel R D, Homan E J (2010) An integrated approach to epitope analysis I: Dimensional reduction, visualization and prediction of MHC binding using amino acid principal components and regression approaches. Immunome Res 6: 7. 1745-7580-6-7; Bremel R D, Homan E J (2010) An integrated approach to epitope analysis II: A system for proteomic-scale prediction of immunological characteristics. Immunome Res 6: 8. 1745-7580-6-8).

The current invention provides inventive applications of statistical work of Wold and his colleagues who introduced the concept of amino acid principal components of small peptides in a predictive way with a partial least squares (PLS) regression process. See, e.g., Sjostrom M, Eriksson L, Hellberg S, Jonsson J, Skagerberg B, et al. (1989) Peptide QSARS: PLS modelling and design in principal properties, Prog Clin Biol Res 291: 313-317; Hellberg S, Sjostrom M, Skagerberg B, Wold S (1987) Peptide quantitative structure-activity relationships, a multivariate approach. J Med Chem 30: 1126-1135; Linusson A, Elofsson M, Andersson I E, Dahlgren M K (2010) Statistical molecular design of balanced compound libraries for QSAR modeling. Curr Med Chem 17: 2001-2016; Linusson A, Gottfries J, Lindgren F, Wold S (2000) Statistical molecular design of building blocks for combinatorial chemistry. J Med Chem 43: 1320-1328.

PLS concepts have played a major role in the growth of the field of medicinal chemistry chemometrics but have not been exploited in the field of bioinformatics. The similarity between the octomer binding pocket of a peptidase and the binding pocket of an MHC molecule is obvious and suggested that perhaps a similar process might be developed for predicting peptidase cleavage probabilities instead of binding affinities. Our preliminary work in this area prior to the availability of the CSL experimental results identified the generally small datasets for training the classifiers as being a fundamental limitation. The CSL datasets now becoming available provide training sets of adequate sizes to produce reliable prediction tools.

In some embodiments, the present invention provides processes, preferably computer implemented, for the derivation of ensembles of equations for the prediction of peptidase cleavage. In some embodiments the process comprises generating mathematical expressions based on multiple uncorrelated physical parameters of amino acids, wherein said mathematical expressions serve as descriptors of a peptide. The peptide descriptor is then applied to a training set of peptides for which the cleavage site and probability has been experimentally determined. The mathematical descriptors and the experimental data are then compared and a prediction equation derived for cleavage of the scissile bond between each possible pair of amino acids located in the cleavage site dimer positions. In some embodiments the process is then repeated to derive an equation for each possible pair of amino acids in a cleavage site dimer. The assemblage of equations for every possible cleavage site dimer then constitutes an ensemble of predictive equations which can be used together to determine a probability of cleavage.

In some embodiments, the mathematical expression which is a peptide descriptor is derived by analyzing more than one uncorrelated physical parameters of an amino acid via a computer processor, and constructing a correlation matrix of said physical parameters. In some embodiments this permits the derivation of multiple mutually orthogonal or uncorrelated proxies, wherein said proxies are weighted and ranked to provide descriptors of the amino acids. In further embodiments a number of the proxies which contribute most to the description of the amino acid variability are then selected to serve as descriptors. In some embodiments this number of proxies may be three or more. In some embodiments the proxies are principal components. In further embodiments, by combining the mathematical expression comprising several proxies describing each amino acid in a peptide, a mathematical descriptor for the peptide is derived.

In some embodiments, the computer assisted process of assembling an ensemble of equations to predict peptide cleavage requires first deriving a predictive equation for each cleavage site dimer pair of amino acids. By examining a set of peptides for which the cleavage is known, cleavage site dimers are identified which are comprised of identical amino acids but which are located in peptides that are either cleaved or uncleaved. A sub set of peptides with these properties is randomly selected. By comparison of the cleaved and uncleaved peptides with the aforesaid peptide descriptors, a first equation is derived to predict cleavage for that cleavage site dimer. This process is repeated on a second random sub set of the peptides and then repeated multiple times, each time enhancing the precision of the predictive equation for the particular cleavage site dimer. In some embodiments, the derivation of a predictive equation is then conducted for other cleavage site dimer amino acid pairs until the maximum of 400 possible pairs has been examined and the corresponding predictive equations derived form an ensemble of predictive equations.

In some embodiments, the predictive equations are then applied to a protein of interest, wherein the invention provides for inputting the protein of interest into a computer and applying amino acid descriptors based on multiple uncorrelated physical parameters to provide a peptide descriptor for each peptide comprised of a subset of amino acids from within the protein of interest. In some embodiments the process then further comprises applying the peptidase prediction equation ensemble to predict the cleavage site dimers in the peptides from the protein of interest and the probability of cleavage of each cleavage site dimer. In some particular embodiments the probability of cleavage may be 60% or 70% or 80% or 90% or higher.

In some embodiments, the present invention provides computer implemented processes of identifying peptides that interact with a peptidase and applying a mathematical expression to predict the interaction (e.g., cleavage) of the amino acids subset with the partner using a classifier.

In some embodiments, the classifier is a probabilistic classifier. In some embodiments, the probabilistic classifier is a probabilistic trained neural network. In yet other embodiments, the probabilistic classifier is a support vector machine. In yet further embodiments, the probabilistic classifier is a recursive partitioning algorithm. Other classifiers may be applied, thus these examples are not limiting.

In some preferred embodiments, the methods are used to predict peptidase cleavage using a neural network prediction scheme based on amino acid physical property principal components. Briefly, a protein is broken down into 8-mer peptides each offset by 1 amino acid. The peptide 8-mers are converted into vectors of principal components wherein each amino acid in a 8-mer is replaced by three z-scale descriptors. $\{z1(aa1),z2(aa1),z3(aa1)\}$, $\{z1(aa2),z2(aa2),z3(aa2)\}$, $\{z1(aa8),z2(aa8),z3(aa8)\}$ that are effectively physical property proxy variables. With these descriptors ensembles of neural network prediction equation sets are developed, using publicly available datasets of peptidase cleavage sites derived from experimentation. See, e.g., Impens et al., Bianossek et al., and Tholen et al., referenced above. In preferred embodiments, the peptide data is indexed to the N-terminal amino acid and thus each prediction corresponds to the 8-amino acid peptide downstream from the index position.

The methodology described herein enables the description of predicted peptidase cleavage of a protein, based on the use of principal components as proxies for the salient physical parameters of the peptide. Having used the principal components to reduce the dimensionality of the descriptors to a mathematical expression which is a descriptor of the peptide and its component amino acids, it is then possible to analyze statistically the peptide within which cleavage occurs.

In some preferred embodiments, the processes described above are applied to understanding the context of cleavage of endopeptidases. In some embodiments the endopeptidases are in enzyme class 3.4.21, 3.4.22, 3.4.23, or 3.4.21 and include serine proteases, cysteine proteases, aspartic acid proteases, and metalloendopeptidases. In other preferred embodiments, the peptidase is a cathepsin. Representative cathepsins include, but are not limited to, Cathepsin A (serine protease), Cathepsin B (cysteine protease), Cathepsin C (cysteine protease), Cathepsin D (aspartyl protease), Cathepsin E (aspartyl protease), Cathepsin F (cysteine proteinase), Cathepsin G (serine protease), Cathepsin H (cysteine protease), Cathepsin K (cysteine protease), Cathepsin L1 (cysteine protease), Cathepsin L2 (or V) (cysteine protease), Cathepsin O (cysteine protease), Cathepsin S (cysteine protease), Cathepsin W (cysteine proteinase), and Cathepsin Z (or X) (cysteine protease).

In one particular embodiment, principal component analysis is applied to identify peptidase cleavage sites in target proteins. These and other embodiments are described in more detail below.

A. Limitations of Position Scoring Matrices

Position specific scoring matrices (PSSM) are widely used in bioinformatics analysis and have been used to characterize patterns of amino acids around the cleavage site within the CSO on the N-terminal and C-terminal side of the scissile bond. The MEROPS database provides both a tabular and a graphic description of the CSO, depicting the frequency of occurrence of amino acids at each position. However a fundamental weakness of PSSM is that it assumes position independence and cannot be used to assess combinatorial relationships and interactions among the different positions within the CSO. While providing a basis for graphically depicting the amino acids at different locations, the matrices are not in themselves useful in predictive processes. Predictive systems such as POPS use other additional biophysical data and predictions in conjunction with the PSSM in a rule-based system to derive cleavage probability predictions.

B. Application of Proteome Information

In some embodiments, the present invention provides processes that make it possible to analyze proteomic-scale information on a personal computer, using commercially available statistical software and database tools in combination with several unique computational procedures. The present invention improves computational efficiency by utilizing amino acid principal components as proxies for physical properties of the amino acids, rather than a traditional alphabetic substitution matrix bioinformatics approach. A particular advantage of principal component analysis is that the weighting and ranking of the principal components reflect the contribution of each to the underlying variance. Principal components thus provide uncorrelated proxies which are weighted and ranked. This has allowed new, more accurate and more efficient procedures for peptidase cleavage site definition to be realized.

A proteome (1) is a database table consisting of all of the proteins that are predicted to be coded for in an organism's genome. A large number of proteomes are publicly available from Genbank in an electronic form that have been curated to describe the known or putative physiological function of the particular protein molecule in the organism. Advances in DNA sequencing technology now makes it possible to sequence an entire organism's genome in a day and will greatly expand the availability of proteomic information. Having many strains of the same organism available for analysis will improve the potential for defining protease motifs universally. However, the masses of data available will also require that tools such as those described in this specification be made available to a scientist without the limitations of those resources currently available over the internet.

Proteins are uniquely identified in genetic databases. The Genbank administrators assign a unique identifier to the genome (GENOME) of each organism strain. Likewise a unique identifier called the Gene Index (GI) is assigned to each gene and cognate protein in the genome. As the GENOME and GI are designed to be unique identifiers they are used in this specification in all database tables and to track the proteins as the various operations are carried out. By convention the amino acid sequences of proteins are written from N-terminus (left) to C-terminus (right) corresponding to the translation of the genetic code. A 1-based numbering system is used where the amino acid at the N-terminus is designated number 1, counting from the signal peptide methionine. At various points in the process it is necessary to unambiguously identify the location of a certain amino acid or groups of amino acids. For this purpose, a four component addressing system has been adopted that has the four elements separated by dots (Genome.GI.N.C).

Figure 8:
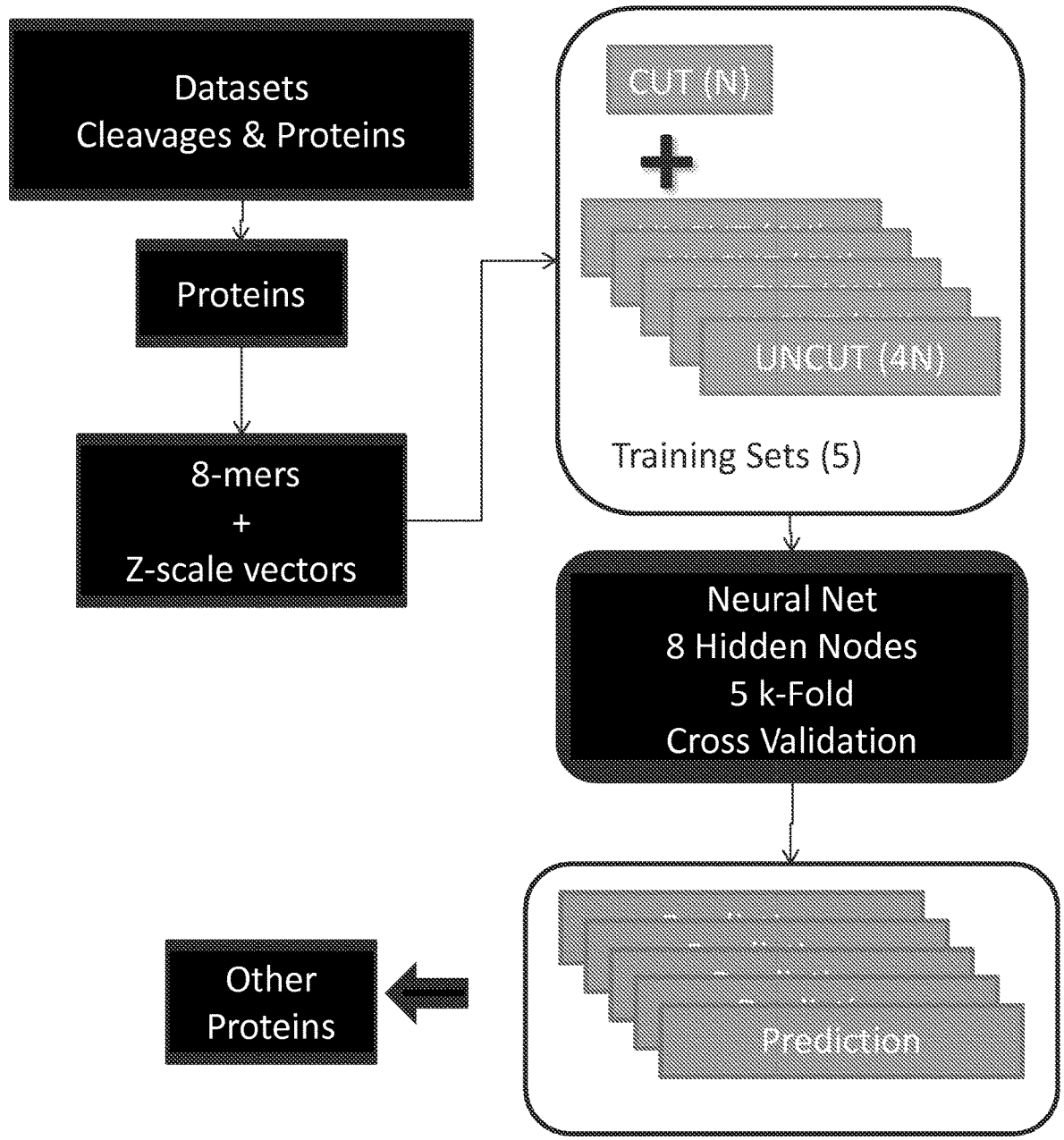

Referring to FIG. 8, in some embodiments, a Proteome of interest is obtained in "FASTA" format via FTP transfer from the Genbank website. This format is widely used and consists of a single line identifier beginning with a single ">" and contains the GENOME and GI plus the protein's curation and other relevant organismal information followed by the protein sequence itself. In addition to the FASTA formatted file a database table is created that contains all of the information.

In some embodiments, principal components of amino acids are utilized to generate a mathematical algorithm which provides a peptide descriptor that encompasses the variability derived from the physical properties of a a peptide, based on the amino acids therein. By analyzing such mathematical descriptors in relation to observed experimental data ensembles of predictive equations can be developed which in aggregate can peptidase accurately predict a cleavage site.

C. Application of Principal Component Analysis Principal Components

Analysis is a mathematical process that is used in many different scientific fields and which reduces the dimensionality of a set of data. (Bishop, C. M., Neural Networks for Pattern Recognition. Oxford University Press, Oxford 1995. Bouland, H. and Kamp, Y., Biological Cybernetics 1988. 59: 291-294.).

In the present invention, Principal Component Analysis is used to derive a mathematical algorithm which serves as a descriptor of an amino acids, representing the variance in physical properties. By combination of algorithms derived to describe single amino acids, descriptors for peptides can be assembled and used as descriptors for peptides in which the interdependency of the amino acids therein is accounted for. The several principal components are used to describe each amino acid function as uncorrelated or orthogonal proxies.

Derivation of principal components is a linear transformation that locates directions of maximum variance in the original input data, and rotates the data along these axes. Typically, the first several principal components contain the most information. Principal component analysis is particularly useful for large datasets with many different variables. Using principal components provides a way to picture the structure of the data as completely as possible by using as few variables as possible. For n original variables, n principal components are formed as follows: The first principal component is the linear combination of the standardized original variables that has the greatest possible variance. Each subsequent principal component is the linear combination of the standardized original variables that has the greatest possible variance and is uncorrelated with all previously defined components. Further, the principal components are scale-independent in that they can be developed from different types of measurements. For example, datasets from HPLC retention times (time units) or atomic radii (cubic angstroms) can be consolidated to produce principal components. Another characteristic is that principal components are weighted appropriately for their respective contributions to the response and one common use of principal components is to develop appropriate weightings for regression parameters in multivariate regression analysis. Outside the field of immunology, principal components analysis (PCA) is most widely used in regression analysis. Initial tests were conducted using the principal components in a multiple regression partial least squares (PLS) approach. See, e.g., Bouland H, Kamp Y (1988) Auto association by multilayer perceptrons and singular value deomposition. Biological Cybernetics 59: 291-294). Principal component analysis can be represented in a linear network. PCA can often extract a very small number of components from quite high-dimensional original data and still retain the important structure.

Over the past half century a wide array studies of physicochemical properties of amino acids have been made. Others have made tabulations of principal components, for example in the paper Wold et al. that describes the mathematical theory underlying the use of principal components in partial least squares regression analysis. Wold S, Sjorstrom M, Eriksson L (2001) PLS-regression: a basic tool of chemometrics. Chemometrics and Intelligent Laboratory Systems 58: 109-130. The work of Wold et al uses eight physical properties.

Accordingly, in some embodiments, physical properties of amino acids are used for subsequent analysis. In some embodiments, the compiled physical properties are available at a proteomics resource website (expasy.org/tools/protscale.html). In some embodiments, the physical properties comprise one or more physical properties derived from the 31 different studies as shown in Table 1. In some embodiments, the data for each of the 20 different amino acids from these studies are tabulated, resulting in 20×31 different datapoints, each providing a unique estimate of a physical characteristic of that amino acid. The power of principal component analysis lies in the fact that the results of all of these studies can be combined to produce a set of mathematical properties of the amino acids which have been derived by a wide array of independent methodologies. The patterns derived in this way are similar to those of Wold et.

al. but the absolute numbers are different. The physicochemical properties derived in the studies used for this calculation are shown in (Table 1). FIG. 2 shows Eigen values for the 19-dimensional space describing the principal components, and further shows that the first three principal component vectors account for approximately 89.2% of the total variation of all physicochemical measurements in all of the studies in the dataset. All subsequent work described herein is based on use of the first three principal components.

TABLE 1

| | | |
|---|---|---|
| 1 | Polarity. | Zimmerman, J. M., Eliezer, N., and Simha, R., J. Theor. Biol. 1968. 21: 170-201. |
| 2 | Polarity (p). | Grantham, R., Science 1974. 185: 862-864. |
| 3 | Optimized matching hydrophobicity (OMH). | Sweet, R. M. and Eisenberg, D., J. Mol. Biol. 1983. 171: 479-488. |
| 4 | Hydropathicity. | Kyte, J. and Doolittle, R. F.,. J. Mol. Biol. 1982. 157: 105-132. |
| 5 | Hydrophobicity (free energy of transfer to surface in kcal/mole). | Bull, H. B. and Breese, K., Arch. Biochem. Biophys. 1974. 161: 665-670. |
| 6 | Hydrophobicity scale based on free energy of transfer (kcal/mole). | Guy, H. R., Biophys. J. 1985. 47: 61-70. |
| 7 | Hydrophobicity (delta G1/2 cal) | Abraham, D. J. and Leo, A. J., Proteins 1987. 2: 130-152. |
| 8 | Hydrophobicity scale (contact energy derived from 3D data). | Miyazawa, S. and Jernigan, R. L., Macromolecules 1985. 18: 534-552. |
| 9 | Hydrophobicity scale (pi-r). | Roseman, M. A., J. Mol. Biol. 1988. 200: 513-522. |
| 10 | Molar fraction (%) of 2001 buried residues. | Janin, J., Nature 1979. 277: 491-492. |
| 11 | Proportion of residues 95% buried (in 12 proteins). | Chothia, C., J. Mol. Biol. 1976. 105: 1-12. |
| 12 | Free energy of transfer from inside to outside of a globular protein. | Janin, J., Nature 1979. 277: 491-492. |
| 13 | Hydration potential (kcal/mole) at 25° C. | Wolfenden, R., Andersson, L., Cullis, P. M., and Southgate, C. C., Biochemistry 1981. 20: 849-855. |
| 14 | Membrane buried helix parameter. | Rao, M. J. K. and Argos, P., Biochim. Biophys. Acta 1986. 869: 197-214. |
| 15 | Mean fractional area loss (f) [average area buried/standard state area]. | Rose, G. D., Geselowitz, A. R., Lesser, G. J., Lee, R. H., and Zehfus, M. H., Science 1985. 229: 834-838. |
| 16 | Average area buried on transfer from standard state to folded protein. | Rose, G. D., Geselowitz, A. R., Lesser, G. J., Lee, R. H., and Zehfus, M. H., Science 1985. 229: 834-838. |
| 17 | Molar fraction (%) of 3220 accessible residues. | Janin, J., Nature 1979. 277: 491-492. |
| 18 | Hydrophilicity. | Hopp, T. P., Methods Enzymol. 1989. 178: 571-585. |
| 19 | Normalized consensus hydrophobicity scale. | Eisenberg, D., Schwarz, E., Komaromy, M., and Wall, R., J. Mol. Biol. 1984. 179: 125-142. |
| 20 | Average surrounding hydrophobicity. | Manavalan, P. and Ponnuswamy, P. K., Nature 1978. 275: 673-674. |
| 21 | Hydrophobicity of physiological L-alpha amino acids | Black, S. D. and Mould, D. R., Anal. Biochem. 1991. 193: 72-82 |
| 22 | Hydrophobicity scale (pi-r)2. | Fauchere, J. L., Charton, M., Kier, L. B., Verloop, A., and Pliska, V., Int. J. Pept. Protein Res. 1988. 32: 269-278. |
| 23 | Retention coefficient in HFBA. | Browne, C. A., Bennett, H. P., and Solomon, S., Anal. Biochem. 1982. 124: 201-208. |
| 24 | Retention coefficient in HPLC, pH 2.1. | Meek, J. L., Proc. Natl. Acad. Sci. U.S.A 1980. 77: 1632-1636. |
| 25 | Hydrophilicity scale derived from HPLC peptide retention times. | Parker, J. M., Guo, D., and Hodges, R. S., Biochemistry 1986. 25: 5425-5432. |
| 26 | Hydrophobicity indices at ph 7.5 determined by HPLC. | Cowan, R. and Whittaker, R. G., Pept. Res. 1990. 3: 75-80. |
| 27 | Retention coefficient in TFA | Browne, C. A., Bennett, H. P., and Solomon, S., Anal. Biochem. 1982. 124: 201-208. |
| 28 | Retention coefficient in HPLC, pH 7.4 | Meek, J. L., Proc. Natl. Acad. Sci. U.S.A 1980. 77: 1632-1636. |
| 29 | Hydrophobicity indices at pH 3.4 determined by HPLC | Cowan, R. and Whittaker, R. G., Pept. Res. 1990. 3: 75-80. |
| 30 | Mobilities of amino acids on chromatography paper (RF) | Akintola, A. and Aboderin, A. A., Int. J. Biochem. 1971. 2: 537-544. |
| 31 | Hydrophobic constants derived from HPLC peptide retention times | Wilson, K. J., Honegger, A., Stotzel, R. P., and Hughes, G. J., Biochem. J. 1981. 199: 31-41. |

In some embodiments, principal component vectors derived are shown in Table 2. Each of the first three principal components is sorted to demonstrate the underlying physicochemical properties most closely associated with it. From this it can be seen that the first principal component (Prin1) is an index of amino acid polarity or hydrophobicity; the most hydrophobic amino acids have the highest numerical value. The second principal component (Prin2) is related to the size or volume of the amino acid, with the smallest having the highest score. The physicochemical properties embodied in the third component (Prin3) are not immediately obvious, except for the fact that the two amino acids containing sulfur rank among the three smallest magnitude values.

TABLE 2

| Amino acid | Prin1 | Amino Acid | Prin2 | Amino Acid | Prin3 |
| --- | --- | --- | --- | --- | --- |
| K | −6.68 | W | −3.50 | C | −3.84 |
| R | −6.30 | R | −2.93 | H | −1.94 |
| D | −6.04 | Y | −2.06 | M | −1.46 |
| E | −5.70 | F | −1.53 | E | −1.46 |
| N | −4.35 | K | −1.32 | R | −0.91 |
| Q | −3.97 | H | −1.00 | V | −0.35 |
| S | −2.65 | Q | −0.47 | D | −0.18 |
| H | −2.55 | M | −0.43 | I | 0.04 |
| T | −1.42 | P | −0.36 | F | 0.05 |
| G | −0.76 | L | −0.20 | Q | 0.15 |
| P | −0.03 | D | 0.03 | W | 0.16 |
| A | 0.72 | N | 0.21 | N | 0.30 |
| C | 2.11 | I | 0.29 | Y | 0.37 |
| Y | 2.58 | E | 0.34 | T | 0.94 |
| M | 4.14 | T | 0.80 | K | 1.16 |
| V | 4.79 | S | 1.84 | L | 1.17 |
| W | 5.68 | V | 1.98 | G | 1.21 |
| L | 6.59 | A | 2.48 | S | 1.30 |
| I | 6.65 | C | 2.74 | A | 1.42 |
| F | 7.18 | G | 3.08 | P | 1.87 |

In some embodiments, the systems and processes of the present invention use from about one to about 10 or more vectors corresponding to a principal component. In some embodiments, for example, either one or three vectors are created for the amino acid sequence of the protein or peptide subsequence within the protein. The vectors represent the mathematical properties of the amino acid sequence and are created by replacing the alphabetic coding for the amino acid with the relevant mathematical properties embodied in each of the three principal components.

D. Artificial Neural Network Regression.

In some embodiments, the present invention provides and utilizes probabilistic neural networks that predict peptidase cleavage sites. A neural network is a powerful data modeling tool that is able to capture and represent complex input/output relationships. The motivation for the development of neural network technology stemmed from the desire to develop an artificial system that could perform "intelligent" tasks similar to those performed by the human brain. Neural networks resemble the human brain in the following two ways: a neural network acquires knowledge through learning and a neural network's knowledge is stored within inter-neuron connection strengths known as synaptic weights (i.e. equations). Whether the principal components could be used in the context of a NN platform was tested, Some work has been reported recently using actual physical properties and neural networks in what is called a quantitative structure activity relationship (QSAR). See, e.g., Tian F, Lv F, Zhou P, Yang Q, Jalbout A F (2008) Toward prediction of binding affinities between the MHC protein and its peptide ligands using quantitative structure-affinity relationship approach. Protein Pept Lett 15: 1033-1043; Tian F, Yang L, Lv F, Yang Q, Zhou P (2009) In silico quantitative prediction of peptides binding affinity to human MHC molecule: an intuitive quantitative structure-activity relationship approach. Amino Acids 36: 535-554; Huang R B, Du Q S, Wei Y T, Pang Z W, Wei H, et al. (2009) Physics and chemistry-driven artificial neural network for predicting bioactivity of peptides and proteins and their design. J Theor Biol 256: 428-435. S0022-5193(08)00450-5 [pii]; 10.1016/j.jtbi.2008.08.028 [doi]. One of these articles used a huge array of physical properties in conjunction with complex multilayer neural networks. However, method using physical properties directly suffers a major drawback in that there is really no way to know, or even to assess, what is the correct weighting of various physical properties. This is a major constraint as it is well known that the ability of NN to make predictions depends on the inputs being properly weighted (Bishop, C. M. (1995), Neural Networks for Pattern Recognition, Oxford: Oxford University Press. Patterson, D. (1996). Artificial Neural Networks. Singapore: Prentice Hall. Speckt, D. F. (1991). A Generalized Regression Neural Network. IEEE Transactions on Neural Networks 2 (6), 568-576.). Besides simplifying the computations, appropriate weighting is a fundamental advantage of using the principal components of amino acids as proxies for the physical properties themselves. As FIG. 14 shows, the first three principal components accurately represent nearly 90% of all physical properties measured in 31 different studies.

Multi-layer Perceptron Design.

Figure 7:
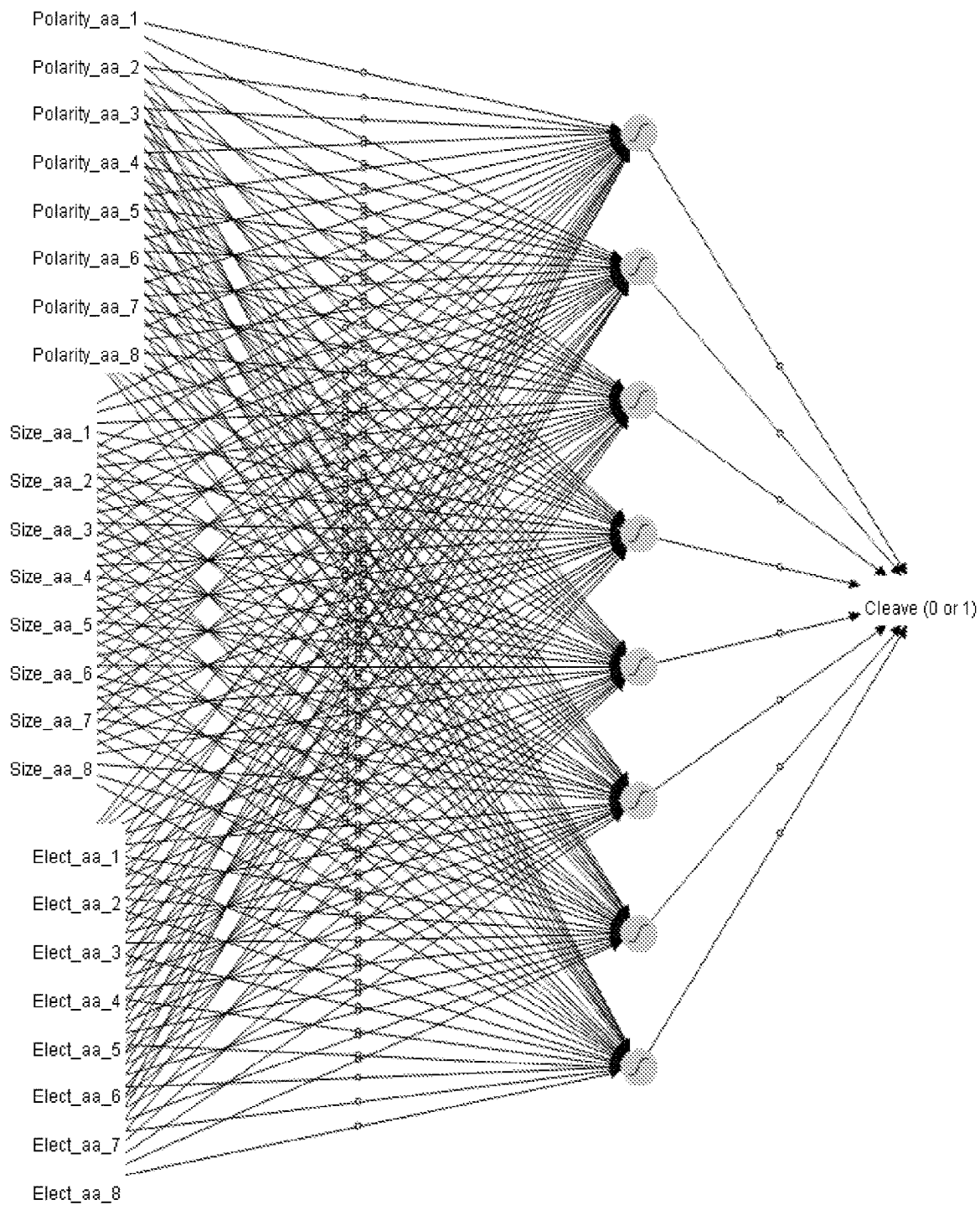

In some embodiments, one or more principal components of amino acids within a peptide of a desired length are used as the input layer of a multilayer perceptron network. In some embodiments, the output layer is the probability of peptidase cleavage. In some embodiments, the first three principal components in Table 3 were deployed as three uncorrelated physical property proxies as the input layer of a multi-layer perceptron (MLP) neural network (NN) regression process (4) the output layer of which is a diagram depicting the design of the MLP is shown in FIG. 7. The overall purpose is to produce a series of equations that allow the prediction of the probability of cleavage using the physical properties of the amino acids in the peptide n-mer under consideration as input parameters. In preferred embodiments the n-mer is an octomer representing the peptidase enzyme binding groove. Clearly more principal components could be used, however, the first three proved adequate for the purposes intended.

A number of decisions must be made in the design of the MLP. One of the major decisions is to determine what number of nodes to include in the hidden layer. For the NN to perform reliably, an optimum number of hidden notes in the MLP must be determined. There are many "rules of thumb" but the best method is to use an understanding of the underlying system, along with several statistical estimators, and followed by empirical testing to arrive at the optimum. The molecular binding groove comprising the active site of many peptidases has been understood to accommodate 8 amino acids. See, e.g., Schechter and Berger (1967).

In some embodiments, the number of hidden nodes is set to correlate to or be equal to the binding pocket domains. It would also be a relatively small step from PLS (linear) regression, but with the inherent ability of the NN to handle non-linearity providing an advantage in the fitting process. A diagram of the MLP for peptidase cleavage prediction is in FIG. 7.

Training Sets and NN Quality Control.

In developing NN predictive tools, a common feature is a process of cross validation of the results by use of "training sets" in the "learning" process. In practice, the prediction equations are computed using a subset of the training set and then tested against the remainder of the set to assess the reliability of the method. To establish the generalize-ability of the predictions, a random holdback cross validation procedure was used along with various statistical metrics to assess the performance of the NN.

A common problem with NN development is "overfitting", or the propensity of the process to fit noise rather than just the desired data pattern in question. There are a number of statistical approaches that have been devised by which the degree of "overfitting" can be evaluated. NN development tools have various "overfitting penalties" that attempt to limit overfitting by controlling the convergence parameters of the fitting. The NN platform in JMP®, provides a method of $r^2$ statistical evaluation of the NN fitting process for the regression fits. Generally, the best model is derived through a series of empirical measurements. As the output of the neural net is a categorical value, no standardization is needed.

E. Peptidases

The present invention provides predictions of cleavage sites at which peptidases cleave an amino acid sequence. The processes described herein can be applied to any class of peptidase, including, but not limited to endopeptidases, exopeptidases, intracellular peptidases, extracellular peptidases, endosomal peptidases, and lysosomal peptidases. In some embodiments, the peptidases are in enzyme classes 3.4.11, 3.4.12, 3.4.13, 3.4.14, 3.4.15, 3.4.16, 3.4.17, 3.4.18, 3.4.19, 3.4.20, 3.4.21, 3.4.22, 3.4.23, or 3.4.24 and include serine proteases, cysteine proteases, aspartic acid proteases, and metalloendopeptidases. In some embodiments, the peptidase is a cathepsin. Representative cathepsins include, but are not limited to, Cathepsin A (serine protease), Cathepsin B (cysteine protease), Cathepsin C (cysteine protease), Cathepsin D (aspartyl protease), Cathepsin E (aspartyl protease), Cathepsin F (cysteine proteinase), Cathepsin G (serine protease), Cathepsin H (cysteine protease), Cathepsin K (cysteine protease), Cathepsin L1 (cysteine protease), Cathepsin L2 (or V) (cysteine protease), Cathepsin O (cysteine protease), Cathepsin S (cysteine protease), Cathepsin W (cysteine proteinase), and Cathepsin Z (or X) (cysteine protease).

In preferred embodiments, the processes of the present invention are utilized to analyze amino acid sequences to determine whether the sequences contain a peptidase cleavage motif and to determine the identity and location of the motif. These process may be applied to amino acid sequence. In some embodiments, the amino acid sequence comprises the amino acid sequences of a class of proteins selected from the group derived from the proteome of pathogenic microorganisms. In other embodiments the amino acid sequences derive from a class of proteins selected from the group comprising allergens (including but not limited to plant allergen proteins and food allergens). In other embodiments the amino acid sequences derive from a class of proteins selected from the group comprising mammalian proteins including but not limited to tumor associated antigen proteins, proteins reactive in autoimmunity, enzymes and structural mammalian proteins. In other embodiments the amino acid sequences derive from a class of proteins selected from the group comprising synthetic and recombinantly manufactured proteins, including but not limited to biopharmaceuticals (e.g., replacement enzymes, clotting factors, monoclonal antibodies and antibody fusions) and industrial proteins (for example in food additives, textiles, wood). These examples however should not be considered limiting as the analytical approach can be applied to any peptidase of any species or source provided training sets can be developed experimentally by any means for that enzyme.

F. Summary of Peptidase Cleavage Prediction Methodology.

Several new proteomic techniques have recently been developed that identify newly created cleavage sites through isotopic or other labeling of the residues flanking the cleavage site, and mass spectrometry. These cleavage site labelling (CSL) techniques can characterize in a single experiment hundreds of times as many cleavage events as previously catalogued for a peptidase.

The active site of peptidases can be conceptualized as an enzyme binding pocket with 8 contiguous topographic subsites comprising the cleavage site octomer (CSO) are consecutively numbered outward from the cleavage site between P1 and P1' as P4-P3-P2-P1|P1'-P2'-P3'-P4'. The corresponding binding sites on the enzyme are numbered S4 . . . S4'.

As described herein, it is contemplated that PCAA can be used to develop classifiers for prediction of peptidase cleavage sites using the much larger datasets produced by the CSL proteomic processes and provided in the Supplemental materials of three recent publications (Biniossek, et al (2011); Impens, F. et al. (2010); Tholen, S. et al. (2011) above). The present invention utilizes a probabilistic neural network perceptron that is essentially a non-linear PLS regression (Bishop, 1995, above) provided in a widely used statistical program (JMP®) to develop the prediction equations. The present invention further utilizes a perceptron with mathematical symmetry to the biological subject, in this case the peptidase binding pocket. This process generates accurate predictions of cleavages for each of the peptidases studied.

In some preferred embodiments, non-redundant octomer datasets are derived from the CSL datasets, indexed by single amino acid displacement throughout the protein, and used for training the neural net. Non-redundant sets consisting of a single representatives of a particular CSO are preferably created because the presence of multiple copies of a particular cleaved peptide could be due either to parent protein abundance in the protein mixture used or because of the cleavability by a particular peptidase. Since all of the proteins in these experimental sets were exposed to the peptidase for extended periods of time and only a relatively small number of sites were cleaved, the non-cleaved peptides were assumed to be true negatives for classifier training purposes.

The peptidase prediction output is a binary categorical variable (cleave/no-cleave) rather than a continuous real number as in MHC binding affinity prediction (i.e. natural logarithm $ic_{50}$). The perceptron is the topological description of the underlying mathematical equation lattice comprising a neural network. For this purpose, the present invention utilizes a relatively simple perceptron having a single input layer which comprises the amino acid principal component vectors, a single layer of hidden nodes and a single binary output that is the predicted probability of cleavage coded as a zero or one. The number of hidden nodes is preferably fixed at eight, providing symmetry between the mathematics of the perceptron and the conceptual underlying enzyme binding pocket.

The PCAA are preferably derived by eigen decomposition of the correlation matrix of 31 different studies as described above. It is contemplated that use of the correlation matrix as a foundation makes it possible to combine the results of a wide variety of studies with different scoring metrics to create a composite set of vectors that are mutually orthogonal (i.e. uncorrelated), zero-centered, and appropriately weighted for their relative contributions. The peptidase cleavage datasets provided by the CSL studies have 500 to 3000 cleaved peptides that exceeded the detection limit of mass spectrometry for each experimental conditions in a total of up to approximately 800 identified proteins. For cathepsin L, training sets resulting from three different experimental conditions were used, and for cathepsin S, training sets resulting from two different experimental conditions were used. The conditions of cleavage under which the experiments that produced the training sets were done at pH 6 (cathepsin L and cathepsin S) and pH7.5 (cathepsin S) to represent the range pH conditions found in the endosome compartments at different stages of antigen processing.

In preferred embodiments, the present invention encompasses creating small, balanced subsets for training (bootstrap aggregation, "bagging") and validation of the classifiers and then using the resulting predictors for larger datasets. Preferably, a 5 k-fold cross validation is performed 5 times, each time starting with a different seed for the random number generator.

In some preferred embodiments, ensembles of 25 discriminant equations are produced for each amino acid found at the P1 and P1' position of the CSO. As nearly every amino acid (of the 20 possible) is found at each of those positions up to nearly 1000 total discriminant equations are produced for each experimental set. Each of the members of the ensemble preferably comprises a randomly selected, independent predictor of the probability of the cleavage of a peptide at a certain P1-P1' pair based on the combinatorial amino acids in the flanking positions. These equations perform very well with a true positive rate of approximately 90% and a false positive rate of about 10%. In preferred embodiments, probabilities from the multiple different training sets are combined and the maximum probability of the group of predictions is used as the metric (cathepsin L=six total predictions, P1 and P1' for 3 different experimental conditions; cathepsin S=four total predictions, P1 and P1' for 2 experimental conditions).

G. Applications

The processes of the present invention are useful for a wide variety of applications.

In some preferred embodiments, the processes described above provide the location and identity of peptidase cleavage motifs in a target protein or polypeptide (referred to hereafter as the target polypeptide). The present invention provides further processes wherein the target polypeptides are modified based on this information. In some embodiments, the target polypeptide is modified to mutate the peptidase cleavage motif so that the resulting mutated target polypeptide is not cleaved by the peptidase at or in proximity to the mutated site. In other embodiments, the target polypeptide is modified to include a peptidase cleavage motif for a particular peptidase(s) at a defined site within the target polypeptide. In some embodiments, these modifications are utilized to alter the degradation of protein, and in some preferred embodiments, the degradation of a protein that is utilized as a drug. In some embodiments, the target polypeptide comprises an active polypeptide (e.g., the polypeptide is a prodrug) and is modified to include a peptidase cleavage motif to facilitate release of the active polypeptide. Thus, the present invention encompasses design of polypeptides that are cleaved by particular peptidases and at sites within or outside the body where specific peptidases are expressed.

In some embodiments determination of the cleavage site is used in selecting a polypeptide for inclusion in an immunogen or vaccine, such that the immunogen will be cleaved predictably for binding by an MHC molecule and presentation at the cell surface to a T cell receptor and hence stimulate immunity, or such that a B cell epitope is bound to a B cell receptor and internalized by the B cell. In some embodiments said immunogenic peptide is selected to provide a cleavage site 4, or 5 or 6 or up to 20 amino acids from the N terminal or the C terminal of the selected peptide. In some embodiments the peptide is selected such that the predicted cleavage site is separated from the immunogenic peptide by flanking regions of 1, or 2 or 3 or up to 20 amino acids.

In other embodiments, the polypeptide to be included in an immunogen or vaccine is modified by standard cloning and genetic engineering techniques to include a peptidase cleavage motif for a particular peptidase(s) at a defined site within the polypeptide. In some preferred embodiments, the defined site flanks an amino acid sequence that is a B cell epitope or is otherwise recognized by an MHC molecule for presentation at the cell surface to a T cell receptor and stimulation of immunity.

In some embodiments, the processes described herein are utilized to design peptidase inhibitors. As described above, the present invention utilizes principal components analysis and neural networks to identify amino acid sequences that interact with binding pocket of a peptidase. In some embodiments, the process are utilized to identify molecular entities (such as small molecule drugs, peptide or polypeptides) that interfere with or modulate the interaction between the peptidase binding pocket of a peptidase and its preferred peptidase cleavage motif which is located in a target polypeptide acted on by the peptidase. For example, the present invention may be utilized to design peptides which block the peptidase binding pocket or which interfere with binding to the peptidase binding pocket.

In other embodiments, the processes described herein are used to determine the potential side effects of protease inhibitors by predicting the downstream impact of protease inhibition on proteins other than the target protein.

In preferred embodiments, PCAA is used in a numerical method to predict peptidase cleavage patterns. Bremel, R. D. & Homan, E. J. An integrated approach to epitope analysis I: Dimensional reduction, visualization and prediction of MHC binding using amino acid principal components and regression approaches. Immunome. Res. 6, 7 (2010); Bremel, R. D. & Homan, E. J. An integrated approach to epitope analysis II: A system for proteomic-scale prediction of immunological characteristics. Immunome. Res. 6, 8 (2010). The process described herein makes it possible to utilize the large datasets produced by CSL in a straightforward way as training sets for developing peptidase cleavage predictors. As a least squares fitting process using numerical input vectors, it should be relatively immune to the types of peptide-similarity bias that have emerged as a problem in the use of alphabetic representations of peptides and the use of categorical predictors. Yang, Z. R. Prediction of caspase cleavage sites using Bayesian bio-basis function neural networks. Bioinformatics. 21, 1831-1837 (2005). The z-scale vectors used as predictors were derived by eigen decomposition of the correlation matrix between a large number of studies on the biophysical properties of amino acids. Bremel, R. D. & Homan, E. J. An integrated approach to epitope analysis I: Dimensional reduction, visualization and prediction of MHC binding using amino acid principal components and regression approaches. Immunome. Res. 6, 7 (2010). This process is fundamentally a dimensional reduction that produces a set of numbers that are proxy variables. The first two z-scale vectors have obvious relationships to familiar biophysical properties of amino acids. These dimensionless numerical predictors have several additional characteristics; most importantly they are uncorrelated and thus unique predictors and they are appropriately scaled within and among each other. Use of correlated and inappropriately scaled predictors can lead to biases in predictions due to scale effects in the underlying algorithms which are an issue to consider in the many amino acid based prediction schemes that have been described. Bishop, C. M. Neural Networks for Pattern Recognition (Oxford University Press, Oxford, 1995); Beck, H. et al. Cathepsin S and an asparagine-specific endoprotease dominate the proteolytic processing of human myelin basic protein in vitro. Eur. J. Immunol. 31, 3726-3736 (2001). Du, Q. S., Wei, Y. T., Pang, Z. W., Chou, K. C., & Huang, R. B. Predicting the affinity of epitope-peptides with class I MHC molecule HLA-A*0201: an application of amino acid-based peptide prediction. Protein Eng Des Sel 20, 417-423 (2007). The methods of the present invention also avoid the issues and complexities that arise in development of rule based systems. Rognvaldsson, T. et al. How to find simple and accurate rules for viral protease cleavage specificities. BMC. Bioinformatics. 10, 149 (2009). The methods of the present invention have been illustrated for several cathepsins, however the concepts should be broadly applicable to peptidases in general. Overall the performance of the predictors, in terms of the specificity and sensitivity, are similar to those of signal peptidase predictors which are routinely used for identification of signal peptides in genome curation and for pattern classifiers in general (see FIG. 12a-c). Choo, K. H., Tan, T. W., & Ranganathan, S. A comprehensive assessment of N-terminal signal peptides prediction methods. BMC. Bioinformatics. 10 Suppl 15, S2 (2009). A rule-based approach such as POPS uses PSSM in conjunction with various biophysical properties to produce cleavage probability predictions. Boyd, S. E., Pike, R. N., Rudy, G. B., Whisstock, J. C., & Garcia, d. l. B. PoPS: a computational tool for modeling and predicting protease specificity. J. Bioinform. Comput. Biol. 3, 551-585 (2005). A wide variety of systems are available for prediction of many different protein physical properties and, in general, an indexing window is used to produce numerical metrics attributable to the particular biophysical property. To the extent that the cleavage probability is related to physical properties of amino acids in the CSO, the multi-dimensional PCAA using z-scale vectors should also capture those biophysical properties and, thus, this approach also embodies elements of some of the other secondary predictors used in rule-based approaches. The CSL input datasets used for this analysis each provided data only for two reaction time points. However, with sufficient time points in an experimental protocol, the approach could be extended to produce a kinetic estimate and thus predict the rate of cleavage of different CSO.

Several different proteomic and combinatorial library cleavage analytic techniques have been developed recently. The methods derive their power from being able to cross-reference mass spectrometer fragmentation patterns with translated genomic data to identify peptidase target sequences from peptide fragmentation patterns. Approaches like "proteome identification of cleavage specificity" (PICS) or "isobaric tags for relative and absolute quantification terminal amine isotopic labeling" (iTRAQ-TAILS) "stable isotope labeling of amino acids in culture" (SILAC), can be used to characterize very large numbers of cleavage events. Biniossek, M. L., Nagler, D. K., Becker-Pauly, C., & Schilling, O. Proteomic identification of protease cleavage sites characterizes prime and non-prime specificity of cysteine cathepsins B, L, and S. J. Proteome. Res. 10, 5363-5373 (2011); Impens, F. et al. A quantitative proteomics design for systematic identification of protease cleavage events. Mol. Cell Proteomics. 9, 2327-2333 (2010); Tholen, S. et al. Contribution of cathepsin L to secretome composition and cleavage pattern of mouse embryonic fibroblasts. Biol. Chem. 392, 961-971 (2011). The combinatorial complexity of the amino acid frequencies in the CSO of the cathepsin cleavage products is enormous; virtually every amino acid is found in every position of the CSO and for any particular peptidase, the amino acid frequency in the CSO diverges significantly from the overall frequency in proteins only at a few positions. The ever-increasing size of the databases generated by CSL techniques has illuminated the inadequacies of the general catalogs of cleavage sites previously developed from very limited experimentation. Earlier attempts to develop prediction algorithms with as few as 13 cleavage products are now overshadowed by experimental procedures that generate thousands of cleavage products. Yang, Z. R. Prediction of caspase cleavage sites using Bayesian bio-basis function neural networks. Bioinformatics. 21, 1831-1837 (2005). While heat diagrams or alphabetic logos are useful, and do provide an impression of amino acid preferences in the CSO, they are of limited utility in development of prediction tools. Colaert, N., Helsens, K., Martens, L., Vandekerckhove, J., & Gevaert, K. Improved visualization of protein consensus sequences by iceLogo. Nat. Methods 6, 786-787 (2009); Rigaut, K. D., Birk, D. E., & Lenard, J. Intracellular distribution of input vesicular stomatitis virus proteins after uncoating. J. Virol. 65, 2622-2628 (1991). Database approaches are inherently limited to detecting direct matches, but can be expanded somewhat with rule-sets and sufficiently large databases. Schilling, O. & Overall, C. M. Proteome-derived, database-searchable peptide libraries for identifying protease cleavage sites. Nat. Biotechnol. 26, 685-694 (2008); Song, J. et al. Bioinformatic approaches for predicting substrates of proteases. J. Bioinform. Comput. Biol. 9, 149-178 (2011); Schilling, O., auf dem, K. U., & Overall, C. M. Factor Xa subsite mapping by proteome-derived peptide libraries improved using WebPICS, a resource for proteomic identification of cleavage sites. Biol. Chem. 392, 1031-1037 (2011). Rule based systems have been successfully employed with peptidases with relatively specific CSO sequence requirements. Rognvaldsson, T. et al. How to find simple and accurate rules for viral protease cleavage specificities. BMC. Bioinformatics. 10, 149 (2009). Rule-extraction for combinatorial patterns like those seen with the cathepsins used here, where all the frequencies are nearly equivalent, may be intractable.

Endosomal peptidases only generate a few cleavages (several thousand) from among a very large potential number of octomers (several hundred thousand) in a protein mixture. This low frequency, when combined with the combinatorial complexity, is a challenge in developing prediction tools an issue that has been recently reviewed by Chou. Chou, K. C. Some remarks on protein attribute prediction and pseudo amino acid composition. J. Theor. Biol. 273, 236-247 (2011). However, substantial research has gone into development of algorithmic approaches to deal with low frequency events in other fields. Chawla, N., Lazarevic, A., Hall, L., & Bowyer, K. SMOTEBoost:

Improving prediction of the minority class in boosting. Knowledge Discovery in Databases: PKDD 2003107-119 (2003); Chawla, N., Eschrich, S., & Hall, L. O. Creating ensembles of classifiers. Data Mining, 2001.ICDM 2001, Proceedings IEEE International Conference, 580-581. 2001; Chawla, N. V. Data mining for imbalanced datasets: An overview. Data Mining and Knowledge Discovery Handbook875-886 (2010). Generating multiple ensembles of prediction equations through the local optimization training process is preferred for producing predictions with useful sensitivity and specificity. Cieslak, D. A. & Chawla, N. V. Start globally, optimize locally, predict globally: Improving performance on imbalanced data. Data Mining, 2008.ICDM'08. Eighth IEEE International Conference, 143-152. 2008; Lichtenwalter, R. & Chawla, N. Adaptive methods for classification in arbitrarily imbalanced and drifting data streams. New Frontiers in Applied Data Mining53-75 (2010); Tang, Y., Zhang, Y. Q., Chawla, N. V., & Krasser, S. SVMs modeling for highly imbalanced classification. Systems, Man, and Cybernetics, Part B: Cybernetics, IEEE Transactions on 39, 281-288 (2009). Furthermore, in preferred embodiments, reducing the dimensionality of the datasets by the use of anchor residues in the CSO is a helpful simplification. Although it adds data processing complexity, a process in which prediction equation ensembles are derived individually for each of the different amino acids found at both the P1 and the P1' anchor positions provides for an independence of the predictor output probabilities and thus an increased confidence level in the results.

An additional complication, related to the low frequency of actual cleavages relative to the potential cleavages, is whether the uncleaved CSO are valid "true negatives" that are essential for development of any binary classifier prediction tool. All the non-cleaved octomers are preferably chosen as true negatives but it is a source of potential bias particularly for several of the datasets derived from degradomic approaches. Impens, F. et al. A quantitative proteomics design for systematic identification of protease cleavage events. Mol. Cell Proteomics. 9, 2327-2333 (2010); Tholen, S. et al. Contribution of cathepsin L to secretome composition and cleavage pattern of mouse embryonic fibroblasts. Biol. Chem. 392, 961-971 (2011). Peptide-centric approaches such as used for the human cathepsin B, L, and S data sets are actually designed to delineate the active site specificity. Biniossek, M. L., Nagler, D. K., Becker-Pauly, C., & Schilling, O. Proteomic identification of protease cleavage sites characterizes prime and non-prime specificity of cysteine cathepsins B, L, and S. J. Proteome. Res. 10, 5363-5373 (2011). Degradomic procedures such as those used to produce the cathepsin D, E, and murine L datasets, are thought to be less suitable to subsite mapping studies. Impens et al., Tholen et al., Schilling, O. & Overall, C. M. Proteome-derived, database-searchable peptide libraries for identifying protease cleavage sites. Nat. Biotechnol. 26, 685-694 (2008). Cathepsins have been studied for many years and the many studies were reviewed recently by Turk et al. Turk, V. et al. Cysteine cathepsins: from structure, function and regulation to new frontiers. Biochim. Biophys. Acta 1824, 68-88 (2012). Structural studies of the enzymes suggest that for cleavage to occur the CSO peptide must assume an extended configuration within the active site cleft. Turk et al. Pretreatment with one peptidase may release shorter peptides, making CSO's more accessible to a second peptidase.

Thus, one can envision that a single cathepsin enzyme working in isolation on intact protein molecules might have difficulty in accessing certain P1-P1' pairs, even though those pairs might be cleavable if presented to the enzyme as an extended free peptide. It is therefore likely that an isolated cathepsin will give an underestimate of the number of actual cleavages of which that enzyme might be capable in an optimal milieu. For example, cleavage of HIV GP120, a protein of 525 amino acids, by three different cathepsins individually produces a relatively small set of approximately 10 total peptides, some of them redundantly produced by the different enzymes. Yu, B., Fonseca, D. P., O'Rourke, S. M., & Berman, P. W. Protease cleavage sites in HIV-1 gp120 recognized by antigen processing enzymes are conserved and located at receptor binding sites. J. Virol. 84, 1513-1526 (2010). By comparison, Beck et al. using several cathepsins in combination obtained over 60 peptides from the much smaller C-terminal half of myelin basic protein which comprises 170 amino acids. Beck, H. et al. Cathepsin S and an asparagine-specific endoprotease dominate the proteolytic processing of human myelin basic protein in vitro. Eur. J. Immunol. 31, 3726-3736 (2001). In the CSL process used by Binniosek et al. individual enzymes of interest are given access over an extended period to a peptide library produced by prior cleavage of a protein mixture by a different peptidase. Under these circumstances it seems reasonable to assume that all the potential scissile bonds were available to the peptidase under evaluation, and thus all the non-cleaved CSOs are true negatives. The datasets produced in more biological models, where the test peptidase is operating on a protein mixture such as a secretome, the situation is different and the peptidases might not have had access to all potential scissile bonds. Tholen et al., Impens et al. Here the use of uncleaved CSOs as true negatives might be problematic. This could possibly be verified by direct experimentation using the PIC approach on the same protein mixtures, but the lower specificities and sensitivities (approx. 0.8) seen with the degradomic data sets are consistent with there being a number of true positives still present among the uncleaved CSOs and which were inaccessible to the enzyme and thus inappropriately bias the predictors.

An additional consideration in choosing the true negatives from an experimental approach like that of Binniossek et al is whether one should create the true negative CSO training set in silico by a two-step approach also: first cleave by a first enzyme (i.e. trypsin) in silico and then derive negative CSOs from the resulting shorter peptides rather than the intact proteins. In preferred embodiments, this is not done because it is not clear that the cleavage by trypsin is sufficiently exhaustive to cleave at all possible sites. Further, use of the independent P1 and P1' predictors means that cleavage predictions can be generated for peptides with a K or R in the P1 position based on the P1' predictor, while these cleavage sites would be destroyed by trypsin. Information from other studies indicates that each of the cathepsins used also cleave peptides with a K or R in the P1 position. Beck, H. et al. Cathepsin S and an asparagine-specific endoprotease dominate the proteolytic processing of human myelin basic protein in vitro. Eur. J. Immunol. 31, 3726-3736 (2001); Rawlings, N. D., Barrett, A. J., & Bateman, A. MEROPS: the database of proteolytic enzymes, their substrates and inhibitors. Nucleic Acids Res. 40, D343-D350 (2012).

Development of pattern classification tools is an empirical process. Duda, R. O., Hart, P. E., & Stork, D. G. Pattern Classification (John Wiley & Sons, Inc., 2001). The results presented herein were obtained with one specific classification tool, a probabilistic neural net built in the context of the JMP platform. Nominally similar software platforms can produce potentially widely disparate results. Chou, K. C.

Some remarks on protein attribute prediction and pseudo amino acid composition. J. Theor. Biol. 273, 236-247 (2011). Because of the nature of the underlying algorithms and the stochastic way that they are implemented, it must be recognized that every software package will likely produce different results with a different degree of accuracy. There are many ways to implement a neural network algorithm and the results may differ substantially in detail. DTREG (dtreg.com) is a commercial source of a number of different prediction tools and the comparisons that this software supplier provides for different packages with benchmark datasets (dtreg.com /benchmarks.htm) are instructive as to the variation in the predictions that can be expected from different packages (see FIG. 12a-c). During the development of the present invention, several packages were downloaded from www.dtreg.com and utilized for testing, focusing on classifiers that had cross-validation and control features comparable to the JMP® platform. The area under the receiver operating curve (AROC) was utilized as a comparison metric and found that the probabilistic neural net predictor using a radial basis activation function and a support vector machine (SVM) that uses the same activation function as the JMP® neural network produced results comparable to the JMP® probabilistic neural net. A SVM is generally considered to be less susceptible to overfitting. Interestingly, the SVM seemed to provide somewhat better performance with those cathepsin D and E amino acid anchors that were problematic for the JMP® platform (FIG. 12). The SVM found in the e1071 package in the R statistical platform (http://www.r-project.org/, FIG. 13) was tested with an equivalent training approach and its performance was generally comparable to the JMP neural net. The conceptual symmetry between the neural net perceptron structure and the active site is useful as a "reasoning environment". Boyd, S. E., Pike, R. N., Rudy, G. B., Whisstock, J. C., & Garcia, d. l. B. PoPS: a computational tool for modeling and predicting protease specificity. J. Bioinform. Comput. Biol. 3, 551-585 (2005). Although the SVM produces accurate predictions they are produced by hundreds of support vectors in multidimensional space, which does not provide a means to translate the output directly to experimental work.

Issues related to the false discovery (false positive) rate of in silico peptidase cleavage predictors have been discussed elsewhere. Schilling, O. & Overall, C. M. Proteome-derived, database-searchable peptide libraries for identifying protease cleavage sites. Nat. Biotechnol. 26, 685-694 (2008). The false discovery rate shown in FIG. 4 (FP) varies depending on the amino acids at P1 and P1' and also varies between different peptidases but is generally about 10%. This is among the better of the error rates of a number of widely used classifiers with benchmark data sets (FIG. 12)

In summary, a mathematical process has been described for using proteomic data in combination with the statistical principles of principal component analysis, partial least squares regression and machine learning algorithms to develop predictors for peptidase cleavage. Results were shown for several cathepsins but the approach is extensible and should be broadly applicable to any type of peptidase enzyme. Tools that enable predictions beyond the protein sets that have been used in experiments will have a number of practical uses. With a process based on mathematical formulae, simulators can readily be constructed to predict cleavage of theoretical sequences and to assist or complement other experimental work.

EXAMPLES

To examine whether the predictions of peptidase cleavage sites derived from the computer based analytical process described herein, were correlated with data from experimental characterization of cleavage sites described in the scientific literature, the inventors conducted a number of analyses as described below.

Example 1

Correlation with Results Obtained by CSL Techniques

Here the inventors show that PCAA can be used as the basis for developing classifiers for prediction of proteolytic cleavage sites using the much larger datasets produced by the CSL proteomic processes in three recent publications (Impens et al., Tholen et al., Biniossek et al., referenced above) and provided in Supplemental datasets of these publications are used to demonstrate the principle of the technique for human Cathepsin B, L, and S and murine Cathepsin D in E, and L. These lysozomal (endosomal) peptidases are each thought to play roles in proteolytic processing for MHC display on the surface of antigen presenting cells as well as a variety of other physiological functions. A probabilistic neural network perceptron that is essentially a non-linear PLS provided in a widely used statistical program (JMP®) is used as the basis for developing the prediction equations. A perceptron is utilized which has a mathematical symmetry to the biological subject, in this case the binding pocket of peptidase. The inventors show that the process is capable of producing accurate predictions of proteolytic cleavages for each of the peptidases studied. The inventors further show that by weighting the physical properties at different positions within the CSO, the performance of the predictions can be improved. Predictor outputs are also compared to experimental results in the literature for myelin basic protein.

Datasets comprising non-redundant CSOs indexed by a single amino acid were derived (FIG. 8) from protein sequences identified in three recent publications and all peptides were given a binary code (0,1) depending on whether or not they had been cleaved or not between the P1 and P1'. See Biniossek et al., Impens et al., Tholen et al. For the analysis described below alphabetic peptide sequences were converted into z-scale numerical vectors following the general method of using PCAA described recently to develop predictors of peptide binding to MHC molecules. Bremel, R. D. & Homan, E. J. An integrated approach to epitope analysis I: Dimensional reduction, visualization and prediction of MHC binding using amino acid principal components and regression approaches. Immunome. Res. 6, 7 (2010); Bremel, R. D. & Homan, E. J. An integrated approach to epitope analysis II: A system for proteomic-scale prediction of immunological characteristics. Immunome. Res. 6, 8 (2010). The approach is based on use of the first 3 principal component z scale vectors, wherein $z_1$ is related to polarity/hydrophobicity, $z_2$ is related to size, and $z_3$ related to the electronic character of the amino acid. Below statistics and patterns of these z-scale vectors within the CSO are described and the inventors further demonstrate their use in a probabilistic neural net classifier for prediction of peptidase cleavage.

Data Sets

The datasets used are from supplemental data tables in three recent publications Biniossek et al., Impens et al., Tholen et al. The proteins identified in these tables were downloaded from Genbank based on identifiers provided by the authors. Non-redundant octomer datasets, indexed by single amino acid displacement throughout the protein, were created and used for training the neural net as described below. Non-redundant sets were created because the presence of multiple copies of a particular cleaved peptide could be due either to parent protein abundance in the protein mixture used or because of the cleavability by a particular peptidase. Since all of the proteins in these experimental sets were exposed to the peptidase for extended periods of time and only a relatively small number of sites were cleaved, the non-cleaved peptides were assumed to be "true negatives" for classifier training purposes Probabilistic Neural Network (NN)

To develop a peptidase prediction pattern classification system an approach was used that is analogous to that used for predictions of peptide binding affinity for MHC I and MHC II. In the current situation, however, the prediction output was a binary categorical variable (cleave/no-cleave) rather than a continuous real number (i.e. binding affinity). The perceptron is the topological description of the underlying mathematical equation lattice comprising a neural network. Many possible configurations of perceptron can be constructed with different numbers of layers and inputs. A diagram of the perceptron used is shown in FIG. 7. This is a relatively simple perceptron, having a single input layer which comprises the amino acid principal component vectors, a single layer of hidden nodes and a single binary output that is the predicted probability of cleavage coded as a zero or one. The lines connecting the different portions of the perceptron represent "activation functions". For the work described, the sigmoidal hyperbolic tangent activation function was used. The number of hidden nodes was fixed at eight providing symmetry between the mathematics of the perceptron and the underlying enzyme binding pocket conceptualization. In addition the symmetry between the mathematics and the molecular characteristics enables use of the simulation tools provided within the JMP® application to have direct and obvious relationships to potential experimental work.

Principal Components as Input to the Neural Net

The principal components of amino acid physical properties were derived by eigen decomposition of the correlation matrix of 31 different studies as described previously. Bremel, R. D. & Homan, E. J. An integrated approach to epitope analysis I: Dimensional reduction, visualization and prediction of MHC binding using amino acid principal components and regression approaches. Immunome. Res. 6, 7 (2010). Use of the correlation matrix as a foundation makes it possible to combine the results of a wide variety of studies with different scoring metrics to create a composite set of vectors that are mutually orthogonal (i.e. uncorrelated), zero-centered, and appropriately weighted for their relative contributions. The latter characteristic is the reason principal components are used as weighting factors for regression analysis. The relationship of the principal components to well-known biophysical characteristics is readily seen in the z-scale vectors in Table 3. The first principal component ($z_1$) is a polarity/hydrophobicity metric, the second principal component ($z_2$) a size metric, and the third principal component ($z_3$) embodies electronic characteristics of each amino acid. Bremel, R. D. & Homan, E. J. An integrated approach to epitope analysis I: Dimensional reduction, visualization and prediction of MHC binding using amino acid principal components and regression approaches. Immunome. Res. 6, 7 (2010); Bremel, R. D. & Homan, E. J. An integrated approach to epitope analysis II: A system for proteomic-scale prediction of immunological characteristics. Immunome. Res. 6, 8 (2010). The principal component proxy variables are a unique type of descriptor. They are real numbers with many significant figures from the eigen decomposition process but they have discrete quantized values. When used as descriptors for a peptide three numbers, the first three principal components, are used for each amino acid and these numbers assume various combinatorial sets within peptides.

TABLE 3

First three principal components of amino acid physical properties "z-scale" vectors derived from the correlation matrix of 31 different studies. Bremel, R. D. & Homan, E. J. An integrated approach to epitope analysis I: Dimensional reduction, visualization and prediction of MHC binding using amino acid principal components and regression approaches. Immunome. Res. 6, 7 (2010).

| Amino acid | z1 | Amino acid | z2 | Amino acid | z3 |
|---|---|---|---|---|---|
| K | −6.68 | W | −3.50 | C | −3.84 |
| R | −6.30 | R | −2.93 | H | −1.94 |
| D | −6.04 | Y | −2.06 | M | −1.46 |
| E | −5.70 | F | −1.53 | E | −1.46 |
| N | −4.35 | K | −1.32 | R | −0.91 |
| Q | −3.97 | H | −1.00 | V | −0.35 |
| S | −2.65 | Q | −0.47 | D | −0.18 |
| H | −2.55 | M | −0.43 | I | 0.04 |
| T | −1.43 | P | −0.36 | F | 0.05 |
| G | −0.76 | L | −0.20 | Q | 0.15 |
| P | −0.03 | D | 0.03 | W | 0.16 |
| A | 0.72 | N | 0.22 | N | 0.30 |
| C | 2.11 | I | 0.29 | Y | 0.37 |
| Y | 2.58 | E | 0.34 | T | 0.94 |
| M | 4.14 | T | 0.80 | K | 1.16 |
| V | 4.79 | S | 1.84 | L | 1.17 |
| W | 5.68 | V | 1.98 | G | 1.21 |
| L | 6.59 | A | 2.48 | S | 1.30 |
| I | 6.65 | C | 2.74 | A | 1.42 |
| F | 7.19 | G | 3.08 | P | 1.87 |

Training Sets

The peptidase cleavage data provided by the CSL studies is imbalanced in multiple ways. When decomposed into successive octomers indexed by one amino acid, the protein datasets used have between 350,000 to 550,000 non-cleaved octomers, or a vast excess over the 500 to 3000 cleaved peptides. A second layer of complexity derives from the differing frequencies at which any P1-P1' pair is cleaved compared to another dipeptide, overlaid on the differing abundance of each dipeptide pair. The fundamental issue is how to "train" and validate the classifiers appropriately with the number of non-cleavage events vastly outnumbering the cleavage events. Low frequency events are not an uncommon problem and various strategies have been developed for dealing with this situation. Chawla et al have done considerable work on the issue. Tholen, S. et al. Contribution of cathepsin L to secretome composition and cleavage pattern of mouse embryonic fibroblasts. Biol. Chem. 392, 961-971 (2011); Schechter, I. & Berger, A. On the size of the active site in proteases. I. Papain. Biochem. Biophys. Res. Commun. 27, 157-162 (1967); Ng, N. M. et al. The effects of exosite occupancy on the substrate specificity of thrombin. Arch. Biochem. Biophys. 489, 48-54 (2009); Boyd, S. E., Pike, R. N., Rudy, G. B., Whisstock, J. C., & Garcia, d. l. B. PoPS: a computational tool for modeling and predicting protease specificity. J. Bioinform. Comput. Biol. 3, 551-585 (2005). An approach shown to produce robust results for diverse situations is to "optimize locally and apply globally" by creating small, balanced subsets (ensembles) for training and validation of the classifiers and then using the resulting predictors for larger datasets. The general scheme for ensemble assembly is shown in and in FIG. 8. A relatively exhaustive 5×5×5-fold cross validation scheme based on concepts outlined in Cieslak and Chawla was utilized. Cieslak, D. A. & Chawla, N. V. Start globally, optimize locally, predict globally: Improving performance on imbalanced data. Data Mining, 2008.ICDM'08. Eighth IEEE International Conference on, 143-152. 2008. IEEE.

As shown in FIG. 8 a total of five ensembles of cohort trainer sets were created for each of the possible anchor amino acids. The training cohorts are anchored and balanced by pairing each amino acid at the P1 or P1' position or with a number of peptides (N) from the non-cleaved set having the identical P1, P1' or (dipeptide) P1-P1'. The choice of N is an empirical one and after experimentation N=4 was chosen as an approach providing an excess of non-cleaved peptides for adequate training while limiting over-fitting in the 5 k-fold cross validation scheme. Thus, for each ensemble cohort with a particular P1 or P1' amino acid, the cleaved peptides were combined with 4 times as many uncleaved peptides sharing amino acids at the matching the anchor positions. Each of the cohort sets uses the same cleaved peptides with different non-cleaved trainers. Then a 5 k-fold cross validation was performed 5 times, each time starting with a different seed for the random number generator. With this scheme a random 80 percent of the uncleaved plus cleaved ensemble cohorts sets are used repeatedly during training and tested on the remaining 20 percent to produce a discriminant prediction equation on convergence of the underlying algorithms that operate using a standard least-squared fitting process. Then, using the same ensemble but with a different random number seed, a different cohort set (of 80%) is selected and another prediction equation is produced. Random number generators produce defined sequences of random numbers, so initiating the process with a different seed effectively defines a different path to convergence of the algorithms. This process is repeated a total of 5 times for each ensemble and therefore, by use of the 5 different ensembles, a total of 25 different discriminant equation sets (positive and negative predictions) were produced. Each equation set produces its own unique and independent cleavage probability estimate. Importantly, the non-cleaved negative trainers, in each cohort were unique to each of the five cohorts and the prediction equations produced for that cohort had not "seen" the peptides used by the other cohorts until the final stage of cross validation where the equations were tested against the other four sets of non-cleaved peptides.

Principal Component Patterns within the Cleavage Site Octomer

For the peptidases under consideration, nearly every amino acid can found at every position of the CSO. The utility of using an anchoring amino acid at subsite P1 was recognized based on examination of the some of the underlying statistics of the z-scale vectors of the cleaved peptides compared to uncleaved peptides. FIGS. 1 and 2 demonstrate the patterns that emerge from analysis of the mean and variance. FIG. 1 shows the analysis of peptides within the CSO for human and murine cathepsin L. The differences between cleaved and uncleaved peptides in mean $z_1$ scale (polarity related) and $z_2$ scale (size related) principal component metrics is shown for each of the 20 different amino acids found at P1 (i.e. the anchor), with the pattern for alanine highlighted. The graphic shows the differential in these metrics between the anchor position (differential zero) and the adjacent subsite positions for the cleaved and random uncleaved CSOs. Distinct patterns are apparent for cleaved compared to uncleaved peptides. Human and murine cathepsin L generate notably different patterns. While this may be attributable to the fact that the data were derived from different experiments, BLAST results of the human and murine enzymes indicate that they have only about 72% sequence identity. Hence although they both have the "L" designation it is likely that the two peptidases are not orthologous. Turk, V. et al. Cysteine cathepsins: from structure, function and regulation to new frontiers. Biochim. Biophys. Acta 1824, 68-88 (2012). When P1' is used as the anchor residue analogous unique patterns for each amino acid are seen (not shown). The patterns suggest that with human cathepsin L, whatever the polarity of amino acid at P1, on average a more apolar or hydrophobic residue occupies the P2 (FIG. 1, panel a, b). The situation is quite different for the murine cathepsin L (panels c, d). The patterns also show that changes in $z_2$ scale (size related) occur on the prime side for both the human and murine enzymes (e, f, g, h) concomitant with changes in the $z_1$ scale (polarity related) of residues on the non-prime side of the scissile bond. Similar patterns occur using the third principal component metric, $z_3$ scale (electronic related, not shown). These simultaneously changing patterns are why regression approaches simultaneously using multiple physical properties can be effective at fitting the underlying patterns, and hence provide the basis for using those discriminant equations to predict the probability of cleavage of other peptides.

As with changes in the means of the $z_1$ and $z_2$ scales, there are also differences in the variance (standard deviation) of these physical properties between the cleaved and uncleaved peptides at each of the positions in the CSO. Several notable features of the patterns are shown in FIG. 2. At positions P4 and P3 the variation between the cleaved and non-cleaved peptides is not different from random, as indicated by the intersection of the confidence intervals of nearly all of the peptidases. For the remaining positions however, there are distinct differences between the variation of the cleaved peptides and their random uncleaved cohorts, with each peptidase displaying a unique pattern. Taken together these patterns indicate how the least-squares process of fitting of the variation in physical property data might provide a means of characterization of the patterns for the different peptidases. A notable feature of the data is that the standard deviations at certain points are either greater or less than random. Examination of these patterns indicate that that a limited number of amino acids of similar physical properties will produce a standard deviation less than the random peptide set (e.g. human cathepsin B at P3' position at both 4 and 16 hr reaction times, panel f). A variation greater than random (e.g. murine cathepsin D and E at P3' seen in panel f) is anomalous and is due to multimodal distributions of amino acid type at those positions.

Application of Weighting Factor Patterns

Figure 3:
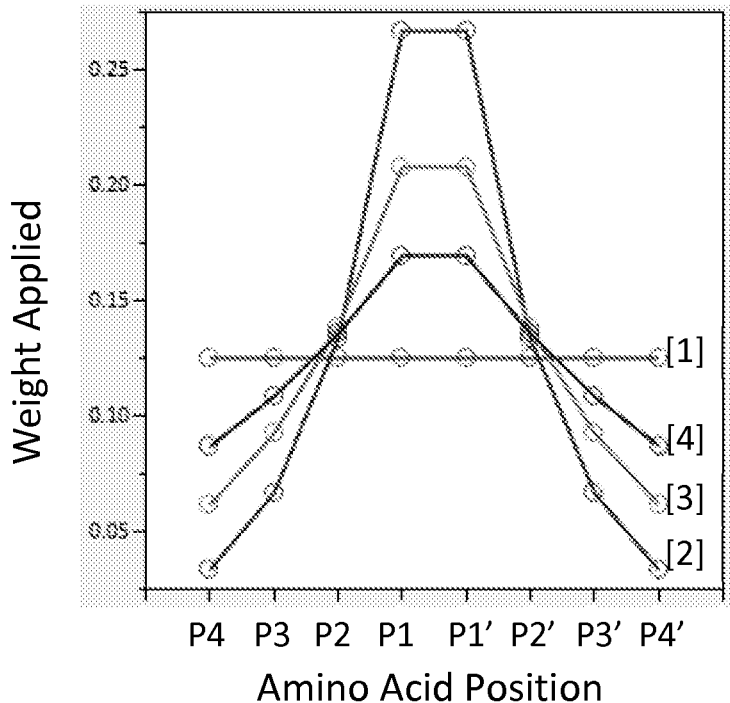

Examination of a large number of patterns like those shown in FIGS. 1 and 2 suggested that the amino acids nearest the cleavage site had the largest impact on whether or not cleavage occurred. This is also consistent with kinetic studies on several of the enzymes[14]. Based on this, a series of four unit-integral regression weighting patterns were developed (FIG. 3). The weighting vectors have a pivot point at amino acids P2 and P2' and provide an enhanced emphasis for the P1 and P1'positions and decreased emphasis for the positions more distal from the cleavage site. Unit integral weighting was used to decrease the possible influence of scale effects in the least-squared predictions. Duda, R. O., Hart, P. E., & Stork, D. G. Pattern Classification (John Wiley & Sons, Inc., 2001). As a control, tests showed that using uniform weighting, where each of the 3 principal component numbers at all positions within the CSO were multiplied by 0.125 produced predictions identical to the unweighted PCAA as input variables (not shown).

Figure 4:
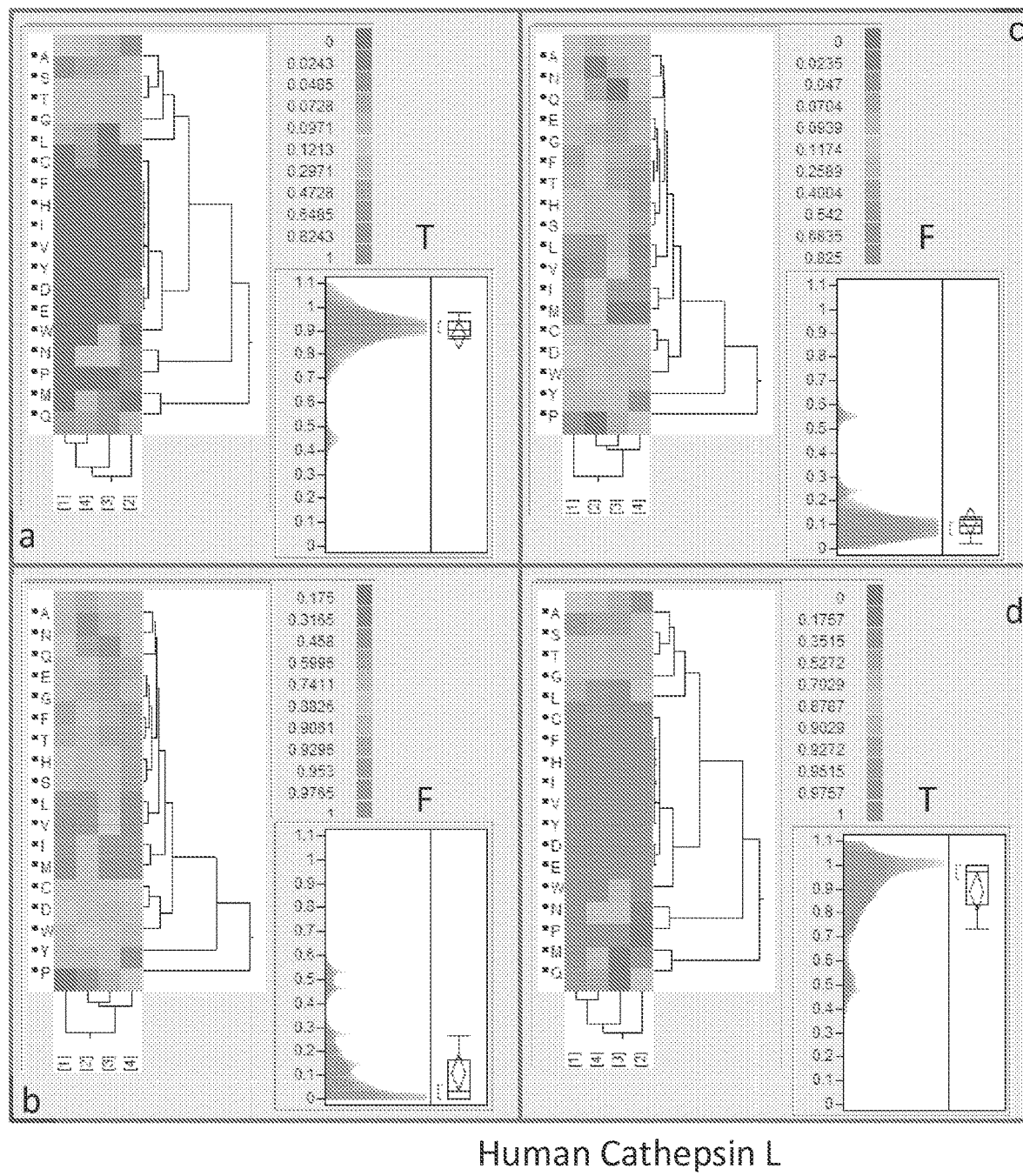
Figure 9:
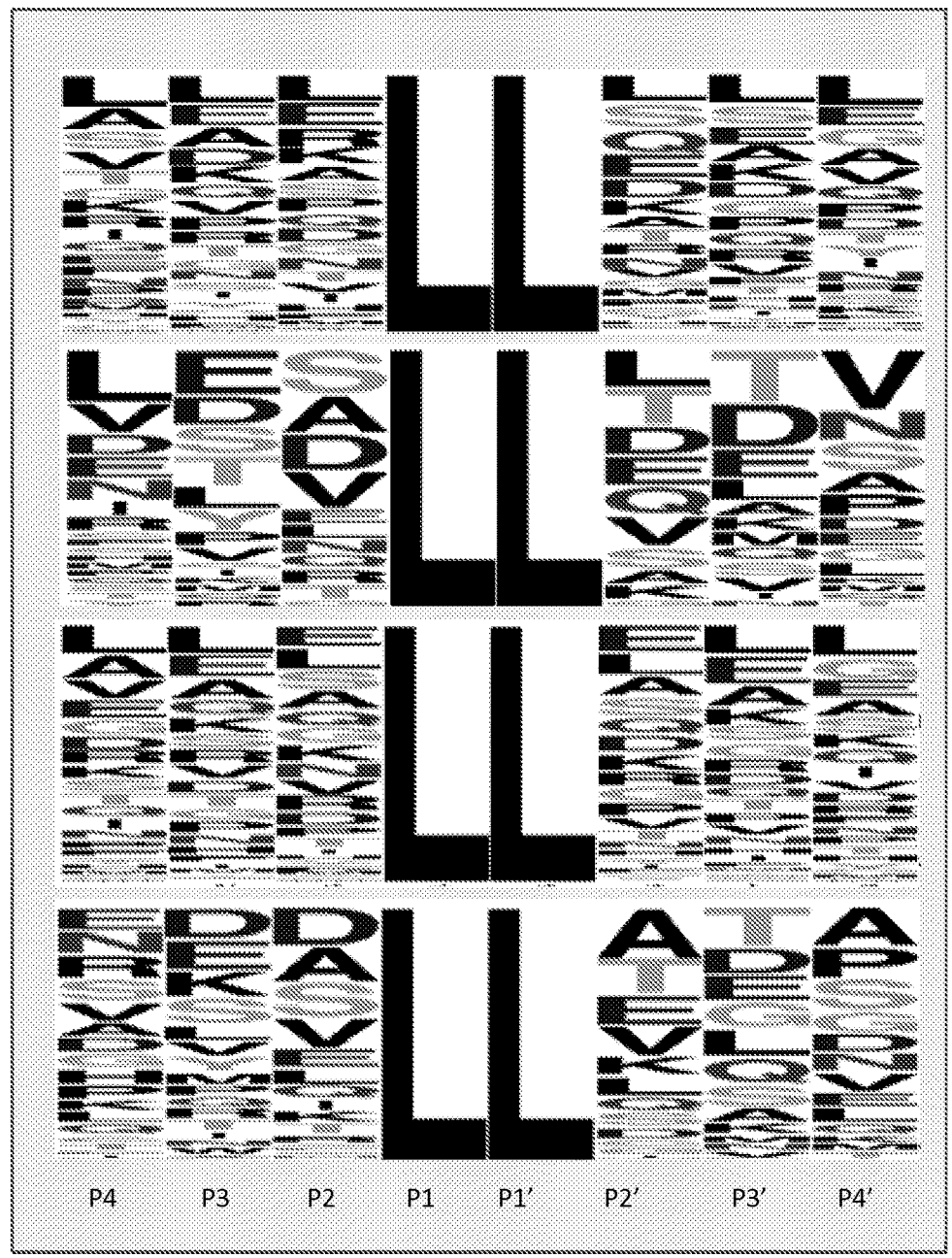

FIG. 4 shows the detailed performance data for the predictors for human cathepsin L. Equivalent graphics for human cathepsin B and S are found in FIG. 9 and FIG. 10. These patterns are a visualization of the composite of all of the prediction results for all peptides derived from the training sets with the 5 cohort ensemble sets each carried out the 4 different weighting factor patterns. See Biniossek et al., Impens et al., Tholen et al. Only the data for anchor position of P1 is shown, but analogous patterns are obtained using a P1' anchor. Overall the performance of the predictors has an average sensitivity and specificity of approximately 0.9. The performance is considerably better when certain amino acids are at the anchor position, than it is for others. Further, the impact of the weighting factor is large for certain amino acids and not for others. These differences in the predictor metrics are not due to the relative abundance of a particular amino acid at P1 or P1'; which because of the way the cohort sets were constructed greater abundance of a particular amino acid results in a larger training sets. Each of the peptidases has a unique pattern of sensitivity and specificity for particular amino acid anchors and these patterns are maintained at different reaction time points.

Amino Acids Generating Variable Performance

Figure 5:
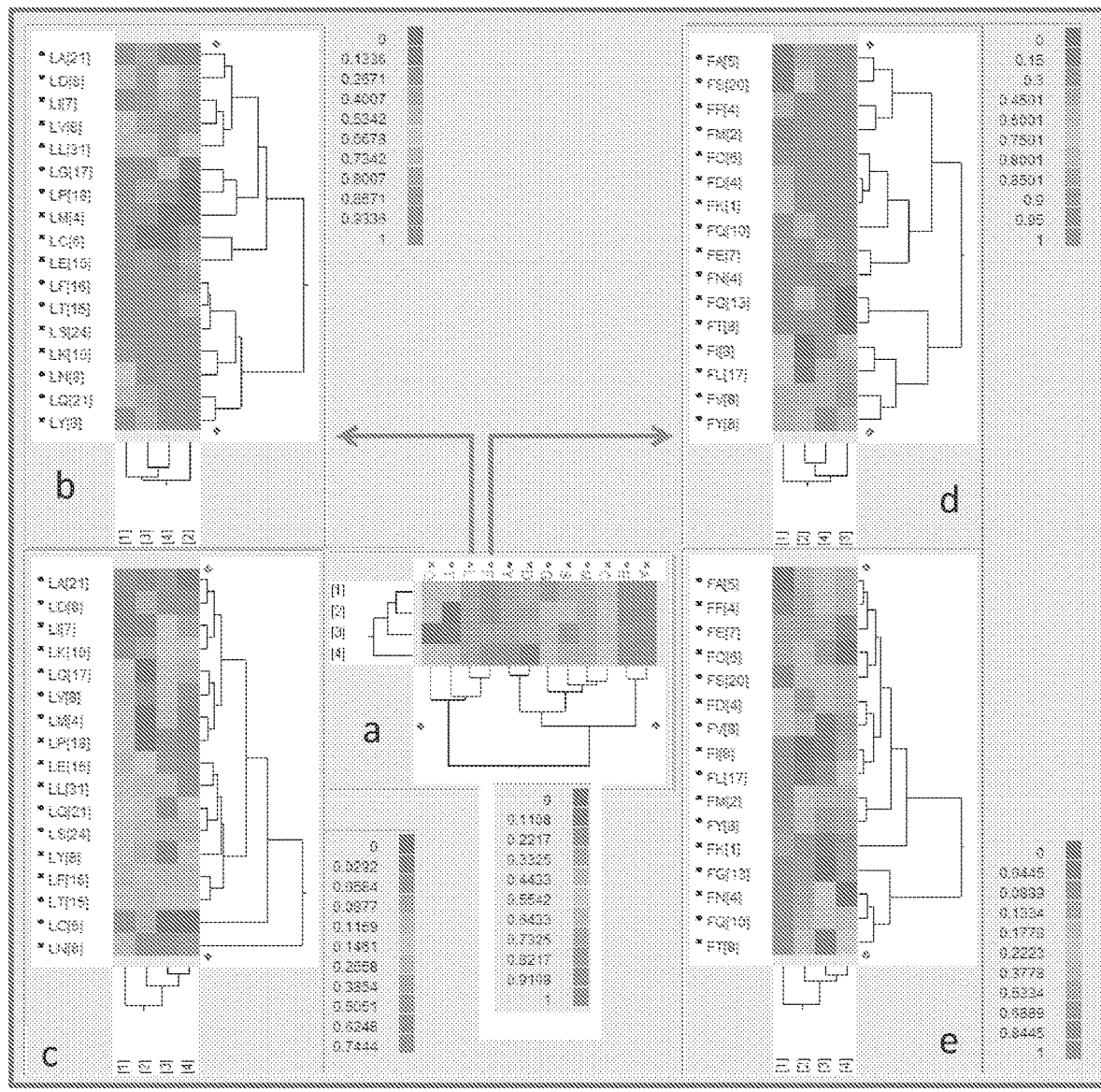

While many amino acid anchors gave consistently good results, for a few amino acids the performance of the predictors was problematic. Most obvious in this regard were the predictions for either a leucine or phenylalanine anchor at P1 in murine cathepsin D and E. The results for cathepsin E are shown in FIG. 5. Interestingly, similarly poor performance was seen with these amino acids anchoring the P1' position as well (not shown). This problem could be partially rectified using a dual anchor approach where P1 and P1' were both fixed, and thus the prediction process effectively limited to predicting how the flanking three positions on each side affect the probability of cleavage. This improved performance of the predictors for some amino acids, but a few continue to be problematic. A clue to the possible reason underlying for this can be seen in frequency logos (FIG. 11). The amino acids with poor prediction metrics are frequently found in series (e.g. ~LLLL~). The numerical consequence of sequentially repeating runs of these amino acids within the CSO would be that the all three z-scale vectors for those peptides would have a series of identical numbers in the least-squares analysis and thus render no pattern-predictive value. Nevertheless, even using the dual-anchored predictors, sensitivity and specificity values for murine cathpesins D, E and L were lower than for the other peptidases, ranging from 0.80-0.85 (FIG. 13). It is perhaps noteworthy that the input datasets where these characteristics occur are from degradomic techniques, as opposed to the peptide-centric approach PIC.

Example 2

Comparison with Support Vector Machine Prediction

Support vector machines are a commonly used type of classifier and in a variety of tests have been generally been shown to perform very well. Because of the underlying mathematics SVMs are thought to be less susceptible to over-fitting than neural networks. The e1071 R (www.r-project.org/) package implements one of the most widely used object code libraries (www.csie.ntu.edu.tw/~cjlin/libsvm/) of an SVM that has been widely tested. JMP® V10 has the ability to send data to and execute statistical routines in the R package and to capture the results returned. Therefore the R SVM was compared with the JMP® probabilistic neural net using the same training sets and the same multiple ensemble cross validation approach.

The training sets used were from human cathepsin L cleavage. See Binissek et al. Two unweighted training sets were used, one with alanine at the P1 anchor position and the other with glycine at the P1 anchor. The alanine training set contained 111 cleaved peptides and the glycine set contained 222 cleaved peptides. These amino acids were selected because they produced intermediate results in the NN (FIG. 4). The training process used a 5 K-fold cross-validation scheme as described above.

The SVM classifier was tuned for each cohort set by choosing an optimum C and gamma factor using the SVM-tune platform in the R package. The number of hidden nodes in the JMP® NN was fixed at 8 and the default settings used for controlling the convergence of the underlying algorithms.

FIG. 13 shows the results of the comparison. In this evaluation he NN out-performed the SVM in predicting the experimental results.

Example 3

Comparison with Experimental Data: Myelin Basic Protein

The data presented above are all derived from supplemental datasets in the papers indicated. Neural networks have an innate tendency to memorize what they have seen, so a fundamental question is how well do the predictors perform with other data that they have not "seen"? Over several decades there have been many studies of cathepsin peptidase cleavage specificity. Turk, V. et al. Cysteine cathepsins: from structure, function and regulation to new frontiers. Biochim. Biophys. Acta 1824, 68-88 (2012). A comprehensive study was conducted by Beck et al. in which both lysozomal extracts and several cathepsins, applied individually and in combination, were applied to the C-terminal half of myelin basic protein, a relatively small protein implicated in the etiology of multiple sclerosis. Because of its design the study allows comparison of peptidases used individually and in combinations and therefore provides a useful comparative dataset.

The sequence for the myelin basic protein isoform used by Beck et al. Genbank ID (17378805; P02686) was retrieved from NCBI. The molecule was dissected into octomers for use in predictions. The CSOs stratified by P1 and P1' and the discriminant functions operating on the CSO produced a cleavage probability at the P1 or P1' of the particular peptide. The cleavage predictions produced by the discriminate functions for the different peptidases at different times are highly concordant; for simplification of presentation the different discrimination functions for each of the peptidases was consolidated.

Figure 6:
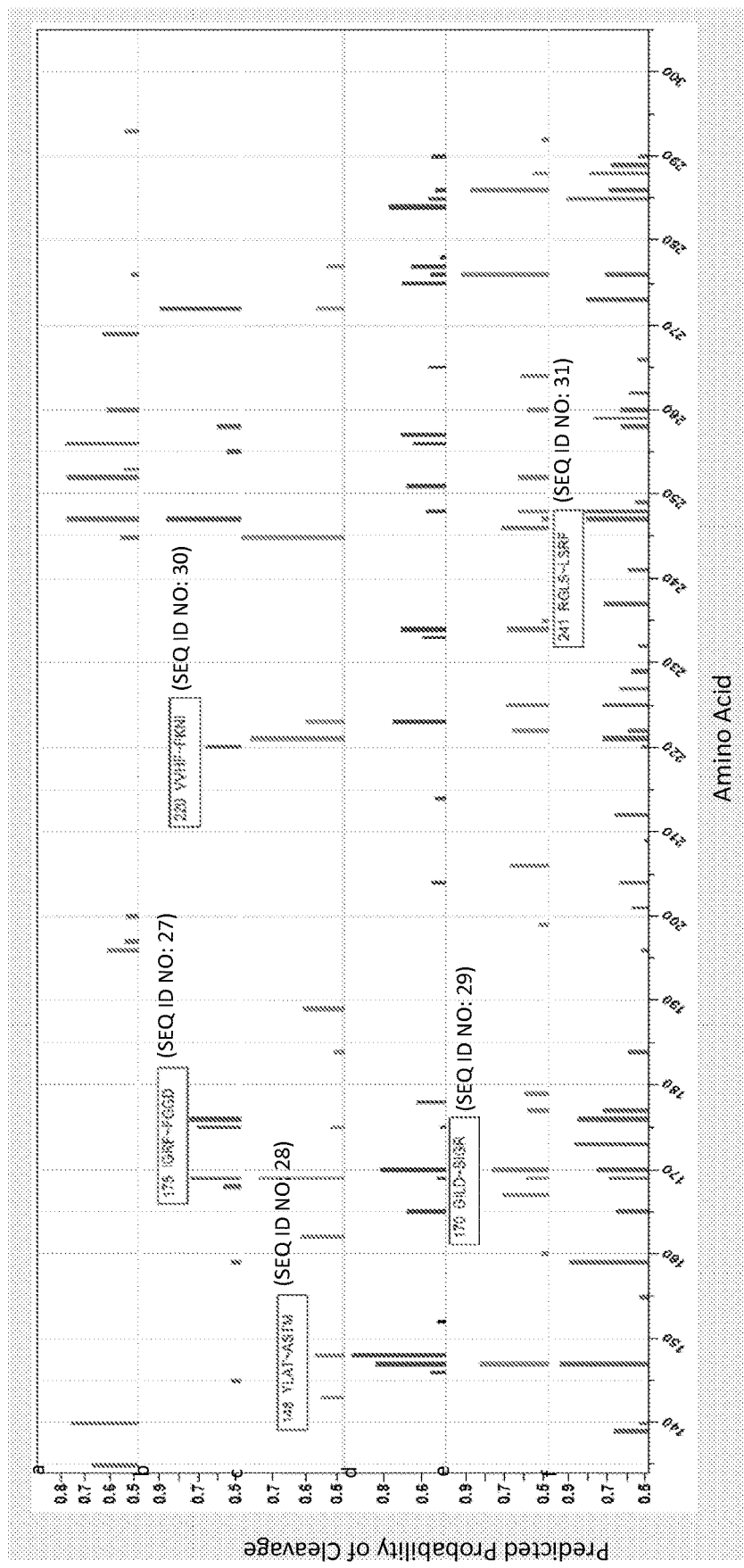

FIG. 6 shows the consolidated results of using the PCAA predictors of both P1 and P1' for the C-terminal segment of same isoform of myelin basic protein used by Beck et al.

The overall concordance between the experimental results and the predicters is quite good, but it is complex and can best be appreciated by comparing the patterns in FIG. 6 with those in FIG. 3 of the original Beck et al publication. Inset sequences in FIG. 6 are several cleavage sites identified by the authors as critical to the immune response to myelin basic protein. In line with other experimental results the predictions for the cathepsins used tend to show partially redundant cleavage specificity. Turk et al. Interestingly, for a large number of the cleavages where Beck et al attribute cleavage to bulk lysosomal activity, the predictors for cathepsin B (not used by Beck et al), cathepsin D or E were found to indicate high probabilities of cleavage.

Example 4

Prediction of Peptidase Cleavage Sites in Plant Allergens

Proteins from peanuts are well known as allergens. Stanley et al (Stanley, J. S. et al. Identification and mutational analysis of the immunodominant IgE binding epitopes of the major peanut allergen Ara h 2. Arch. Biochem. Biophys. 342, 244-253 (1997)) described IgE binding epitopes in the major peanut allergen Ara h2, referring to isoform 1. Prickett et al (Prickett, S. R. et al. Ara h 2 peptides containing dominant CD4+ T-cell epitopes: candidates for a peanut allergy therapeutic. J. Allergy Clin. Immunol. 127, 608-615 (2011)) characterized five CD4+ epitopes in this protein. An analysis of the peptidase cleavage sites in this protein was performed using the methods described herein. FIG. 16 shows the predicted cleavage sites by multiple cathepsins. A cleavage site was predicted immediately prior (N terminal side) to each of three epitope peptides characterized by Prickett.

Example 5

Binding Characteristics and Cleavage of the CLIP Peptides

The "CLIP" peptide (MHC Class II invariant peptide) is produced by endosomal cleavage of the MHC gamma, also known as the "invariant chain". The MHC-gamma allele is one of the genes in the MHC locus and has substantial structural similarity to the MHC molecules. It appears to have two purposes: First, a portion of the molecule binds in the molecular groove of the MHC II molecule and is used as a chaperone for guiding the MHC II molecule in the endosomal compartment where peptide loading takes place. Second, the CLIP peptide when released by endosomal peptidase activity, binds only with a moderate binding affinity to many different MHC II alleles and serves as a placeholder for other peptides that will be loaded into the MHC molecule in its place with the assistance of MHC-DM for ultimate presentation on the surface of the antigen presenting cell.

Experimental evidence shows that the so-called "CLIP peptide" is not a single peptide but actually a group of peptides with slightly different lengths (ragged ends) produced by differential endosomal peptidase cleavage activity. The longest of these peptides has the sequence

```
                              (SEQ ID NO: 5)
LPKPPKPVSKMRMATPLLMQALPMG.
```

The underlined sequence has been shown in experiments by others (Chicz R M et al, 1993 J Exp Med., Specificity and Promiscuity among Naturally Processed Peptides Bound to HLA-DR Alleles; Villadangos, J A et al 1997, J Exp Med, Degradation of Mouse Invariant Chain: Roles of Cathepsins S and D and the Influence of Major Histocompatability Complex Polymorphism) to be the primary binding region. It has the characteristic of binding to many different MHC II molecules (so is sometimes called a promiscuous peptide) with what is generally considered a moderate affinity of about e6.26=525 nM equivalent to about −0.96σ (approx −1σ) below the mean (FIG. 17). In fact, the neural net (NN) predictions suggest that several different binding registers will bind with a very similar binding affinity (IC50). An interesting feature of this molecule was determined recently where new experiments (Schlundt, A. 2012, J Mol. Biol Peptide Linkage to the alpha Subunit of MHC II Creates a Stably Inverted Antigen Presentation Complex) suggest that the peptide can bind, not only in the standard or canonical N◇C orientation, but also in the reverse C◇N orientation. Interestingly, the NN predictions for binding of the reverse peptide are also very comparable to the canonical orientation. As can be seen in FIG. 18, for several binding registers the affinity is actually higher for the inverted orientation that the canonical. A caveat to this observation is that the experimental procedures that are used to estimate the binding affinity to an MHC molecule are a bulk measurement done without knowledge of which orientation the peptides are assuming. It could be that the molecule assumes N◇C orientation or a C◇N or a mixture of the two. FIG. 19 shows the predicted binding affinity in several different binding registers for the canonical and inverted peptide orientation for a single common human MHC II allele (DRB1*01:01). The results are typical of those observed for the other 27 human alleles, as well as those from other species such as the mouse.

It follows that peptides from proteins of other derivations (including but not limited to microbial, mammalian, insect, allergen, etc.) may also be bound to MHC molecules in canonical or non-canonical orientation and thus may be presented by MHC as T cell epitopes in either orientation.

Furthermore, with reference to CLIP, the experimental determinations (Chicz et al vide infra) of peptide presentation by MHC molecules on antigen presenting cells provided a system for independent verification of the cathepsin cleavage predictions. The peptides presented on the MHC molecules at the cell surface should have been excised by the endosomal peptidases. Therefore the NN cleavage predictions for the endosomal peptidases, cathepsin B, L and S were compared to the N and C termini of the presented peptides. The cleavage predictions were found to be highly concordant with peptides attached to MHC II molecules and which had been detected by mass spectrometry. The endosomal peptidases are quite aggressive enzymes and cleave at a wide variety of amino acid sequences. Consistent with this, several different cleavage positions are predicted in this vicinity of the CLIP peptide molecule. The median length of peptide eluted and detected by mass spectrometry is 17 amino acids or two amino acids longer than the 15-mer binding pocket in the MHC II molecule generally recognized. The results of this Comparison are shown in FIG. 20. The experiments were carried out with virus transformed human B cells and in this cell type cathepsin S is thought to be the predominant endopeptidase activity. The primary eluted peptide (MRMATPLLMQALPM; SEQ ID NO:6) can be seen in FIG. 20 to be bracketed by the cathepsin S cleavage on both the N- and C-termini.

In addition to the invariant chain several additional peptides were also found loaded into the MHC II molecule (Chicz et al, vide infra). These peptides had "ragged" ends extending several amino acids in both the N-terminal and C-terminal side of the binding pocket. In each case the cleavage predictions matched the peptides that were detected.

The experiments described above with reference to CLIP showed a critical relationship between cathepsin cleavage and MHC presentation. The observations with MHC II were extended and shown to also be consistent with observations with respect to MHC I presentation of the shorter 9-mer peptides. Peptides presented on cell surfaces bound to MHC I molecules arise via proteasomal cleavages of protein molecules tagged for destruction in the cytoplasm. Resulting fragments produced in this part of the process are longer (up to about 20-mers) than can be accommodated in the binding pocket of MHC I molecules. These fragments are delivered to the MHC loading compartment by specialized molecular machinery called TAP (transporter associated antigen processing) where the resident peptidases trim the peptides to fit into the binding groove.

Example 6

Prediction of Peptidase Cleavage Sites in an Immunogenic *Brucella melitensis* Protein A publication by Durward et al (Durward, M. A., Harms, J., Magnani, D. M., Eskra, L., & Splitter, G. A. Discordant *Brucella melitensis* antigens yield cognate CD8+ T cells in vivo. *Infect. Immun.* 78, 168-176 (2010)) reported the experimental evidence for a cytotoxic CD8+ epitope in *Brucella melitensis* methionine sulphoxide reductase B. The 9-mer peptide of interest was RYCINSASL (SEQ ID NO: 7), located at positions 116 to 124. The predicted peptidase cleavages we determined by the methods described above. FIG. 15 shows the predicted cleavage by human cathepsins L, S and B and murine cathepsins D, E and L. It can be seen that there is a higher predicted probability of cleavage by cathepsin immediately proximal and distal to the peptide characterized by Durward et al.

Binding Characteristics and Cleavage of *Brucella melitensis* Methionine Sulphoxide Reductase A 9-mer peptide, RYCINSASL (RL9) (SEQ ID NO: 7) from *Brucella melitensis* methionine sulphoxide reductase B has been found to be presented on MHC I molecules and produce populations of T-cells which recognize the pMHC complex (Durward, M. et al 2010 Infection and Immunity Discordant *Brucella melitensis* Antigens Yield Cognate CD8 T Cells In Vivo). Further to the studies published by Durward et al., immunization of mice with the RL9 peptide leads to a protective response pattern in mice. Two versions of the RL-G2aFc molecule shown in FIG. 21 were produced, one with an N-terminal peptide fusion, the other with both N-terminal and C-terminal peptide fusions. Mice were immunized to test the two carrier proteins carrying known effective peptide (RL9). Mice immunized with the RL-G2a (CH2-CH3) or RL-G2a(CH2-CH3)-RL construct were able to reduce the number of RL9-pulsed target cells at a significantly higher rate than control immunized mice (FIG. 22) indicating that RL-G2a(CH2-CH3) vaccine induces a cellular cytotoxic response against target splenocytes displaying RL9 peptide, consistent with the protective response pattern known to eliminate *Brucella* infection. The data show the G2a(CH2-CH-3) carrier protein bearing the larger CEG peptide is correctly cleaved and RL9 peptide specific effector cells are created.

In view of the observations of the critical role of cathepsin cleavage in presentation of CLIP peptides, described in the Example 5 above, an experiment was designed to further examine the role of cathepsin in epitope definition.

An interesting feature of the peptide identified, RYCINSASL (SEQ ID NO: 7), is that it is derived from the active site of a metabolic enzyme widely distributed in nature. Mice contain the identical 9-mer peptide in their mitochondrial version of the enzyme. Thus, it would be expected that the mice would recognize the RYCINSASL (SEQ ID NO: 7) peptide as "self" and not produce an immunological response. Nevertheless, mice infected with *B. melitensis* produce a profound immunological response to this peptide; it is not recognized as self. The flanking residues outside of the active site 9-mer are quite different between the murine endogenous and *B. melitensis* forms of the enzyme. The differences in amino acids in the flanking positions change the probability of the N- and C-terminal bonds being cleaved. In contrast to the peptide from *B. melitensis*, the peptide in the mouse mitochondrial enzyme is not predicted to be excised (FIG. 23).

In order to test this experimentally, 6 amino acids on the N- and C-terminal side of the RL9 peptide in the *Brucella* enzyme were replaced to make it non-cleavable. This is shown in FIG. 24.

Cloning of *Brucella* RL(105-135) Peptides into mG2a Carrier

Existing wild-type *Brucella* RL(105-135) peptide cloned into p500695. The wt *Brucella* amino acid sequence contains cathepsin S cleavage sites upstream of the RL9 peptide as shown in SEQ 1 and 2.

Modified *Brucella* RL(105-135)mod peptide was cloned into mG2a carrier, this sequence has the RL9 flanking regions from *Brucella* replaced with murine flanking regions that are predicted to have no cathepsin S cleavage sites, the two flanking regions are marked in SEQ 3 and 4 and in FIG. 8.

Cloning procedure: The amino acid sequence encoding *Brucella melitensis* methionine sulfoxide reductase (Accession #NP_541797) position aa 105-135 was backtranslated using the Lasergene software (DNAstar, Madison, Wis.) built-in mammalian non-degenerate backtranslation code. Proper restriction enzyme sites were added to both ends of the RL(105-135) sequence and the nucleotide sequence was synthesized using a commercial vendor (IDT, Coralville, Iowa). The sequence for the modified RL(105-135)mod was similarly assembled in silico and then submitted for synthesis. The obtained synthesized RL(15-135) gene sequences are digested with the specific restriction sites and in-frame cloned upstream of the murine G2a (hinge-CH2-CH3)-containing retroviral expression retrovector.

In vivo testing: The expression retrovectors containing the RL(105-135) or RL(105-135)mod sequence were used to make stable CHO expression cell lines to produce both peptides as N-terminal murine IgG2a hinge-Fc portion. BR-RL(105-135)-mG2a and BR-RL(105-135)mod-mG2a is harvested from cell supernatant and used to immunize mice via subcutaneous injection at the tail at 25 ug/mouse dose and formulated with Sigma (S6322) and CpG adjuvants. One or two boosts are given after the first injection. One week after the last boost, splenocytes are collected from immunized mice and cultivated in vitro. Splenocytes from naïve mice are pulsed with synthesized RL9 or irrelevant control peptide and then added to the harvested effector cells. After a 5 h incubation, cells are harvested and monitored for T-cell phenotype (CD4, CD8, CD3), activation status (LFA-1) and intracellular cytokine (INFg) production using flow cytometry. This analysis will yield information as to whether the removal of a predicted cathepsin cleavage site changes processing of peptides upon uptake by antigen presenting cells and subsequent stimulation of T-cells.

It is anticipated that mice vaccinated with the modified peptide sequence will not display the peptide on the MHC I surface molecules nor generate a T-cell response.

age sites characterizes prime and non-prime specificity of cysteine cathepsins B, L, and S. *J. Proteome. Res.* 10, 5363-5373 (2011).

```
Seq. Id No. 1. BR-RL(105-135)-G2a(CH2-CH3)-BR-RL,
nucleotide sequence, ID:500695n
         .........o.........o.........o.........o.........o
     1   TTCCCCGACGGCCCCGTGGACCGCGGCGGCCTGCGCTACTGCATCAACTC

51   CGCCTCCCTGCGCTTCGTGCCCAAGGACCGCATGGAGGCCGAG 1-93   BR-RL(105-135)

Seq. Id No. 2. BR-RL(105-135)-G2a(CH2-CH3)-BR-RL,
amino acid sequence, ID:500695p
         .........o.........o.........o.........o.........o
  1-31   FPDGPVDRGGLRYCINSASLRFVPKDRMEAE Seq. Id No. 3. BR-RL(105-135)mod-G2a(CH2-CH3)-BR-
RL, nucleotide sequence, ID:500695n
         .........o.........o.........o.........o.........o
     1   TTCCCCGACGGCCCTCCTCGTCCGACCGGCAAAAGATACTGCATCAACTC

51   AGCATCCTTGTCCTTCACTCCTGCAGACCGCATGGAGGCCGAG 1-15   Brucella sequence 16-33   Murine sequence 34-60   Brucella RL9 peptide 61-78   Murine sequence 79-93   Brucella sequence Seq. Id No. 4. BR-RL(105-135)mod-G2a(CH2-CH3)-BR-
RL, amino acid sequence, ID:500695p
         .........o.........o.........o.........o.........o
  1-31   FPDGPPRPTGKRYCINSASLSFTPADRMEAE 1-5   Brucella sequence 6-11   Murine sequence 12-20   Brucella RL9 peptide 21-26   Murine sequence 27-31   Brucella sequence
```

REFERENCE LIST

1. Kleifeld, O. et al. Isotopic labeling of terminal amines in complex samples identifies protein N-termini and protease cleavage products. *Nat. Biotechnol.* 28, 281-288 (2010).
2. Doucet, A., Butler, G. S., Rodriguez, D., Prudova, A., & Overall, C. M. Metadegradomics: toward in vivo quantitative degradomics of proteolytic post-translational modifications of the cancer proteome. *Mol. Cell Proteomics.* 7, 1925-1951 (2008).
3. auf dem, K. U. & Schilling, O. Proteomic techniques and activity-based probes for the system-wide study of proteolysis. *Biochimie* 92, 1705-1714 (2010).
4. Impens, F. et al. MS-driven protease substrate degradomics. *Proteomics.* 10, 1284-1296 (2010).
5. Agard, N. J. & Wells, J. A. Methods for the proteomic identification of protease substrates. *Curr. Opin. Chem. Biol.* 13, 503-509 (2009).
6. Schilling, O. & Overall, C. M. Proteome-derived, database-searchable peptide libraries for identifying protease cleavage sites. *Nat. Biotechnol.* 26, 685-694 (2008).
7. Biniossek, M. L., Nagler, D. K., Becker-Pauly, C., & Schilling, O. Proteomic identification of protease cleav-
8. Impens, F. et al. A quantitative proteomics design for systematic identification of protease cleavage events. *Mol. Cell Proteomics.* 9, 2327-2333 (2010).
9. Tholen, S. et al. Contribution of cathepsin L to secretome composition and cleavage pattern of mouse embryonic fibroblasts. *Biol. Chem.* 392, 961-971 (2011).
10. Schechter, I. & Berger, A. On the size of the active site in proteases. I. Papain. *Biochem. Biophys. Res. Commun.* 27, 157-162 (1967).
11. Ng, N. M. et al. The effects of exosite occupancy on the substrate specificity of thrombin. *Arch. Biochem. Biophys.* 489, 48-54 (2009).
12. Boyd, S. E., Pike, R. N., Rudy, G. B., Whisstock, J. C., & Garcia, d. l. B. PoPS: a computational tool for modeling and predicting protease specificity. *J. Bioinform. Comput. Biol.* 3, 551-585 (2005).
13. Shen, H. B. & Chou, K. C. Identification of proteases and their types. *Anal. Biochem.* 385, 153-160 (2009).
14. Chou, K. C. & Shen, H. B. ProtIdent: a web server for identifying proteases and their types by fusing functional domain and sequential evolution information. *Biochem. Biophys. Res. Commun.* 376, 321-325 (2008).
15. Lohmuller, T. et al. Toward computer-based cleavage site prediction of cysteine endopeptidases. *Biol. Chem.* 384, 899-909 (2003).

16. Song, J. et al. Bioinformatic approaches for predicting substrates of proteases. *J. Bioinform. Comput. Biol.* 9, 149-178 (2011).
17. Yang, Z. R. Prediction of caspase cleavage sites using Bayesian bio-basis function neural networks. *Bioinformatics.* 21, 1831-1837 (2005).
18. Rognvaldsson, T. et al. How to find simple and accurate rules for viral protease cleavage specificities. *BMC. Bioinformatics.* 10, 149 (2009).
19. Rognvaldsson, T. & You, L. Why neural networks should not be used for HIV-1 protease cleavage site prediction. *Bioinformatics.* 20, 1702-1709 (2004).
20. El-Manzalawy, Y., Dobbs, D., & Honavar, V. On evaluating MHC-II binding peptide prediction methods. *PLoS. One.* 3, e3268 (2008).
21. Bremel, R. D. & Homan, E. J. An integrated approach to epitope analysis I: Dimensional reduction, visualization and prediction of MHC binding using amino acid principal components and regression approaches. *Immunome. Res.* 6, 7 (2010).
22. Bremel, R. D. & Homan, E. J. An integrated approach to epitope analysis II: A system for proteomic-scale prediction of immunological characteristics. *Immunome. Res.* 6, 8 (2010).
23. Sjostrom, M. et al. Peptide QSARS: PLS modelling and design in principal properties. *Prog. Clin. Biol. Res.* 291, 313-317 (1989).
24. Hellberg, S., Sjostrom, M., Skagerberg, B., & Wold, S. Peptide quantitative structure-activity relationships, a multivariate approach. *J. Med. Chem.* 30, 1126-1135 (1987).
25. Linusson, A., Elofsson, M., Andersson, I. E., & Dahlgren, M. K. Statistical molecular design of balanced compound libraries for QSAR modeling. *Curr. Med. Chem.* 17, 2001-2016 (2010).
26. Linusson, A., Gottfries, J., Lindgren, F., & Wold, S. Statistical molecular design of building blocks for combinatorial chemistry. *J. Med. Chem.* 43, 1320-1328 (2000).
27. Du, Q. S., Huang, R. B., & Chou, K. C. Recent advances in QSAR and their applications in predicting the activities of chemical molecules, peptides and proteins for drug design. *Curr. Protein Pept. Sci.* 9, 248-260 (2008).
28. Bishop, C. M. *Neural Networks for Pattern Recognition* (Oxford University Press, Oxford, 1995). 29. Turk, V. et al. Cysteine cathepsins: from structure, function and regulation to new frontiers. *Biochim. Biophys. Acta* 1824, 68-88 (2012).
30. Duda, R. O., Hart, P. E., & Stork, D. G. *Pattern Classification*(John Wiley & Sons, Inc., 2001).
31. Beck, H. et al. Cathepsin S and an asparagine-specific endoprotease dominate the proteolytic processing of human myelin basic protein in vitro. *Eur. J. Immunol.* 31, 3726-3736 (2001).
32. Du, Q. S., Wei, Y. T., Pang, Z. W., Chou, K. C., & Huang, R. B. Predicting the affinity of epitope-peptides with class I MHC molecule HLA-A*0201: an application of amino acid-based peptide prediction. *Protein Eng Des Sel* 20, 417-423 (2007).
33. Choo, K. H., Tan, T. W., & Ranganathan, S. A comprehensive assessment of N-terminal signal peptides prediction methods. *BMC. Bioinformatics.* 10 Suppl 15, S2 (2009).
34. Colaert, N., Helsens, K., Martens, L., Vandekerckhove, J., & Gevaert, K. Improved visualization of protein consensus sequences by iceLogo. *Nat. Methods* 6, 786-787 (2009).
35. Rigaut, K. D., Birk, D. E., & Lenard, J. Intracellular distribution of input vesicular stomatitis virus proteins after uncoating. *J. Virol.* 65, 2622-2628 (1991).
36. Schilling, O., auf dem, K. U., & Overall, C. M. Factor Xa subsite mapping by proteome-derived peptide libraries improved using WebPICS, a resource for proteomic identification of cleavage sites. *Biol. Chem.* 392, 1031-1037 (2011).
37. Chou, K. C. Some remarks on protein attribute prediction and pseudo amino acid composition. *J. Theor. Biol.* 273, 236-247 (2011).
38. Chawla, N., Lazarevic, A., Hall, L., & Bowyer, K. SMOTEBoost: Improving prediction of the minority class in boosting. *Knowledge Discovery in Databases: PKDD* 2003 107-119 (2003).
39. Chawla, N., Eschrich, S., & Hall, L. O. Creating ensembles of classifiers. Data Mining, 2001.ICDM 2001, Proceedings IEEE International Conference on, 580-581. 2001. IEEE. 40. Chawla, N. V. Data mining for imbalanced datasets: An overview. *Data Mining and Knowledge Discovery Handbook* 875-886 (2010).
41. Cieslak, D. A. & Chawla, N. V. Start globally, optimize locally, predict globally: Improving performance on imbalanced data. Data Mining, 2008.ICDM'08. Eighth IEEE International Conference on, 143-152. 2008. IEEE.
42. Lichtenwalter, R. & Chawla, N. Adaptive methods for classification in arbitrarily imbalanced and drifting data streams. *New Frontiers in Applied Data Mining* 53-75 (2010).
43. Tang, Y., Zhang, Y. Q., Chawla, N. V., & Krasser, S. SVMs modeling for highly imbalanced classification. *Systems, Man, and Cybernetics, Part B: Cybernetics, IEEE Transactions on* 39, 281-288 (2009).
44. Yu, B., Fonseca, D. P., O'Rourke, S. M., & Berman, P. W. Protease cleavage sites in HIV-1 gp120 recognized by antigen processing enzymes are conserved and located at receptor binding sites. *J. Virol.* 84, 1513-1526 (2010).
45. Beck, H. et al. Cathepsin S and an asparagine-specific endoprotease dominate the proteolytic processing of human myelin basic protein in vitro. *Eur. J. Immunol.* 31, 3726-3736 (2001). 46. Rawlings, N. D., Barrett, A. J., & Bateman, A. MEROPS: the database of proteolytic enzymes, their substrates and inhibitors. *Nucleic Acids Res.* 40, D343-D350 (2012).

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11069427B2). An electronic copy of the "Sequence Listing" will also be available from the USPTO upon request and payment of the fee set forth in 37 CFR 1.19(b)(3).

The invention claimed is:

1. A computer implemented process of identifying peptidase cleavage sites in a polypeptide comprising:
   a) obtaining an amino acid sequence for a target polypeptide;
   b) deriving an ensemble of peptidase cleavage prediction equations for each possible cleavage site dimer by:
      (i) assembling experimentally derived data comprising a multiplicity of measurements of amino acid physicochemical properties;
      (ii) producing a correlation matrix of the experimentally derived data;
      (iii) deriving by Principal Component Analysis multiple uncorrelated dimensionless, weighted and ranked proxy descriptors to describe at least 80% of the variance in said physicochemical properties of individual amino acids,
      (iv) using said proxy descriptors to describe individual amino acids in a set of peptides each of which comprises a specific cleavage site dimer experimentally determined to be cleaved, and to describe the individual amino acids in a set of peptides each of which comprises the same cleavage site dimer experimentally determined to be uncleaved;
      (v) comparing, via probabilistic modeling, the amino acid descriptors of said peptides comprising said experimentally determined cleaved and uncleaved cleavage site dimers to derive a cleavage prediction equation for said specific cleavage site dimer based on that peptide set;
      (vi) repeating the steps of (iv) and (v) multiple times, each time with a different set of peptides that comprise the same cleavage site dimer and are experimentally determined to be cleaved or not cleaved, thereby deriving an ensemble of independently derived peptidase cleavage prediction equations for said specific cleavage site dimer;
      (vii) repeating the process of (iv) to (vi) to derive ensembles of independently derived prediction equations for every possible cleavage site dimer up to a total of 400 such ensembles;
      (viii) storing said ensembles of independently derived prediction equations on a non-transitory computer readable medium;
   c) in-putting said amino acid sequence from said target polypeptide into a computer;
   d) applying said proxy descriptors from said Principal Component Analysis to describe individual amino acids in said target polypeptide sequence;
   e) deriving vectors to describe a plurality of peptides of defined length in said target polypeptide;
   f) via said computer processor applying said up to 400 ensembles of independently derived peptidase cleavage prediction equations to said plurality of peptides of defined length from said target polypeptide to predict a plurality of peptidase cleavage sites in said target polypeptide;
   (g) identifying, by consensus of the ensembles of prediction equations, the probability of cleavage at any given cleavage site dimer in said target polypeptide;
   (h) defining amino acids subsets in said target polypeptide that are predicted to be cleaved by a peptidase; and
   (i) determining if the resulting amino acid subsets are predicted to have MHC binding properties and to function as a T cell epitope that generates an immune response;
   (j) preparing an immunogen from amino acid subsets that are predicted to have MHC binding properties and to function as a T cell epitope that generates an immune response; and
   (k) administering an effective amount of the immunogen to a subject under conditions such that an immune response is generated.

2. The process of claim 1 wherein said probabilistic modeling is by a probabilistic neural net or a support vector machine.

3. The process of claim 2, wherein said probabilistic neural net comprises a multi-layer perceptron neural network regression process wherein the output is the probability of cleavage by a particular peptidase within a particular cleavage site dimer within a particular amino acid sequence.

4. The process of claim 3, wherein said probabilistic neural net predicts a peptidase cleavage site with greater than about 70, 80, 90, or 95% accuracy.

5. The process of claim 3, further comprising utilizing a number of hidden nodes in said multi-layer perceptron that correlates to the number of amino acids in the cleavage site octomer.

6. The process of claim 1, wherein said amino acid subset in said protein of interest is from about 4 to about 50 amino acids in length.

7. The process of claim 1, wherein said peptide of defined length is 8 amino acids in length.

8. The process of claim 1, wherein said subsets of amino acid sequences begin at n-terminus of the amino acid sequence, wherein n is the first amino acid of the sequence and c is the last amino acid in the sequence, and the sets comprise each peptide of 8 amino acids in length starting from n and the next peptide in the set is n+1 until n+1 ends at c for the given length of the peptides selected.

9. The process of claim 1, wherein said physicochemical properties of individual amino acids are selected from the group consisting of polarity, optimized matching hydrophobicity, hydropathicity, hydropathcity expressed as free energy of transfer to surface in kcal/mole, hydrophobicity scale based on free energy of transfer in kcal/mole, hydrophobicity expressed as ΔG ½ cal, hydrophobicity scale derived from 3D data, hydrophobicity scale represented as π–r, molar fraction of buried residues, proportion of residues 95% buried, free energy of transfer from inside to outside of a globular protein, hydration potential in kcal/mol, membrane buried helix parameter, mean fractional area loss, average area buried on transfer from standard state to folded protein, molar fraction of accessible residues, hydrophilicity, normalized consensus hydrophobicity scale, average surrounding hydrophobicity, hydrophobicity of physiological L-amino acids, hydrophobicity scale represented as (π–r)2, retension coefficient in HFBA, retention coefficient in HPLC pH 2.1, hydrophobicity scale derived from HPLC peptide retention times, hydrophobicity indices at pH 7.5 determined by HPLC, retention coefficient in TFA, retention coefficient in HPLC pH 7.4, hydrophobicity indices at pH 3.4 determined by HPLC, mobilities of amino acids on chromatography paper, hydrophobic constants derived from HPLC peptide retention times, and combinations thereof.

10. The process of claim 1, wherein said contribution of the physical properties of each amino acids in said subsets to the peptidase cleavage site is weighted according to the amino acid and its position in each peptide in said set of peptides.

11. The process of claim 1 wherein said process is applied sequentially to determine cleavage by two or more peptidases.

12. The process of claim 1, wherein said peptidase is a eukaryotic, prokaryotic, viral or synthetic peptidase.

13. The process of claim 1 wherein said peptidase is an endopeptidase drawn from the group comprising a serine peptidase, a cysteine peptidase, an aspartic peptidase, a glutamic peptidase, an asparagine peptidase, a threonine peptidase, or a metallo-peptidase.

14. The process of claim 1 wherein said peptidase is a cathepsin.

15. The process of claim 1, wherein said peptidase is in an antigen presenting cell.

* * * * *